United States Patent
Ten Grotenhuis et al.

(10) Patent No.: US 9,970,907 B2
(45) Date of Patent: May 15, 2018

(54) ULTRASOUND MATRIX INSPECTION

(71) Applicant: Ontario Power Generation Inc., Toronto (CA)

(72) Inventors: Raymond Ten Grotenhuis, Toronto (CA); Andrew Hong, Toronto (CA); Zhenxiang Chen, Woodbridge (CA); Matt Madill, Etobicoke (CA); Shaddy Shokralla, Toronto (CA); Benedict Cheng Chuen Wong, Richmond Hill (CA); Scott Preston, Toronto (CA); Alexander Sakuta, Toronto (CA)

(73) Assignee: Ontario Power Generation Inc., Toronto, Ontario (CA)

( * ) Notice: Subject to any disclaimer, the term of this patent is extended or adjusted under 35 U.S.C. 154(b) by 593 days.

(21) Appl. No.: 14/347,267

(22) PCT Filed: Sep. 26, 2012

(86) PCT No.: PCT/CA2012/000861
§ 371 (c)(1),
(2) Date: Mar. 26, 2014

(87) PCT Pub. No.: WO2013/044350
PCT Pub. Date: Apr. 4, 2013

(65) Prior Publication Data
US 2014/0238136 A1 Aug. 28, 2014

Related U.S. Application Data

(60) Provisional application No. 61/539,208, filed on Sep. 26, 2011, provisional application No. 61/546,217, filed on Oct. 12, 2011.

(51) Int. Cl.
*G01N 29/265* (2006.01)
*G01N 29/06* (2006.01)
(Continued)

(52) U.S. Cl.
CPC ....... *G01N 29/265* (2013.01); *G01N 29/0654* (2013.01); *G01N 29/11* (2013.01);
(Continued)

(58) Field of Classification Search
CPC .... G01N 29/265; G01N 29/27; G01N 29/275; G01N 29/28; G01N 29/0654;
(Continued)

(56) References Cited

U.S. PATENT DOCUMENTS 2,908,161 A * 10/1959 Bincer .................. G01N 29/26
310/336
4,807,476 A * 2/1989 Cook ................. G01N 29/0645
73/620

(Continued)

FOREIGN PATENT DOCUMENTS

| JP | H02-208554 | 8/1990 |
| JP | 2009-276319 | 11/2009 |
| JP | 2009-281805 | 12/2009 |

OTHER PUBLICATIONS

Ultrasonic Phased Array Inspection of Welded Pipes using Wave Mode-Converted at the Inner Surface of the Pipe, R. Long, et al., published on Dec. 31, 2009.
(Continued)

*Primary Examiner* — Paul West
*Assistant Examiner* — Xin Zhong
(74) *Attorney, Agent, or Firm* — Calfee, Halter & Griswold, LLP

(57) ABSTRACT

A device and method for performing ultrasound scanning of a substantially cylindrical object, the device comprising a cuff adapted to fit around a circumference of the object, a carrier mounted slidably on the cuff and adapted to traverse the circumference of the object, an ultrasound probe mounted on the carrier and positioned to scan the circum-
(Continued)

ference of the object as the carrier traverses the circumference of the object, a carrier motor mounted on the cuff or the carrier and used to drive the movement of the carrier about the circumference of the object, and one or more data connections providing control information for the carrier motor and the ultrasound probe and receiving scanning data from the ultrasound probe.

11 Claims, 53 Drawing Sheets

(51) Int. Cl.
G01N 29/11 (2006.01)
G01N 29/26 (2006.01)
G01N 29/44 (2006.01)

(52) U.S. Cl.
CPC ....... *G01N 29/262* (2013.01); *G01N 29/4472* (2013.01); *G01N 2291/044* (2013.01); *G01N 2291/2634* (2013.01)

(58) Field of Classification Search
CPC .. G01N 29/11; G01N 29/4472; G01N 29/262; G01N 2291/044; G01N 2291/2634
See application file for complete search history.

(56) References Cited

U.S. PATENT DOCUMENTS

| | | | |
|---|---|---|---|
| 6,137,853 A * | 10/2000 | Duckering | G21C 17/003 376/252 |
| 6,409,669 B1 | 6/2002 | Hager et al. | |
| 6,497,159 B1 * | 12/2002 | Lavoie | G01B 17/02 73/661 |
| 6,739,188 B1 | 5/2004 | Prause | |
| 6,935,178 B2 | 8/2005 | Prause | |
| 7,412,890 B1 | 8/2008 | Johnson et al. | |
| 7,823,454 B2 * | 11/2010 | MacLauchlan et al. | G01N 29/265 73/618 |
| 2008/0078742 A1 | 4/2008 | Hu et al. | |
| 2009/0025490 A1 | 1/2009 | Brandstrom | |
| 2009/0038398 A1 * | 2/2009 | Lavoie | G01N 29/225 73/637 |
| 2009/0078742 A1 | 3/2009 | Pasquali et al. | |
| 2009/0314089 A1 * | 12/2009 | Brignac | G01N 29/226 73/622 |
| 2010/0008462 A1 | 1/2010 | Killian et al. | |
| 2010/0107725 A1 | 5/2010 | Iizuka et al. | |
| 2012/0053856 A1 * | 3/2012 | Morrison, Jr. | G01N 29/262 702/39 |
| 2014/0060580 A1 * | 3/2014 | O'Donnell | B08B 9/027 134/18 |

OTHER PUBLICATIONS

Through-weld ultrasonic phased array inspection using full matrix capture, R. Long, et al., published on Jul. 31, 2009.
Long et al, "Ultrasonic phased array inspection of flaws on weld fusion faces using full matrix capture", Review of Quantitative Nondestructive Evaluation, vol. 28, 2009, p. 848-855, Proceedings of American Institute of Physics.
Long et al., "Through-weld ultrasonic phased array inspection using full matrix capture", Review of Quantitative Evaluation, vol. 29, 2010, p. 918-925, Proceedings of American Institute of Physics.
Weeks, A, "Fundamentals of Electronic Image Processing", Wiley-IEEE Press, Chapter 7—Image geometry and morphological filters, p. 294 -386; 1st edition; 1996.
International Search Report dated Jan. 22, 2013, for related International Application Serial No. PCT/CA2012/000861.
Written Opinion dated Jan. 22, 2013, for related International Application Serial No. PCT/CA2012/000861.

* cited by examiner

Figure 26(a)    Figure 26(b)
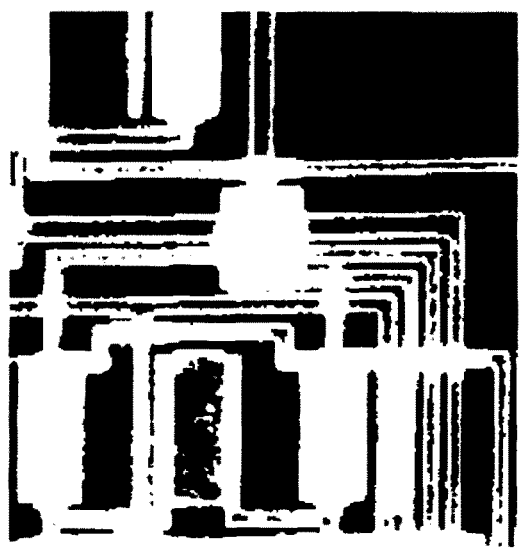 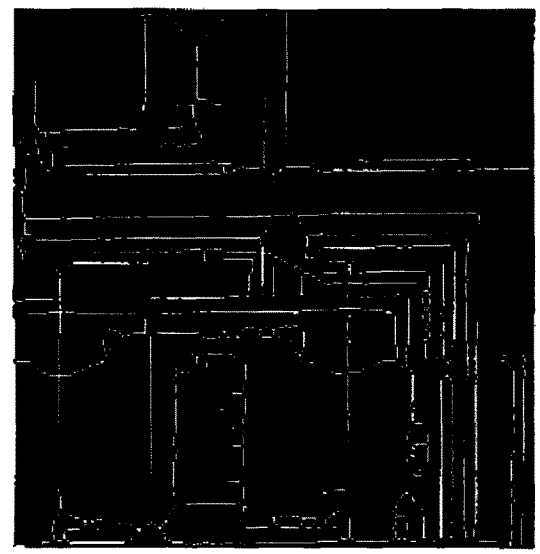
Figure 27(a)    Figure 27(b)

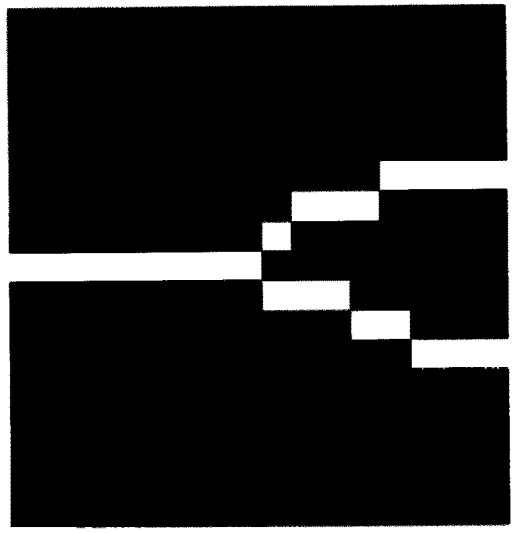 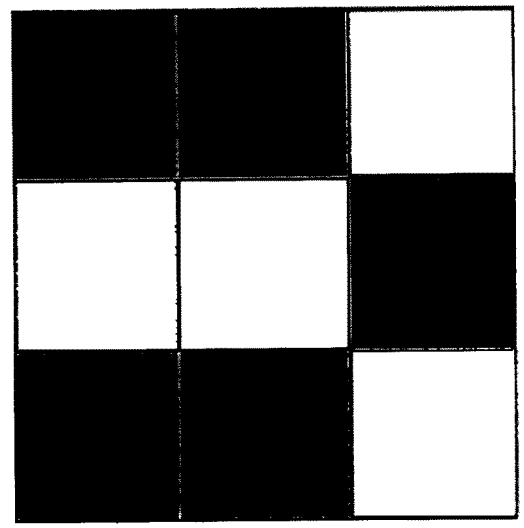
Figure 28(a)   Figure 28(b)
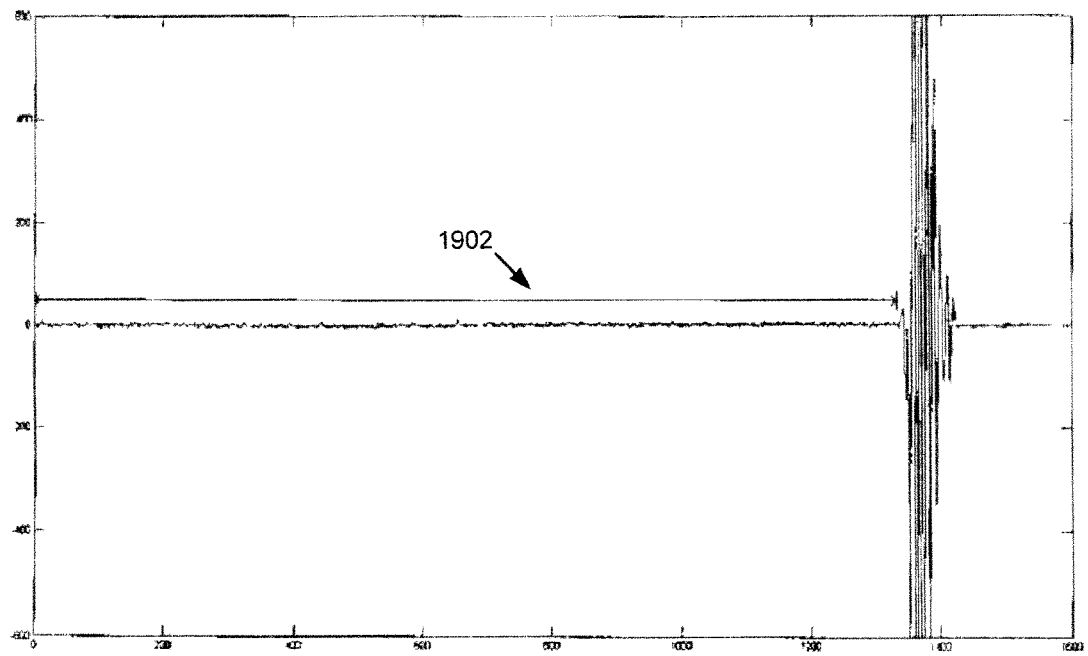
Figure 29

**Fitting to Fitting Weld
Inspection Zones**

Grayloc Weld Inspection Zones

Weld Root 0 - 3.2 mm wide
Weld Cap 7 - 16 mm wide

ULTRASOUND MATRIX INSPECTION

CROSS REFERENCE TO RELATED APPLICATIONS

The present application is a national phase entry under 35 U.S.C. § 371 of, and claims priority to, International Application No. PCT/CA2012/000861 filed on Sep. 26, 2012, for ULTRASOUND MATRIX INSPECTION, which claims the benefit of U.S. Provisional Patent Application No. 61/539,208, filed on Sep. 26, 2011, and U.S. Provisional Patent Application No. 61/546,217, filed on Oct. 12, 2011, the entire disclosures of which are fully incorporated herein by reference.

The content of the above patent applications are hereby expressly incorporated by reference into the detailed description hereof.

FIELD OF INVENTION

This invention relates to methods and devices for carrying out ultrasound inspection, and for pipe inspections.

BACKGROUND

US App. Pub. 2011/0087444 to Volker (hereinafter the '444 publication) is directed to a "pig" for crawling through the bore of a pipe and performing ultrasound inspection of the inner pipe surface. The reference discloses an algorithm for imaging the pipe surface based on backscatter signals. The '444 publication involves Fermat's principle to determine sound paths with the shortest travel time. The modeling involves first building a grid and determining travel time for each point in the grid. The '444 reference requires scanning a pipe from the inside, where the primary information to be ascertained is 3D information about the inner surface of the pipe. This does not solve than the problem of accurately modeling the inner surface of a pipe using a scanning apparatus positioned on the outer surface.

U.S. Pat. No. 7,685,878 to Brandstrom (hereinafter the '878 patent) relates to a device for rotating a pair of ultrasound transducers around a pipe circumference for pipe weld inspection. It allows the cables and other apparatus extending away from the transducers to remain stationary, extending away in only a single direction. '878 teaches an apparatus which can be mounted on the pipe at the position adjacent the weld and which carries the transducers and rotates those transducers around the pipe, bearing in mind that effective access to the pipe is generally only available from one side of the pipe.

Two transducers are rotated around a circumferential location on a cylindrical body for structural testing of the body, carried on a mounting and drive apparatus including a magnetic attachment which can be manually brought up to a pipe from one side only for fixed connection to the pipe on that side at a position axially spaced from a weld. A collar shaped support for the pair of transducers is formed of a row of separate segments which wrap around the pipe from the one side and is rotated around the axis of the pipe to carry the transducer around the circumferential weld. The segments carry rollers to roll on the surface and are held against the pipe by magnets. The transducers are carried on the support in fixed angular position to track their position but in a manner which allows slight axial or radial movement relative to the pipe.

U.S. Pat. No. 7,412,890 to Johnson (hereinafter the '890 patent) relates to a method and apparatus for detecting cracks in pipe welds comprising flooding a volume adjacent to the outer pipe surface with water, then using phased array ultrasound to scan the pipe surface. The apparatus has a rectangular cavity that has its open bottom surface pressed against the pipe surface and is flooded with water. The ultrasound array is positioned at the top of the cavity. Phased-array data collection methods are used.

U.S. Pat. No. 5,515,298 to Bicz (hereinafter the '298 Patent) relates to an apparatus for performing ultrasound scanning of a fingerprint or other object placed on a concave surface. The apparatus projects ultrasound from an array of transducers through an array of pinholes (one per transducer) and against the concave interior of the surface on which the fingerprint rests. The transducers then derive characteristics of the fingerprint from the reflection and scattering of the spherical waveform produced by the pinhole. The apparatus appears to depend on the known structure of the convexo-concave lens structure of the support on which the fingerprint rests.

U.S. Pat. No. 6,896,171 to Den Boer et al (hereinafter the '171 Patent) relates to an apparatus for performing EMAT (electromagnetic acoustic transducer) scanning of a freshly-made pipe weld while still hot. The apparatus may include an array of EMAT transmitter and receiver coils positioned on a ring structure around the outer surface of the pipe. No post-processing algorithm details are disclosed. The apparatus is described as being able to detect the presence of weld defects, and gives some information as to their size, but neither images, precise locations, nor are any further details of defects discussed in the description.

US App. Pub. No. 2009/0158850 to Alleyne et al (hereinafter the '850 publication) relates to a method and apparatus for inspecting pipes wherein the pig apparatus is inserted into the bore of the pipe. Ultrasound transducers are pressed against the inner walls of the pipe and use guided waves (e.g. Lamb waves) of ultrasound within the material of the pipe wall itself to detect defects. Data collection and processing appears to be based on a full matrix capture technique from which different wave modes may be extracted, although a phased-array data collection technique may also be used.

US App. Pub. No. 2009/0078742 to Pasquali et al. (hereinafter the '742 publication) relates to a method and apparatus for inspecting multi-walled pipes, such as those used for undersea transport of hot or cold fluids. The method involves placing an ultrasound probe against the inner pipe surface and scanning at various intervals as the probe rotates around the inner circumference of the pipe wall. The apparatus is a probe positioned at the end of a rotatable arm, which positions the probe within the pipe and then rotates it about the circumference of the inner wall. The '742 publication also discloses methods of positioning the probe at various angles relative to the pipe surface. However, it appears to only teach the use of probes that are displaced from the weld in the pipe's axial direction, and are angled forward or backward toward the location of the pipe weld.

Additional prior art references include U.S. Pat. No. 7,762,136 to Ume, Ifeanyi C. et al., which teaches ultrasound systems and methods for measuring weld penetration depth in real time and off line, U.S. Pat. No. 7,694,569 to McGrath, Matthew et al. which teaches a phased array ultrasonic water wedge apparatus, U.S. Pat. No. 7,694,564 to Brignac, Jacques L. et al. which teaches a boiler tube inspection probe with centering mechanism and method of operating the same, U.S. Pat. No. 6,935,178 to Prause, Reinhard which teaches a device for inspecting pipes using ultrasound, U.S. Pat. No. 6,734,604 to Butler, John V. et al.

which teaches a multimode synthesized beam transduction apparatus, U.S. Pat. No. 4,872,130 to Pagano, Dominick A., which teaches an automated in-line pipe inspection system JP 2004028937 to Furukawa, T. et al., which teaches a method for measuring the shape of a welded pipe.

SUMMARY OF THE INVENTION

Example embodiments described in this document relate to methods and devices for performing ultrasound inspection of objects using full matrix data capture techniques. In a first aspect, the application is directed to a device for performing ultrasound scanning of a conduit, comprising a cuff adapted to fit around a circumference of the conduit, a carrier mounted slidably on the cuff and adapted to traverse the circumference of the conduit, an ultrasound probe mounted on the carrier and positioned to scan the circumference of the conduit as the carrier traverses the circumference of the conduit, a carrier motor mounted on the cuff or the carrier and used to drive the movement of the carrier about the circumference of the object, and one or more data connections providing control information for the carrier motor and the ultrasound probe and receiving scanning data from the ultrasound probe.

In another aspect, the cuff forms a liquid-resistant seal around the circumference of the conduit, and the device further comprises a liquid feed for receiving a liquid scanning medium and filling the volume defined between the interior of the cuff and the exterior of the conduit with the liquid scanning medium.

In a further aspect, the device further comprises a power connection for receiving electrical power for the carrier motor.

In a further aspect, the cuff is configurable between an open configuration allowing it to be fitted around the conduit and a closed configuration encircling the conduit.

In a further aspect, the device further comprises an adjustable reflector mounted to the carrier and a reflector motor for controlling an angle of the adjustable reflector in a plane substantially normal to a longitudinal axis of the object, wherein the ultrasound probe is positioned to scan the object via reflection of ultrasound signals off of the adjustable reflector, and the one or more data connections provide control information for the reflector motor.

In a further aspect, the device further comprises a power connection for receiving electrical power for the reflector motor.

In a further aspect, the conduit is a cylinder.

In a further aspect, the ultrasound probe is an array of ultrasound transceivers.

In a further aspect, the cuff comprises a knuckle which releasably secures a first half of said cuff to a second half of said cuff.

In a further aspect, the cuff comprises a first half of said cuff detachable from a second half of said cuff.

In a further aspect, the application is directed to a method for performing ultrasound scanning of a conduit, comprising providing an ultrasound array having a plurality of ultrasound elements arrayed substantially parallel to a longitudinal axis of the conduit, positioning the ultrasound array to project ultrasound signals toward an external surface of the object at a first point about the circumference of the conduit, performing a full-matrix-capture scan of the first point about the circumference of the conduit, comprising: transmitting an ultrasound signal from a first ultrasound element in the ultrasound array; sensing and recording ultrasound signals received by each other ultrasound element in the ultrasound array; and repeating the steps of transmitting, sensing and recording, wherein the step of transmitting is performed in turn by each ultrasound element in the ultrasound array other than the first ultrasound element; repositioning the ultrasound array at a second point about the circumference of the conduit, performing a full-matrix-capture scan of the second point about the circumference of the conduit, and repeating the steps of repositioning and performing a full-matrix-capture scan.

In a further aspect, the method further comprises, before performing each full-matrix-capture scan, transmitting at least one ultrasound signal from at least one ultrasound element in the ultrasound array, sensing at least one ultrasound signal received by at least one ultrasound element in the ultrasound array, evaluating at a processor the quality of the at least one sensed signal, and adjusting a scanning angle of the ultrasound array based on the outcome of the evaluation.

In a further aspect, the ultrasound array projects ultrasound signals toward the external surface of the object by reflecting the ultrasound signals off of an adjustable reflector, and adjusting the scanning angle of the ultrasound array comprises adjusting the angle of the adjustable reflector.

In a further aspect, the application is directed to a method of modeling the near and far surfaces of an object within a scanning plane passing through the near and far surfaces of the object, comprising providing a set of full-matrix-capture ultrasound scanning data corresponding to a scanning area within the scanning plane, the full-matrix-capture ultrasound scanning data captured using an ultrasound array transmitting and sensing ultrasound signals through a scanning medium situated between the ultrasound array and the near surface of the object and performing the steps of: transmitting an ultrasound signal from a first ultrasound element in the ultrasound array; sensing and recording ultrasound signals received by each other ultrasound element in the ultrasound array; and repeating the steps of transmitting, sensing and recording, wherein the step of transmitting is performed by each ultrasound element in the ultrasound array other than the first ultrasound element; constructing a first intensity map of the scanning area, comprising a plurality of points within the scanning area having associated intensity values, by calculating travel times of ultrasound signals through the scanning medium based on the full-matrix-capture ultrasound scanning data; filtering the first intensity map to model the boundary of the near surface within the scanning area; using the modeled boundary of the near surface as a lens in constructing a second intensity map, comprising a plurality of points within the scanning area having associated intensity values, by the application of Fermat's Principle, to compute ultrasound signal travel times through both the scanning medium and the object based on the full-matrix-capture ultrasound scanning data; and filtering the second intensity map to model the boundary of the far surface within the scanning area.

In a further aspect, constructing a first intensity map of the scanning area comprises calculating an intensity I at a plurality of points r within the scanning area where I is defined as the sum of the amplitude of the data-set of analytic time-domain signals from ultrasound array transmitter element i to ultrasound array receiver element j at time t for all i and j, where t is defined for each i,j pair as being the time it takes for sound to travel through the scanning medium.

In a further aspect, constructing a first intensity map of the scanning area comprises calculating an intensity I at a plurality of points r within the scanning area defined by the equation I $$I(r, a) = \left|\sum\nolimits_{i,j \in a} I(r, a)\right| = \left|\sum\nolimits_{i,j \in a} I(r, a)\right| =$$

$$\left|\sum_{-} (i, j \in a) \Bigg( g_{-}(i)j(t = (|e_{-}((i)) - r| + |e_{-}j - r|/c)) \right.$$

$$\left| g_{(i)j}\left(t = \frac{|e_{(i)} - r| + |e_j - r|}{c}\right) \right| I(r, a) =$$

$$\left|\sum_{-} (i, j \in a) \Bigg( g_{-}(i)j(t = (|e_{-}((i)) - r| + |e_{-}j - r|/c) \right.$$

$$\left| g_{(i)j}\left(t = \frac{|e_{(i)} - r| + |e_j - r|}{c}\right) \right| I(r) =$$

$$\left|\sum\nolimits_{i,j} g_{(i)j}\left(t = \frac{|e_{(i)} - r| + |e_j - r|}{c}\right)\right|$$

wherein $g_{(i)j}(t)$ is the amplitude of the data-set of analytic time-domain signals from ultrasound array transmitter element i to ultrasound array receiver element j at time t, r is the vector defining point r relative to a coordinate origin, $e_{(i)}$ is a vector defining the position of ultrasound array transmitter element i relative to the coordinate origin, $e_j$ is a vector defining the position of ultrasound array receiver element j relative to the coordinate origin, and c is the speed of sound traveling through the scanning medium.

In a further aspect, constructing a first intensity map of the scanning area comprises calculating an intensity I at a plurality of points r within the scanning area, each point intensity being calculated at a plurality of apertures defined by a fixed plurality of ultrasound array elements and the highest intensity of point r calculated for a single aperture being used to represent the intensity of point r in the intensity map.

In a further aspect, constructing a first intensity map of the scanning area comprises calculating an intensity I at a plurality of points r within the scanning area defined by the equation I $$I(r, a) = \left|\sum\nolimits_{i,j \in a} I(r, a)\right| = \left|\sum\nolimits_{i,j \in a} I(r, a)\right| =$$

$$\left|\sum_{-} (i, j \in a) \Bigg( g_{-}(i)j(t = (|e_{-}((i)) - r| + |e_{-}j - r|/c)) \right.$$

$$\left| g_{(i)j}\left(t = \frac{|e_{(i)} - r| + |e_j - r|}{c}\right) \right| I(r, a) =$$

$$\left|\sum_{-} (i, j \in a) \Bigg( g_{-}(i)j(t = (|e_{-}((i)) - r| + |e_{-}j - r|/c) \right.$$

$$\left| g_{(i)j}\left(t = \frac{|e_{(i)} - r| + |e_j - r|}{c}\right) \right|$$

$$I(r) = \max_{a \in A}\{I(r, a)\}$$

wherein $$I(r, a) = \left|\sum\nolimits_{i,j} g_{(i)j}\left(t = \frac{|e_{(i)} - r| + |e_j - r|}{c}\right)\right|$$

and wherein $g_{(i)j}(t)$ is the amplitude of the data-set of analytic time-domain signals from ultrasound array transmitter element i to ultrasound array receiver element j at time t, r is the vector defining point r relative to a coordinate origin, $e_{(i)}$ is a vector defining the position of ultrasound array transmitter element i relative to the coordinate origin, $e_j$ is a vector defining the position of ultrasound array receiver element j relative to the coordinate origin, c is the speed of sound traveling through the scanning medium, a is an aperture defined by a fixed plurality of adjacent ultrasound elements in the ultrasound array, and A is a set comprising a plurality of such apertures.

In a further aspect, using the modeled boundary of the near surface as a lens in constructing a second intensity map comprises calculating an intensity I at a plurality of points r within the scanning area defined by the equation I $$I(r, a) = \left|\sum\nolimits_{i,j \in a} I(r, a)\right| = \left|\sum\nolimits_{i,j \in a} I(r, a)\right| =$$

$$\left|\sum_{-} (i, j \in a) \Bigg( g_{-}(i)j(t = (|e_{-}((i)) - r| + |e_{-}j - r|/c)) \right.$$

$$\left| g_{(i)j}\left(t = \frac{|e_{(i)} - r| + |e_j - r|}{c}\right) \right| I(r, a) =$$

$$\left|\sum_{-} (i, j \in a) \Bigg( g_{-}(i)j(t = (|e_{-}((i)) - r| + |e_{-}j - r|/c) \right.$$

$$\left| g_{(i)j}\left(t = \frac{|e_{(i)} - r| + |e_j - r|}{c}\right) \right|$$

$$I(r) = \max_{a \in A}\{I(r, a)\}$$

wherein $$I(r, a) = \left|\sum_{i,j \in a} \sum_{t' \in T^K_{ij}(r)} g_{(i)j}(t')\right|$$

and wherein $$T_{ir}^K(r) = \{t_{ir} + t_{jr} | t_{ir} \in T_{ir}^K, t_{jr} \in T_{jr}^K\}$$

and wherein $T_{ir}^K$ is the set of all first-order and multiple-order derivatives of the time it takes sound to travel from ultrasound array transmitter element i to a point K on the boundary of the near surface, $T_{jr}^K$ is the set of all first-order and multiple-order derivatives of the time it takes sound to travel from ultrasound array receiver element j to a point K on the boundary of the near surface, $g_{(i)j}(t)$ is the amplitude of the data-set of analytic time-domain signals from ultrasound array transmitter element i to ultrasound array receiver element j at time t, r is the vector defining point r relative to a coordinate origin, $e_{(i)}$ is a vector defining the position of ultrasound array transmitter element i relative to the coordinate origin, $e_j$ is a vector defining the position of ultrasound array receiver element j relative to the coordinate origin, c is the speed of sound traveling through the scanning medium, a is an aperture defined by a fixed plurality of adjacent ultrasound elements in the ultrasound array, and A is a set comprising a plurality of such apertures.

In a further aspect, the method further comprises, before constructing a first intensity map, filtering the full-matrix-capture ultrasound scanning data to remove noise.

In a further aspect, filtering the first intensity map comprises passing the intensity map through an edge-detection filter and using the output as a model of the boundary of the near surface within the scanning area, and filtering the second intensity map comprises passing the intensity map through an edge-detection filter and using the output as a model of the boundary of the far surface within the scanning area.

In a further aspect, filtering the first intensity map and filtering the second intensity map each further comprise dilation of the detected edges produced by the edge-detection filter.

In a further aspect, filtering the first intensity map and filtering the second intensity map each further comprise thinning the dilated edges.

In a further aspect, filtering the first intensity map and filtering the second intensity map each further comprise selecting a single component from each vertical slice of the intensity map and removing all other components in that slice in order to maximize the continuity and length of the remaining components.

In a further aspect, the application is directed to a method of modeling the near and far surfaces of an object, comprising applying the methods above to a plurality of sets of full-matrix-capture ultrasound scanning data corresponding to a plurality of scanning planes passing through the near and far surfaces of the object, and modeling the near and far surfaces of the object based on the modeled boundaries within each scanning plane and the relative locations of each scanning plane.

In a further aspect, the plurality of scanning planes are parallel to and adjacent to each other.

In a further aspect, the object is substantially cylindrical, and the plurality of scanning planes all pass through the longitudinal axis of the object.

In a further aspect, the application is directed to a device for performing ultrasound scanning of an object, comprising a body adapted to fit on the object; an ultrasound probe mounted on the body and positioned to scan the body; one or more data connections providing control information for the carrier motor and the ultrasound probe and receiving scanning data from the ultrasound probe; an adjustable reflector mounted to the carrier; and a reflector motor for controlling an angle of the adjustable reflector in a plane substantially normal to a longitudinal axis of the object, wherein: the ultrasound probe is positioned to scan the object via reflection of ultrasound signals off of the adjustable reflector; and the one or more data connections provide control information for the reflector motor.

In a further aspect, the body forms a liquid-resistant seal around the circumference of the object, and the device further comprises a liquid feed for receiving a liquid scanning medium and filling the volume defined between the interior of the body and the exterior of the object with the liquid scanning medium.

In a further aspect, the device further comprises a power connection for receiving electrical power for the carrier motor.

In a further aspect, the device further comprises a power connection for receiving electrical power for the reflector motor.

In a further aspect, the ultrasound probe is an array of ultrasound transceivers.

Other example embodiments of the present disclosure will be apparent to those of ordinary skill in the art from a review of the following detailed description in conjunction with the drawings.

BRIEF DESCRIPTION OF THE DRAWINGS

FIG. 26(a) is an example black-and-white image used in conjunction with FIG. 26(b) to illustrate the effect of canny edge detection;

FIG. 26(b) is a black-and-white image showing the effect of canny edge detection on FIG. 26(a);

FIG. 27(a) is an example black-and-white image used in conjunction with FIG. 27(b) to illustrate the effect of a thinning algorithm;

FIG. 27(b) is a black-and-white image showing the effect of a thinning algorithm on FIG. 27(a);

FIG. 28(a) is an example black-and-white image showing a junction;

FIG. 28(b) is an enlarged view of the junction of FIG. 28(a), showing the rectangular path traced around the junction to count light-dark cycles for junction detection;

FIG. 29 is a graph of an example A-scan time-domain signal showing the travel time from transmitter excitation to the leading edge of a received wave packet;

DESCRIPTION OF EXAMPLE EMBODIMENTS

Overview

Figure 1:
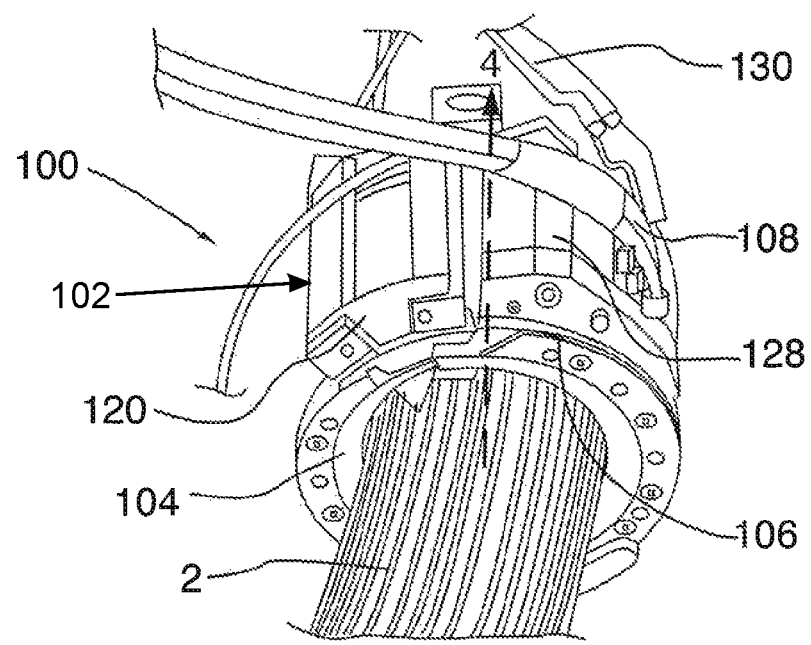
FIG. 1 is a perspective view of an ultrasound probe manipulator according to an example embodiment, operationally fitted to a pipe.

Example embodiments of the invention relate to ultrasound imaging devices and methods for capture and post-processing of ultrasound inspection data. In particular, the described example embodiments relate to devices and methods for inspecting pipe welds using a mechanical cuff that fits around a pipe in the weld region and rotates an ultrasound transceiver array around the circumference of the pipe as the array performs multiple transmit-receive cycles of the pipe volume via the Full Matrix Capture data acquisition technique. All data from the transmit-receive cycles is retained. The data is then post-processed using a two-step algorithm. First, the outer surface of the pipe is modeled by constructing an intensity map of the surface and filtering this map to detect the boundary of the outer surface. Second, the model of the outer surface constructed during the first step is used as a lens in modeling the inner surface of the pipe, using Fermat's principle. The inner surface is modeled the same way as the outer surface: an intensity map is built, then filtered to detect the boundary.

The mechanical cuff has a cylindrical outer structure having watertight seals on either end for sealing against a pipe surface. It receives a stream of water via a tube and fills the volume between the structure and the pipe surface with water while in operation in order to facilitate ultrasound scanning.

The cuff also has an inner rotating ring having on its inner surface a linear array of ultrasound transceiver crystals with the longitudinal axis of the array aligned along the length of the cylindrical structure, normal to the rotational direction of the inner ring around the circumference of the pipe. The inner ring is automatically rotated around the pipe surface in operation while the outer structure of the cuff remains stationary.

Data is acquired by rotating the inner ring around the circumference of the pipe while performing multiple transmit-receive cycles with the ultrasound array for each frame. Each frame uses the Full Matrix Capture technique: a single element is pulsed, with each element in the array measuring the response at that position and storing the resulting time-domain signal (A-scan). This process is then repeated, pulsing each element in turn and recording the response at each element, resulting in a total data corpus of (N×N) A-scans for an array having N elements. In this invention, the stored time period of each A-scan is determined by monitoring for a signal spike past a set threshold (at time t), then retroactively recording all signal data beginning at a set interval before the spike (at time t−C).

In situations where the cuff isn't perfectly normal to the pipe surface at all points around the circumference, it may be preferable to vary the angle of the array to the pipe surface. For this purpose, the inner ring structure incorporates an adjustable reflector or mirror for reflecting ultrasound waves between the transceiver array and the pipe surface at varying angles. The mirror may be adjusted automatically by a local or remote processor or controller module that receives probe data and automatically optimizes the signal quality by adjusting the mirror angle.

The post-processing algorithm may feature a number of refinements over the broad outline set out above. Multiple wave modes may be used to improve the reach and resolution of each probe. The outer surface may be modeled as multiple surfaces to further improve resolution of the inner surface where the outer surface is highly irregular. In addition, data from multiple adjacent "slices" of the pipe or other volume may be combined and overlaid to improve the continuity of the surface model, or data from two slices of the same area taken at different times may be overlaid to detect changes in the surfaces over time.

While the invention has been described as a pipe inspection tool and technique, the general principles and algorithms are applicable to ultrasound imaging in a number of different contexts and applications.

Ultrasound Probe Manipulator Device

With reference to the drawings, FIG. 1 shows an example embodiment comprising an ultrasound probe manipulator 100. The manipulator 100 comprises a cuff 106 that is fitted around the circumference of a pipe 2 during the scanning process. The center of the cuff 106 is aligned with the longitudinal axis 4 of the pipe 2. The manipulator 100 uses a linear array of ultrasound probe elements, mounted on a carrier (not shown) that traverses the circumference of the cuff 106 by means of a motor 128, to scan the slice of pipe encompassed by the cuff 106.

In operation, the cuff 106 is fitted around the pipe 2, with a watertight seal 104 extending from the cuff 106 to the pipe surface. The interior volume defined by the inner surface of the cuff 106, the seal 104, and the outer pipe surface is then filled with water or another fluid suitable for service as an ultrasound scanning medium. In some embodiments, the water is pumped into the interior volume by a hose 110 (shown in FIG. 6) incorporated into the manipulator 100. The hose 110 is connected to an external water source and/or pump, and feeds into the interior volume of the cuff 106 via a hose intake 132 (shown in FIG. 2).

One or more data connections connect the manipulator 100 to one or more external data processing systems and/or controllers. These external systems may control the operation of the manipulator 100 and/or collect and process the data gathered by the scanning operation of the manipulator 100. FIG. 1 shows a motor connector 130 used to supply power and control data to the motor 128 operative to drive the carrier 102 around the cuff 106. Probe data connectors 108 serve to communicate ultrasound probe control data and data collected by the probe between the probe array and the external data processing systems and/or controllers. In other embodiments, some or all of these functions may take place within the manipulator 100 itself, for example by means of an embedded controller and/or data storage and processing unit. In some embodiments, the motors used by the manipulator 100 may include their own power sources.

Figure 2:
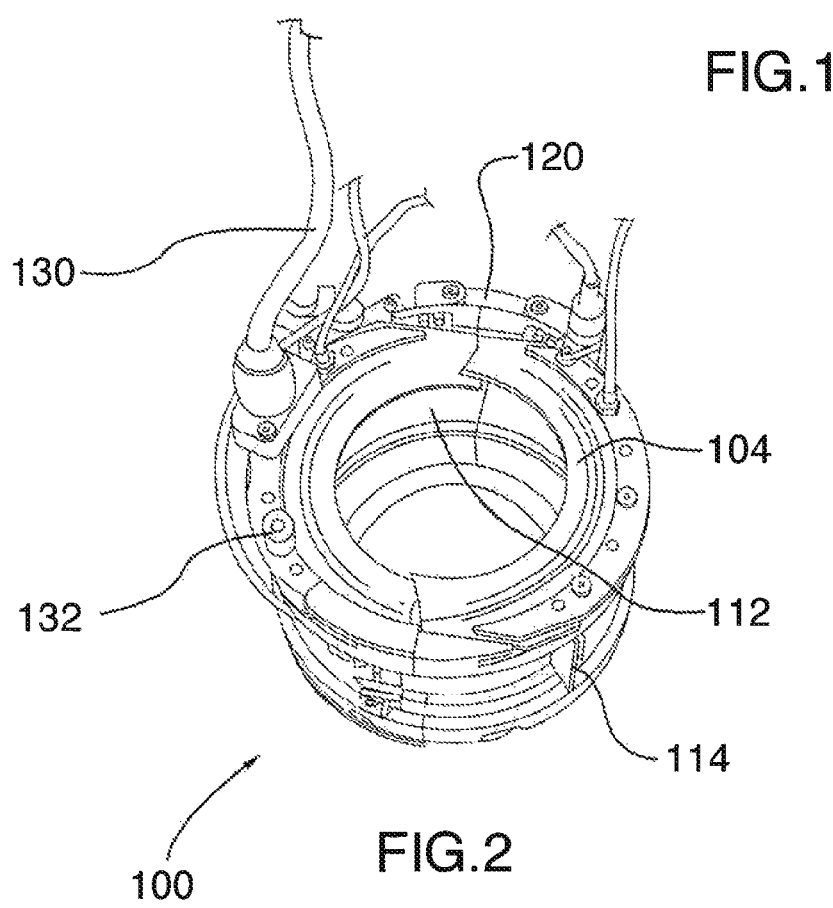
FIG. 2 is a perspective view of the example probe manipulator of FIG. 1.

FIG. 2 shows a similar embodiment to FIG. 1 in isolation instead of fitted to a pipe. The inner surface 112 of the cuff 106 is visible, as is the outer surface 114. The hose intake 132 is also visible in this figure.

Figure 3:
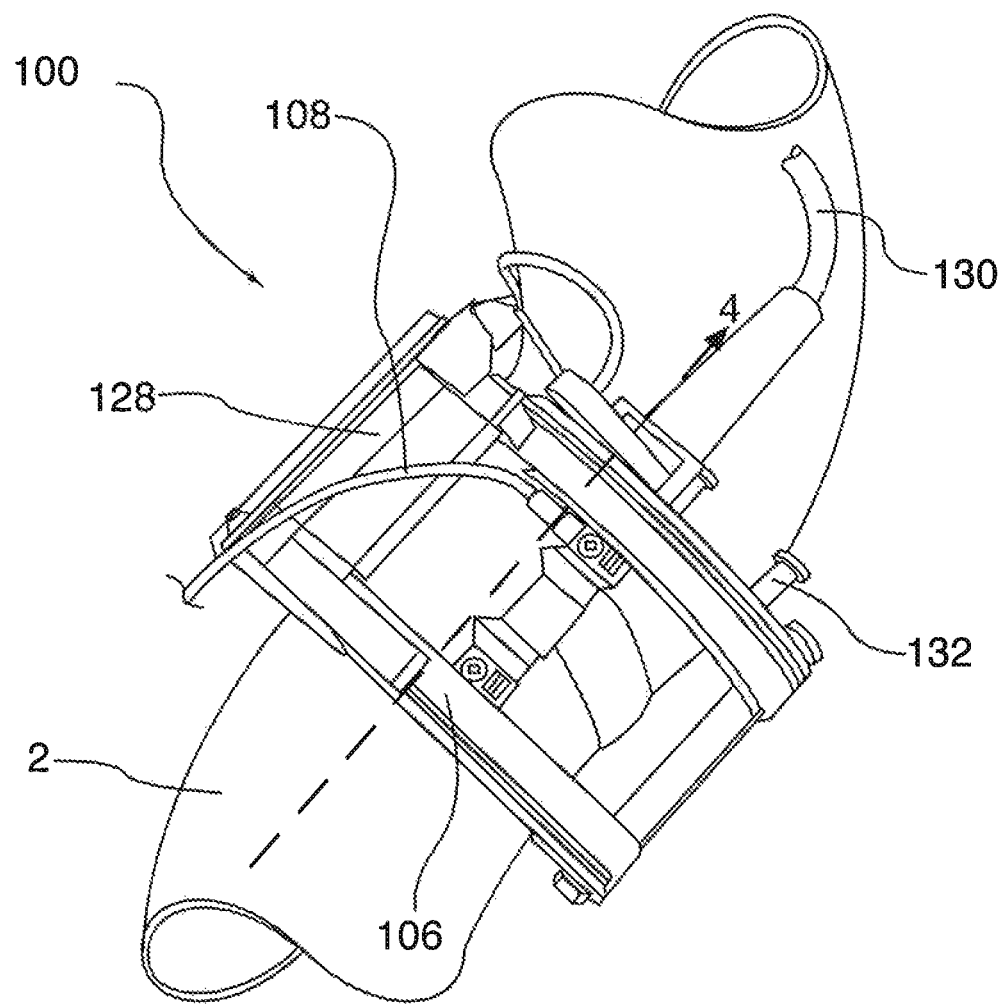
FIG. 3 is a side view of the example probe manipulator of FIG. 1 operationally fitted to a pipe.
Figure 4:
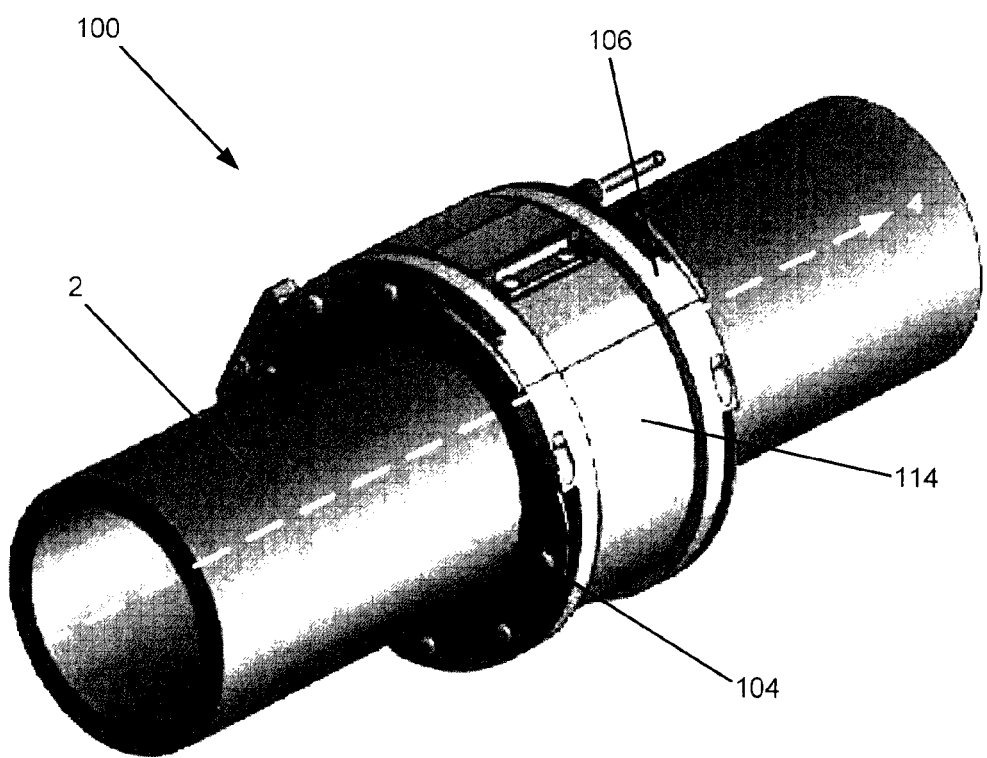
FIG. 4 is an isometric view of the example probe manipulator of FIG. 1 operationally fitted to a pipe.

FIG. 3 is a side view of the manipulator 100 fitted to a curved pipe, showing the longitudinal axis 4 of the pipe portion being scanned. FIG. 4 is an isometric view of the manipulator 100 fitted to a straight pipe, showing the longitudinal axis 4 of the pipe.

Figure 5:
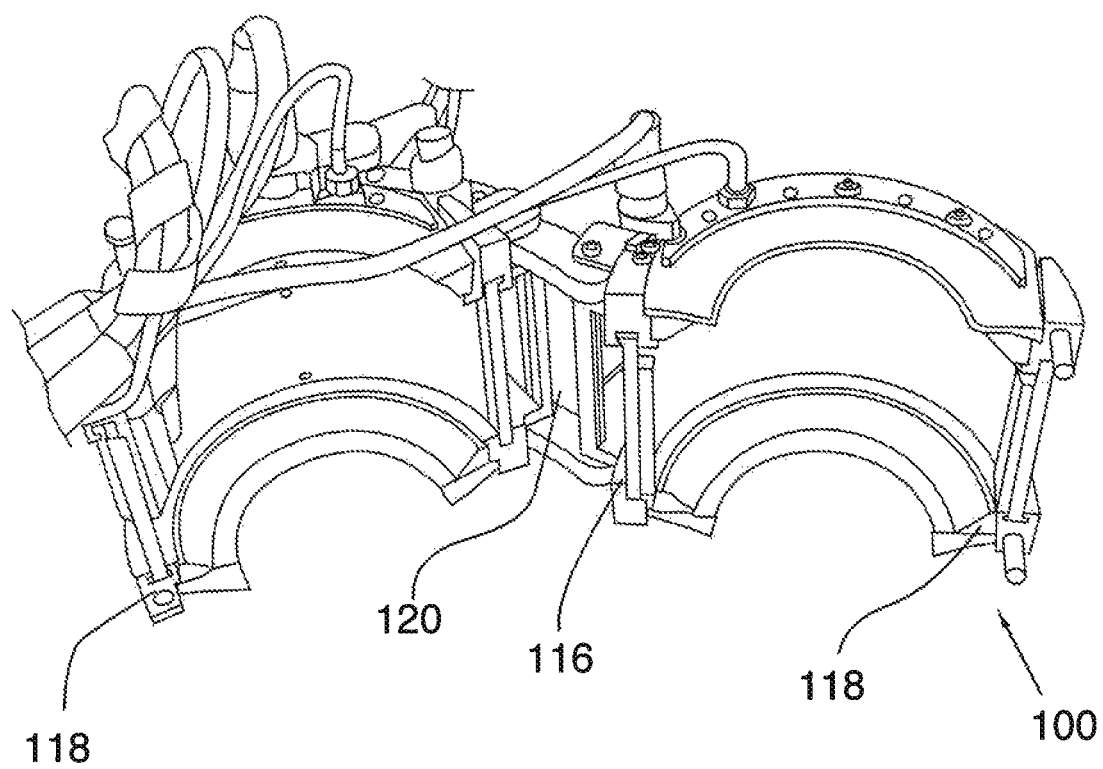
FIG. 5 is a perspective view of a hinged probe manipulator according to an example embodiment, showing the manipulator in an open configuration.
Figure 6:
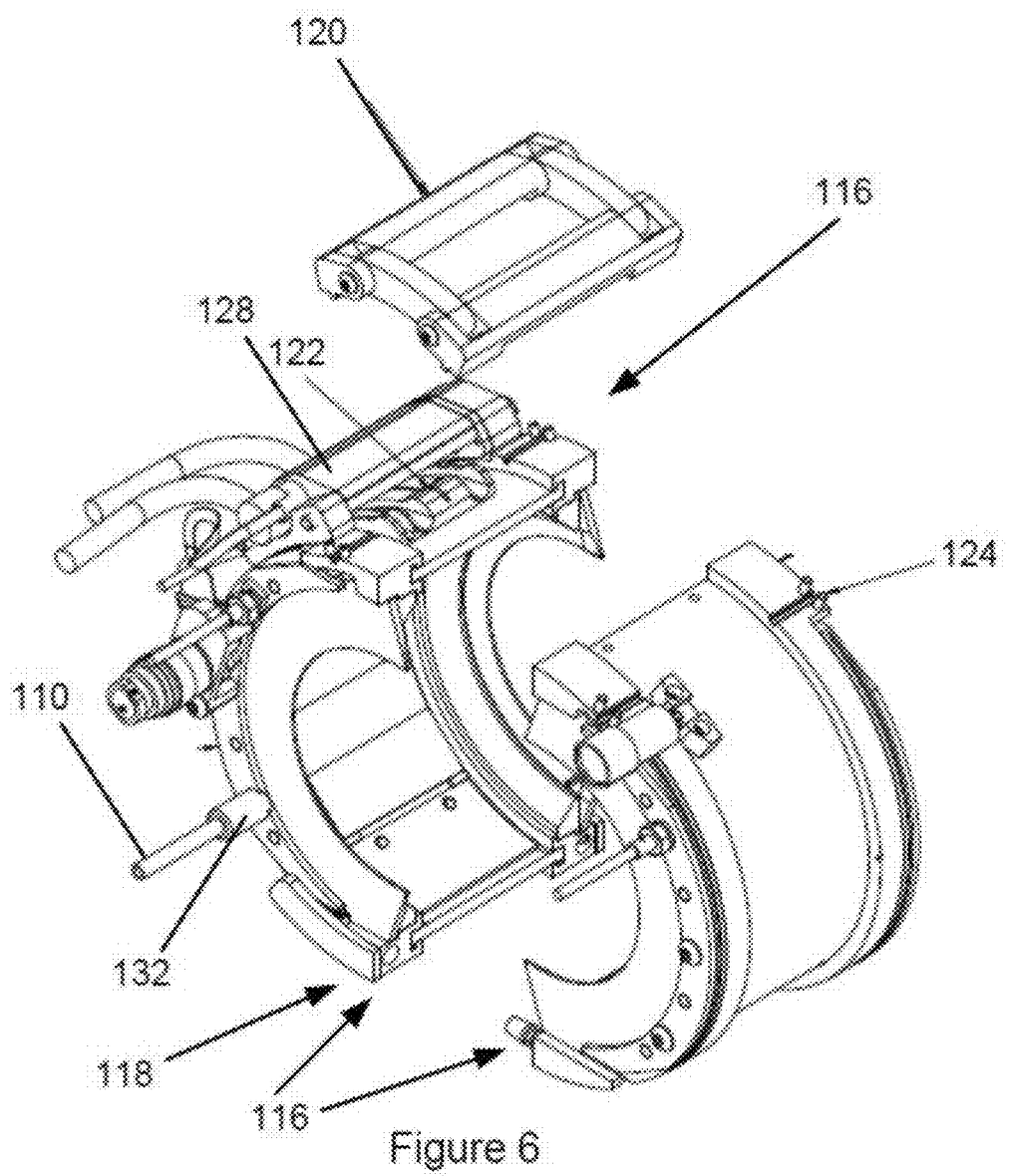
FIG. 6 is an isometric view of a hinged probe manipulator according to an example embodiment, showing the manipulator disassembled into two halves and a hinged knuckle.

The manipulator 100 may in some embodiments be fitted or removed from a pipe or other scanning subject by means of a hinged design that allows the cuff 106 to be opened. FIG. 5 shows an example embodiment comprising a hinged manipulator, with a hinged portion 116 allowing the cuff to be opened, and a coupling portion 118 allowing the ends of the cuff to be coupled together into the closed operational position by coupling means such as a latch. FIG. 6 shows the structure of the hinged portion 116, which uses a hinged knuckle 120 to create a double hinge between the two halves of the cuff 106 rather than a simple, single-hinged clamshell design. The hinged knuckle 120 attached to a first half of the cuff 106 at a first connecting point 122, and to the second half of the cuff 106 at a second connecting point 124. Use of a double hinge allows the manipulator 100 to be more easily placed around a pipe circumference due to the greater degrees of freedom afforded. The coupling portion 118 is shown in the example embodiment of FIG. 6 as a latch 128.

Figure 7:
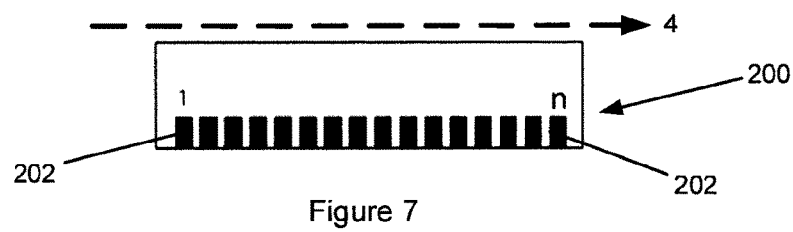
FIG. 7 is a side view of a linear multi-element ultrasound probe array.

In operation, the manipulator 100 uses a linear array of ultrasound probe elements, such as resonator crystals, to scan the volume encompassed by the cuff 106. FIG. 7 shows an example linear ultrasound probe array 200 having n elements 202. In operation, the linear array 200 attached to the carrier 102 is aligned parallel to the longitudinal axis 4 of the pipe 2 being scanned. The pipe 2 is scanned by the full array 200 using the Full Matrix Capture technique described below, then the carrier is moved about the circumference of the pipe 2 by a motor included in the manipulator 100, after which the scanning process is repeated for the new circumferential coordinates of the carrier's new position. By performing a number of such scans at regularly-spaced intervals about the circumference of the pipe slice encompassed by the cuff 106, a model of the entire pipe circumference can be built using the scan data.

Full Matrix Capture (FMC) Data Collection

Figure 8:
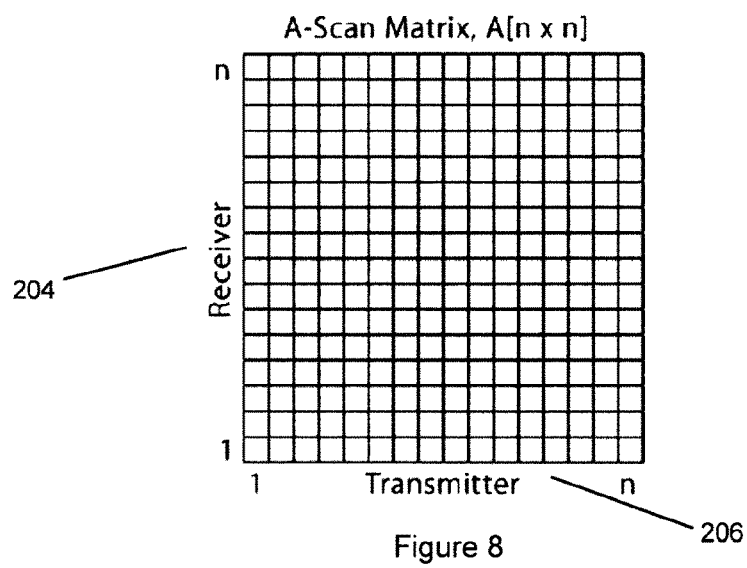
FIG. 8 is a diagram of an N by N matrix of ultrasound scan data generated by the Full Matrix Capture technique using an N-element ultrasound probe array.

The Full Matrix Capture (FMC) technique used in some embodiments is a known refinement of the phased-array data capture technique widely used for ultrasound scanning FMC generally requires capturing a larger volume of data than a comparable phased-array scan, but allows more information to be extracted from a single scan. In Full Matrix Capture, a single element 202 of the ultrasound array 200 is pulsed, transmitting ultrasound energy into the medium being scanned. Each 202 element of the array 200 is used as a receiver for this energy, detecting ultrasound vibrations at its coordinates over the time period following this pulse. This detected vibration is recorded and stored for post-processing. Once the data has been recorded for all n elements 202, a second element 202 is pulsed, and the recording process is repeated for all receiving elements 202. This process then repeats again, with each of the n elements 202 being pulsed in turn and data recorded for each receiving element 202, resulting in an n by n matrix of recorded data: each receiving element 202 records scan data from the pulse from each transmitting element 202. This matrix is illustrated by FIG. 8, showing a matrix of n transmitting elements 206 by n receiving elements 204.

Figure 9:
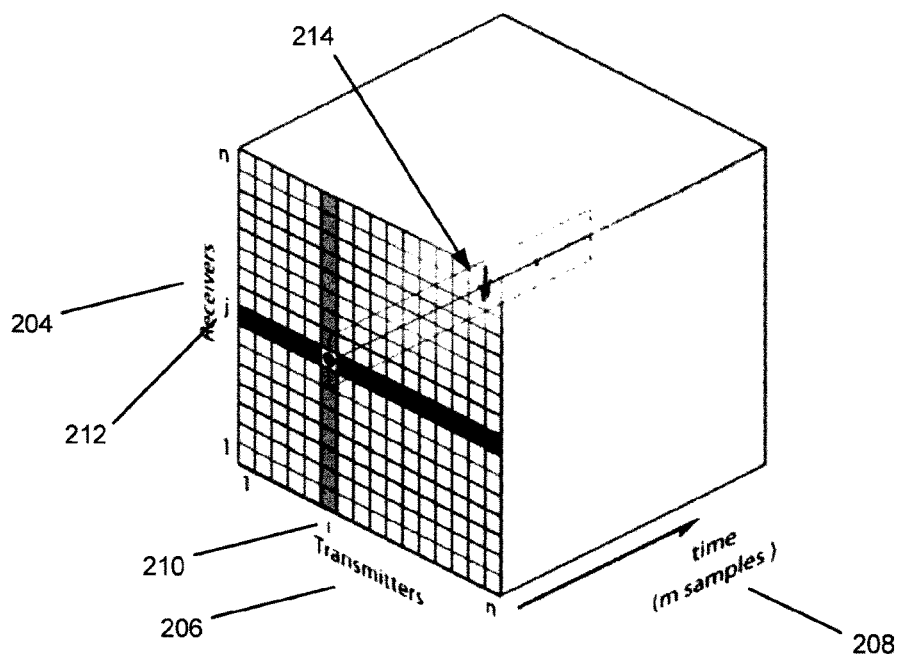
FIG. 9 is an isometric representation of an N by N by M matrix of A-scan data as in FIG. 8, showing the third dimension of M samples recorded over time for each A-scan.

In some embodiments, the data from each receiving element 202 is recorded as a series of digital samples taken over time. FIG. 9 shows a three-dimensional matrix of such scan data from a single transmit-receive cycle as described above. The data signal 214 resulting from the pulse of transmitter i 210 captured by receiver j 212 is shown as a series of m samples taken over the time dimension 208, resulting in a total three-dimensional matrix of samples n by n by m in size.

In an example embodiment using the manipulator 100 of FIGS. 1 to 6, the movement of the carrier 102 and the operation of the ultrasound array 200 is controlled by an external controller connected to the manipulator 100 by the data connections 108. Data recorded by the array 200 is sent to an external data recorder and processor via the data connections 108, where it is stored and processed as further described below. The controller and data processor may also be in communication with each other, and the recorded data may be used by the controller to calibrate or optimize the operation of the carrier 102 and/or array 200 during scanning.

Figure 68:
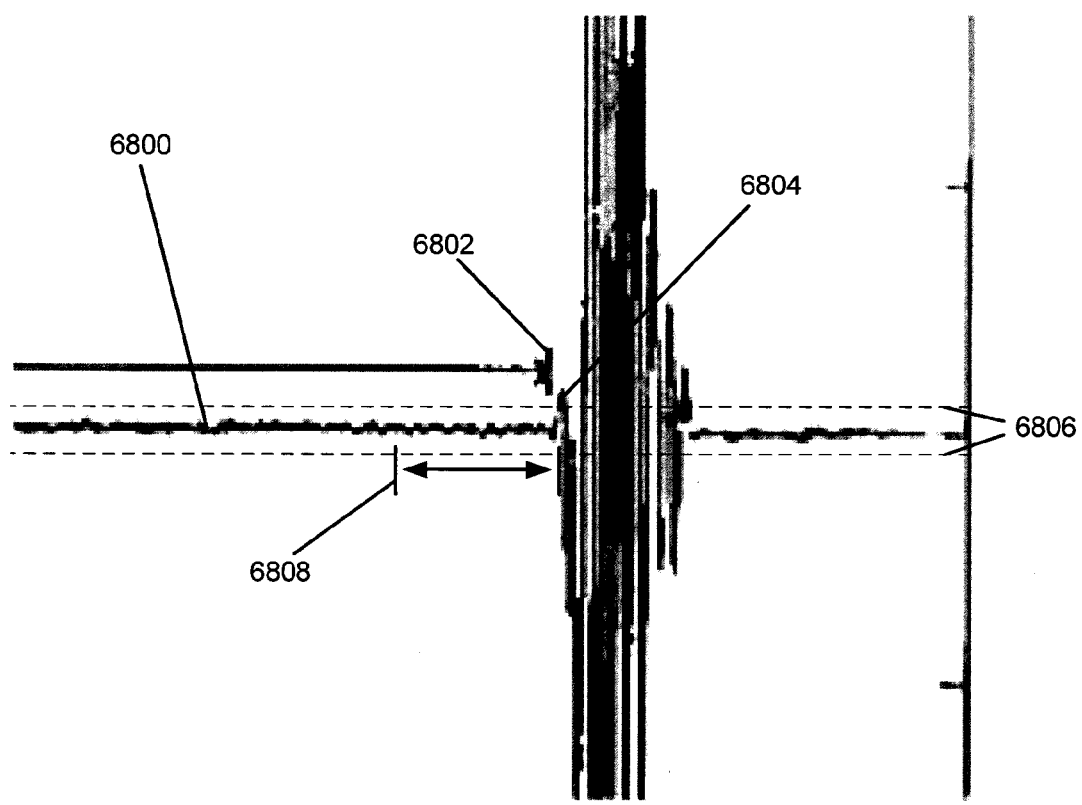
FIG. 68 is a detail view of the samples of interest in a time-domain ultrasound signal showing the time period during which data samples are to be retained according to an example embodiment.

A single transmit-receive cycle as described above results in n times n A-scans (i.e., time-domain signals received at a receiving element 202). A single A-scan is generally created by a receiving element by monitoring for vibrations above a set threshold, then recording sensed vibrations and for a set period of time after this threshold is crossed. In some embodiments, a buffer is used to store the sensed data prior to recording, and the recording period is set to include buffered data for a predetermined period before the threshold is crossed, thereby capturing a period beginning shortly before the threshold is crossed and lasting for a set period of time. FIG. 68 shows an illustration of this process. The sensed data 6800 is sampled until a peak 6804 is detected that exceeds a predetermined threshold 6806, thereby signalling the beginning of the period of interest of the signal. However, there may exist data of interest prior to the peak 6804, such as the initial oscillations of the signal 6800 beginning at point 6802. In order to capture these initial data points that precede the peak 6804, buffered data points are retained extending back for a predetermined period before the peak 6804, such as back to an earlier point 6808 which is early enough to capture any initial signal perturbations of interest.

Processing of FMC Data

Processing of the captured data may be done concurrently with the scan or afterward. Techniques for processing the captured data are described below in accordance with example embodiments. These techniques may involve application of the Shifting Aperture Focusing Method (SFM), the Interior Focus Method (IFM), and boundary detection and recognition to determine the structure of a scanned object, such as the inner and outer surface contours of a pipe wall. These techniques may allow the detection of subtle variations in pipe thickness, defects in pipe walls, and other structural details of arbitrary inner and outer surfaces of a pipe. Some of the mathematical principles applied by various embodiments are hereby described to more fully explain their operation.

Figure 17:
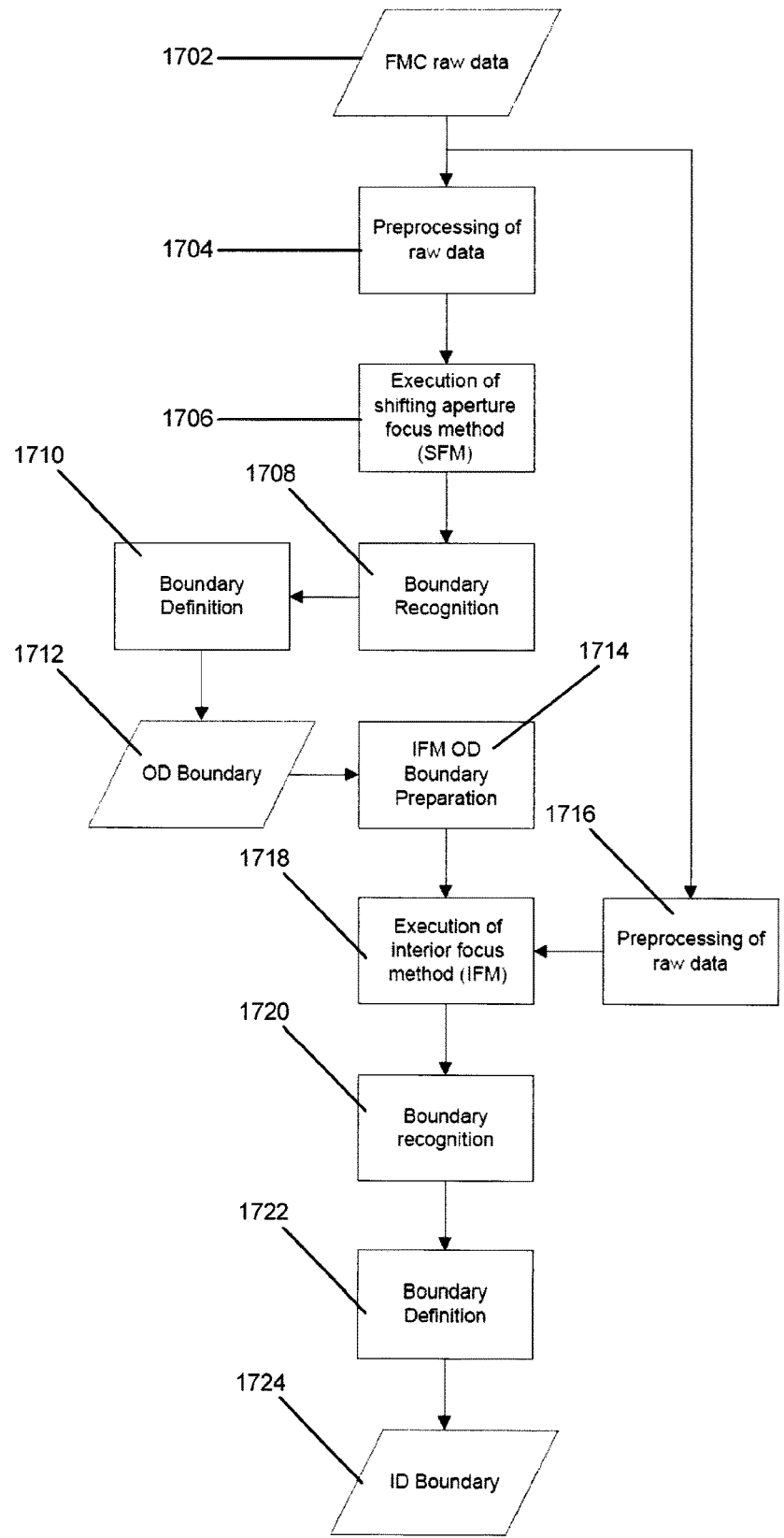
FIG. 17 is a flow chart showing the steps carried out in modeling of outer and inner surfaces of a scanned object according to an example embodiment.

FIG. 17 is a flowchart showing the operations involved in modeling the outer diameter (OD) and inner diameter (ID) surfaces of a scanned portion of a pipe wall or other object according to an example embodiment. The Full Matrix Capture (FMC) data from a transmit-receive cycle of the probe array 200 is collected at step 1702. At step 1704, the raw FMC data is pre-processed. The OD boundary is modeled in steps 1706 through 1710, then this OD boundary definition 1712 is used to determine the ID boundary 1724 in conjunction with the raw FMC data in steps 1716 through 1722. These steps are described more fully below. In some embodiments, the raw FMC data used includes data from multiple transmit-receive cycles, which is used to improve the modeling of adjacent radial positions of the pipe wall.

Figure 10:
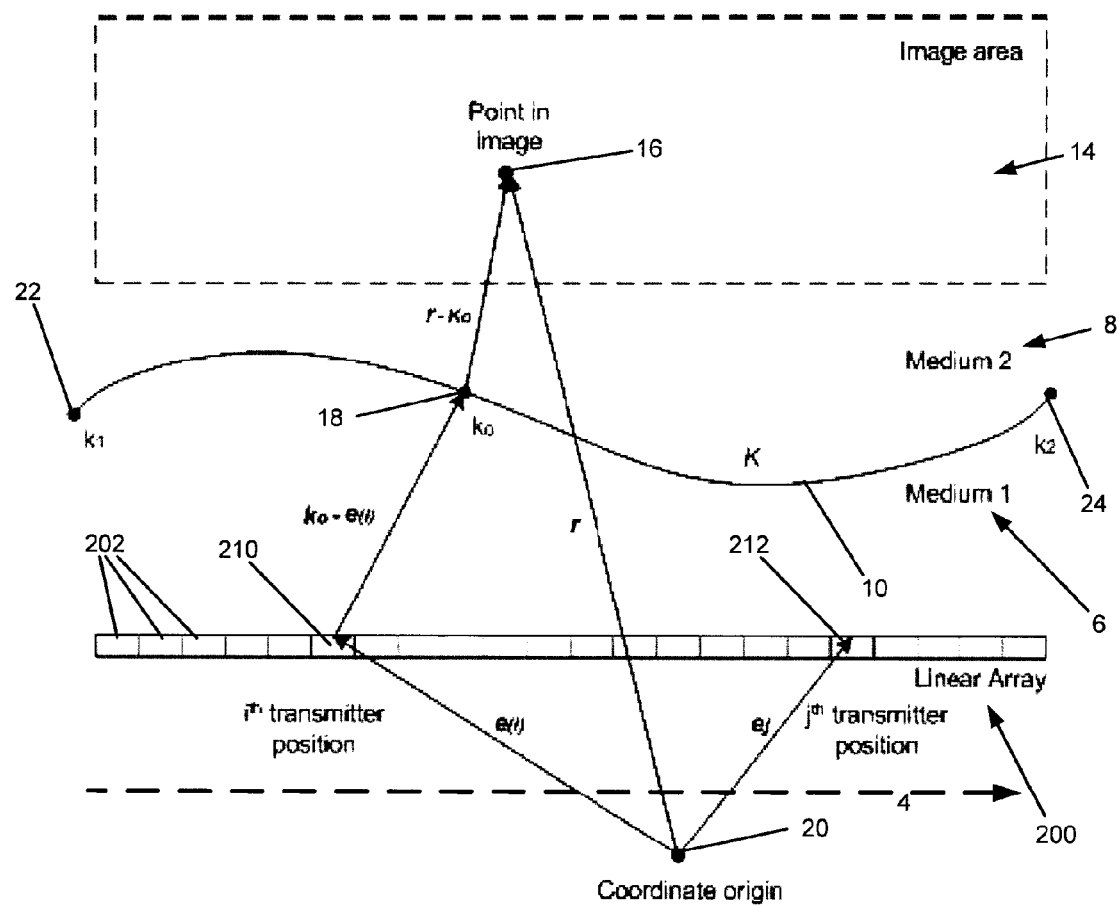
FIG. 10 is a side view of a linear ultrasound probe array scanning a volume through an intermediate medium.

FIG. 10 shows the vector notation used in describing the processing of A-scan data. The figure depicts a plane defined by the linear ultrasound array 200 and the longitudinal axis 4 of the pipe 2 being scanned. The area of the plane being scanned in this example is shown by image area 14.

k is a vector valued function such that k(u)=<x,y>=<f(u), g(u)> is a vector in 2-space, R2, where u∈[u1,u2]. The point k(u) is defined as k(u)=(x,y)=(f(u),g(u)). The vector k(u), represented in boldface, is referred to distinctly from the point k(u). Throughout this description, for any vector v=<x,y>, the point (x,y) is denoted by v, in italics and not boldface.

K 10 is the curve defined by the set of all points k(u), u∈[u$_1$,u$_2$]. K is piecewise-smooth and non self-intersecting. The endpoints of K are k(u$_1$) and k(u$_2$) which are denoted k$_1$ 22 and k$_2$ 24 respectively.

K separates a first medium 6 from a second medium 8 where ultrasound probe element i 210 lies in the first medium 6 and the endpoint of vector r 16 lies in the second medium 8. For example, when scanning a pipe circumference, the first medium 6 would be composed of water pumped into the interior volume between the cuff 106 and the outer surface of the pipe 2, while the second medium 8 would be the metal of the pipe wall itself. The speed of sound in the first medium 6 and the second medium 8 are denoted as c1 and c2 respectively.

With reference again to FIG. 10, the figure shows vector k$_o$, defined by ko=k(uo)=<f(uo),g(uo)>, where the point ko∈K (point k$_o$ being denoted by numeral 18, surface K by numeral 10). Also, ultrasound element i 210 is shown with position vector e(i) from coordinate origin 20. The travel time from ultrasound element i 210 to r 16 through ko 18, denoted by $t_{ir}^{ko}$, is given by the following equation:

$$t_{ir}^{k_0} = \frac{|k_0 - e_{(i)}|}{c_1} + \frac{|r - k_{(0)}|}{c_2} \quad \text{(Equation 1)}$$

Figure 11:
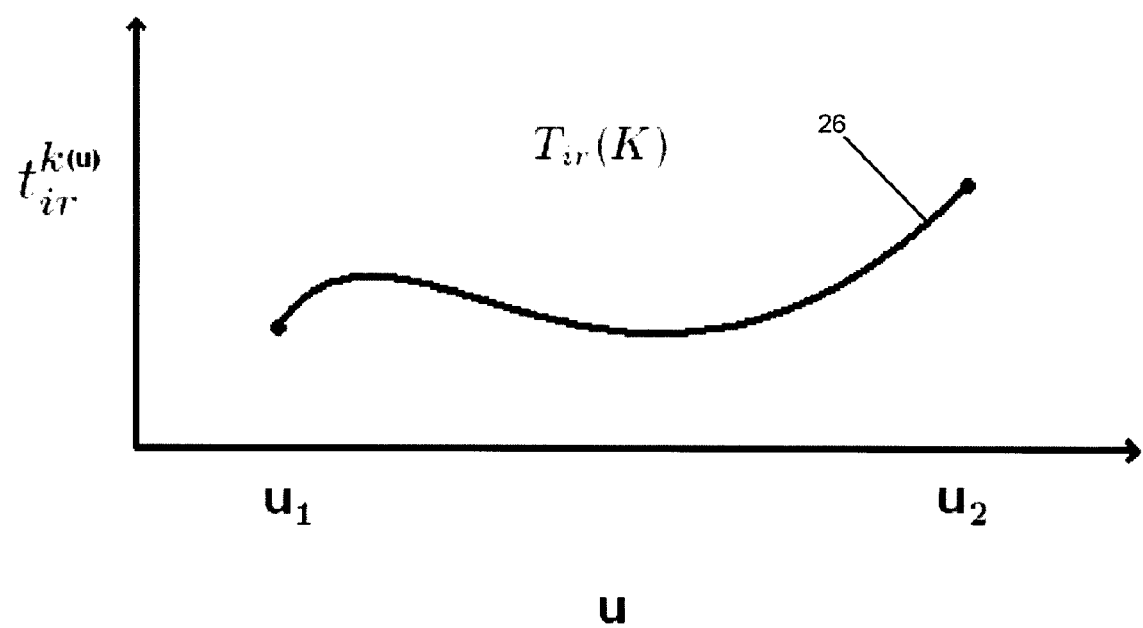
FIG. 11 is a graph of the curve $T_{ir}(K)$ from point $u_1$ to $u_2$ on the surface of the object being scanned.

The travel time from r 16 to i 210 through k$_o$ 18 (denoted) $t_{ri}^{ko}$ is equal to $t_{ir}^{ko}$. The times from i 210 to r 16 through all k∈K, k varying parametrically from k$_1$ to k$_2$, are given by the curve, T$_{ir}$(K) 26, illustrated in FIG. 11.

Physical Considerations

Speed of Sound Variation—Material Physical Considerations

Figure 72:
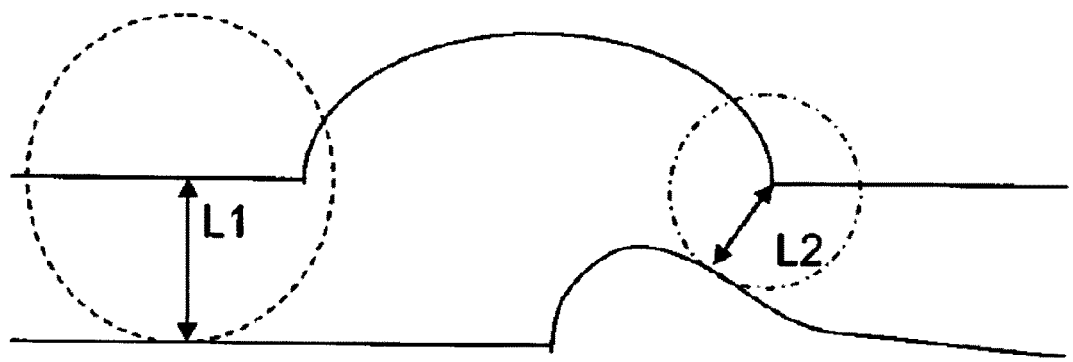
FIG. 72 is a side cross-sectional view through an example pipe weld showing example definitions of thickness.

In ultrasonic applications, absolute distance measurements may be directly calculated from the travel times of acoustic pulses, and hence may be sensitive to the speed of ultrasonic sound in the materials under study. In some embodiments described below pertaining to pipe weld inspection, thickness is defined as the shortest distance from a point on the outer surface to the inner surface. FIG. 72 illustrates this definition of wall thickness. L1 and L2 are the thicknesses at two different locations on the outer surface of a feeder weld. The inner and outer surface profiles are essential pieces of information used to determine the wall thickness with respect to any location on the outer or inner surface.

The ultrasonic distance measurement is determined by the sound velocity of the material and the time taken for a sound wave to travel between start and end points. A distance measurement L can be written as L=∇τ where τ is the time taken by the wave to travel from start and end points. ∇ is the average sound velocity along the path. Since the outer surface profile may be measured using immersion techniques and water may be used as a couplant in some embodiments, the sound velocity of water would need to be considered, as it would affect the distant measurement accuracy.

Water Sound Velocity Temperature Dependency

The sound velocity of water as a function of its temperature is V$_{fw}$(T)=1405.03+4.624 T−0.0383 T$^2$ where V denotes the fresh water sound velocity in meters per second unit and T denotes the temperature in degrees Celsius.

Element Directivity (Beam Spread—Lateral and Transverse)

Element directivity is a potentially important factor in the design of the probe array. Generally speaking, element directivity can be thought of as the variance of the amplitude pressure field across different points on the inspection volume. Both the Cartesian (x-y-z) and spherical (φ-θ-r) coordinates are standard when discussing directivity (see FIG. 73). Convenience dictates that the Cartesian coordinates are of use when discussing near field element directivity while spherical coordinates are of use when discussing far field directivity. In the far field, for a rectangular element with L much longer than a, and for a given distance, r, the directivity in the x-z plane is well approximated via a function of only θ, excitation frequency f, and a.

Element directivity is ultimately derived from the wave equation, given by the following:

$$\frac{\partial^2 p}{\partial x^2} + \frac{\partial^2 p}{\partial y^2} + \frac{\partial^2 p}{\partial z^2} - \frac{1}{c^2}\frac{\partial^2 p}{\partial t^2} = 0$$

where p is pressure and t is time.

The pressure field at a given point in an inspection volume can be derived numerically. A transducer can be treated as a piston radiating sound waves in water where the transducer generates an infinite number of plane waves, all traveling in the positive z-direction but with different x and y component directions. As such, the pressure field at a point q=(x; y; z) is represented in the form of a 2D integral given by:

$$p(q, \omega) = \left(\frac{1}{2\pi}\right)^2 \int_{-\infty}^{\infty}\int_{-\infty}^{\infty} P(k_x, k_y) e^{i(k_x x + k_y y + k_z z)} dk_x dk_y$$

where $\bar{k}=(k_x,k_y,k_z)$ is the wave vector with magnitude $$k = \frac{2\pi}{\lambda}.$$

After some derivation, a solution to the above equation for a rectangular element with length $l_x$ in the x direction and length $l_y$ in they direction can be derived where:

$$p(q, \omega) = \left(\frac{1}{2\pi}\right)^2 \int\int_{k_x^2+k_y^2 \leq k^2} \frac{i\omega\rho V(k_x, k_y)}{ik_2} e^{i(k_x x + k_y y + k_z z)} dk_x dk_y$$

where $V(k_x,k_y)$ is the 2D spatial Fourier transform of the velocity of the field of the transducer:

$$V(k_x,k_y) = \int_{-\infty}^{\infty}\int_{-\infty}^{\infty} v_x(x,y,z=0,\omega) e^{-i(k_x x + k_y y)} dx dy$$

Far Field Directivity

In the far field of an element (when the ultrasound transducer element dimension is very small with respect to inspection distance), for a given radius r in the x-z plane, the directivity can be well approximated by a function varying only in θ, element width a, and frequency f, when the transducer length L is much bigger than its width, a. Far field directivity may be relevant in some embodiments involving weld inspection because the weld will often be in the far field (in the axial direction, x-z plane) of the ultrasound array transducer elements. The formula for far field directivity of the element in the x-z plane is given below:

$$D_F(f, \theta) = sinc\left(\frac{\pi a f \sin\theta}{c}\right)$$

Figure 74:
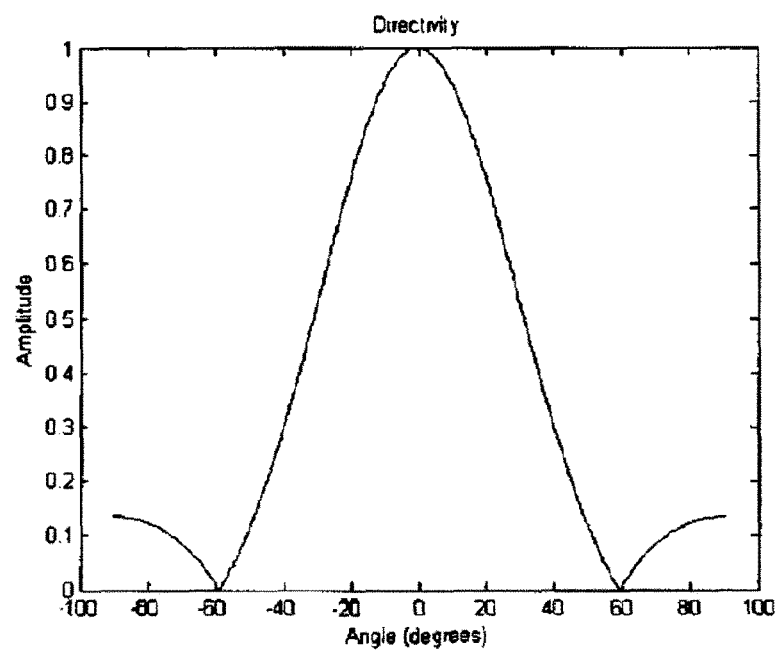
FIG. 74 is a graph of ultrasound beam directivity showing amplitude increasing from 0 to 1 on the vertical axis and angle from −90 degrees to 90 degrees on the horizontal axis for an example embodiment having a=0.23 mm, f=7.5 MHz, and c=1480 m/s.

It is worth noting that both a and f increase directivity at a given angle θ. FIG. 74 illustrates directivity in an example embodiment having θ=−90 degrees to 90 degrees, a=0.23 mm, f=7.5 MHz, and c=1480 m/s.

Element Width

Figure 75:
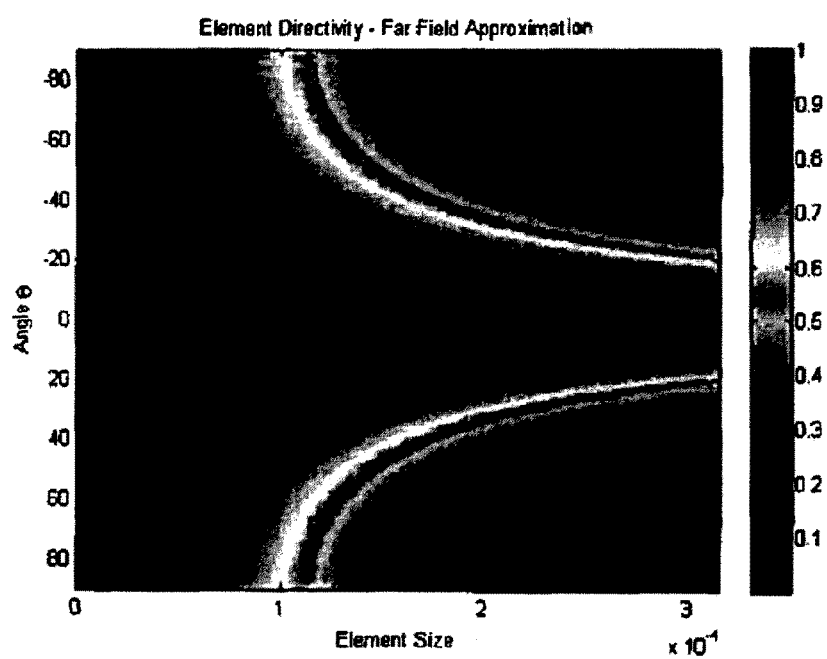
FIG. 75 is a spectral graph of element directivity showing angle decreasing from 90 to −90 on the vertical axis and ultrasound transducer element size increasing from 0 mm to 0.3 mm on the horizontal axis, and having a legend for colour values on the right side of the figure ranging from amplitude 0 to amplitude 1.

Element width a dictates element directivity as is illustrated in the equation above. Smaller element widths will radiate sound omnidirectionally (in all directions). Larger element widths will focus sound in the direction of their surface normals. This is illustrated by FIG. 75, which shows element directivity as a function of element size a.

Analogously, with respect to focusing arrays, arrays with larger element widths will generally focus better than arrays with smaller widths in the direction of the array normal. The direction of the array normal corresponds to a steering angle of zero. On the other hand, arrays with smaller element widths will generally focus better (than arrays with larger element widths) in directions away from the array surface normal.

Figure 76A:
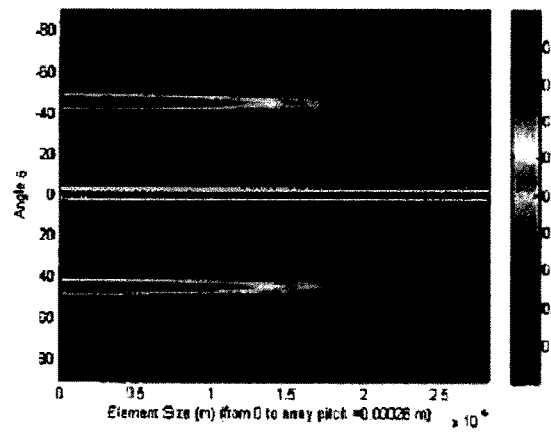
FIG. 76(a) is a graph of array directivity where the steering angle $\theta_s$ equals 0 degrees, showing angle $\theta$ decreasing along the vertical axis from 90 degrees to −90 degrees and element size increasing from 0 mm to 0.28 mm along the horizontal axis, and having a legend for colour values on the right side of the figure ranging from amplitude 0 to amplitude 1.
Figure 76B:
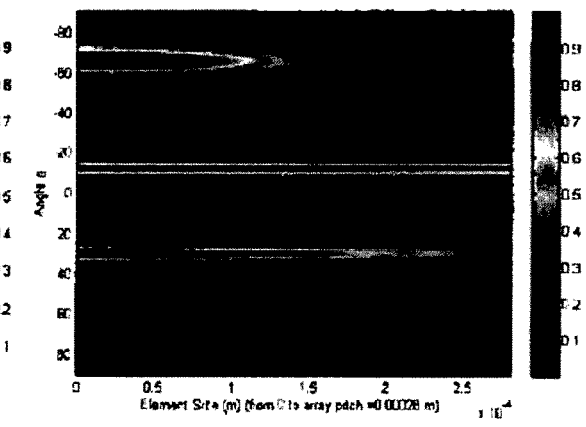
FIG. 76(b) is a graph of array directivity where the steering angle $\theta_s$ equals 30 degrees, showing angle $\theta$ decreasing along the vertical axis from 90 degrees to −90 degrees and element size increasing from 0 mm to 0.28 mm along the horizontal axis, and having a legend for colour values on the right side of the figure ranging from amplitude 0 to amplitude 1.

Both claims can be confirmed by examination of FIG. 76(*a*) and FIG. 76(*b*). Both figures simulate the same array with:
 Number of Elements=10
 Frequency=7.5 MHz
 Pitch (spacing between centre of elements)=0.28 mm While the element width a is varied between 0 and the pitch (0.28 mm), FIG. 76(*a*) simulates the array directivity where the steering angle $\theta_s$ equals 0 degrees while FIG. 76(*b*) simulates the array directivity where the steering angle $\theta_s$ equals 30 degrees. The intensity of the main lobe at different element widths is visible by examining the line $\theta_s$=0 for both figures, while the other horizontal lines represent the undesirable effects of grating. For $\theta_s$=0 (FIG. 76(*a*)), larger element widths attenuate the effects of grating while preserving the desirable main lobe intensity. Conversely, for $\theta_s$=30 (FIG. 76(*b*)), smaller element widths preserve the main lobe intensity while grating lobe intensity is unvaried by element size.

Element Elevation

Figure 73:
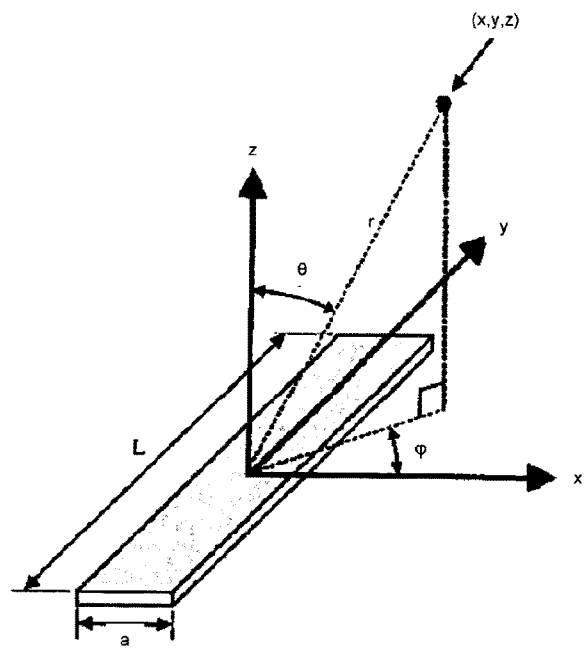
FIG. 73 is a diagram showing the relationship of Cartesian and spherical coordinate systems mapped onto an example linear ultrasound array having length L.

Element elevation is represented as L in FIG. 73. In the far field, a large L (with respect to a) will focus energy in the direction normal to the surface (the z direction) while smaller values for L will radiate energy with larger components in y. In the near field, however, which is generally of interest when inspections are performed at distances comparable to L, energy radiated from the transducer will be projected uniformly from the surface of the transducer in the z direction. This is consistent with expectations, as at these inspection distances, inspection points will be comparable to the elevational focal length of the transducer.

Figure 77A:
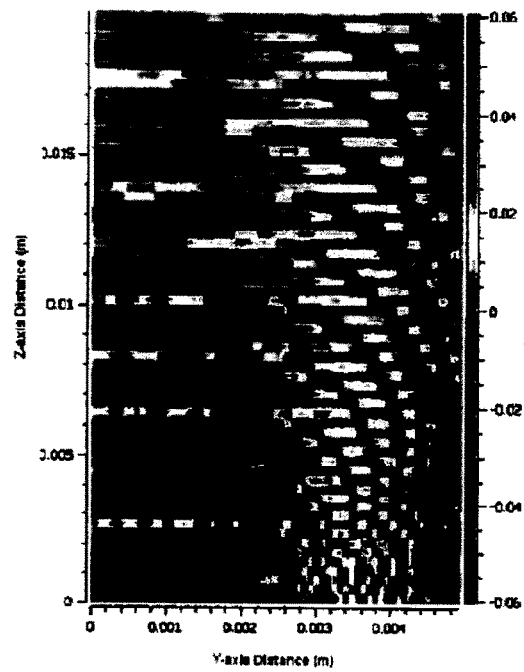
FIG. 77(a) is the pressure field from a 0.25 mm width, 5 mm elevation transducer radiating a 7.5 MHz continuous sine wave intersecting on example planar space $P_1$, showing Z-axis distance increasing from 0 m to 0.015 m along the vertical axis and Y-axis distance increasing from 0 m to 0.005 m along the vertical axis, and having a legend for colour values on the right side of the figure ranging from intensity −0.06 to intensity 0.06.
Figure 77B:
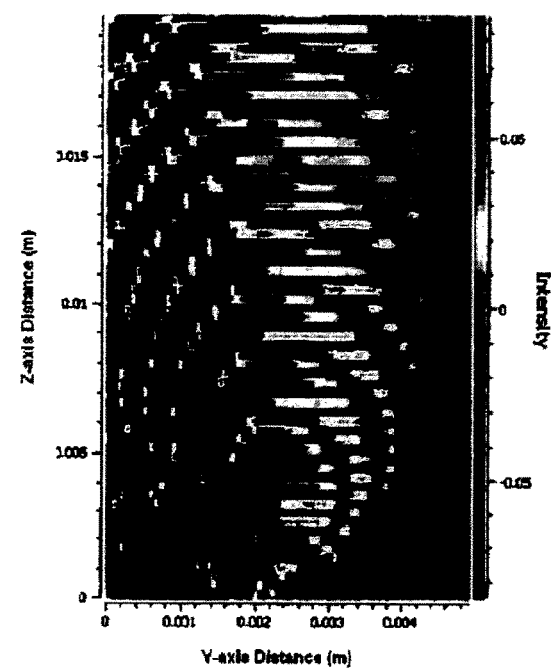
FIG. 77(b) is the pressure field from a 0.25 mm width, 5 mm elevation transducer radiating a 7.5 MHz continuous sine wave intersecting on example planar space $P_2$, showing Z-axis distance increasing from 0 m to 0.015 m along the vertical axis and Y-axis distance increasing from 0 m to 0.005 m along the vertical axis, and having a legend for colour values on the right side of the figure ranging from intensity −0.06 to intensity 0.06.

Recall the coordinate system of FIG. 73. FIG. 77(*a*) and FIG. 77(*b*) reveal the pressure field from a 0.25 mm width, 5 mm elevation transducer radiating a 7.5 MHz continuous sine wave intersecting on two planar spaces $P_1$={x=0, 0≤y≤5, 0≤z≤20} and $P_2$={x=1, 0≤y≤5, 0≤z≤20} (all dimensions are in millimeters). The first space $P_1$ is a plane spanned by vectors in they and z direction and bounded at y=0.5, and z=0.20. Space $P_2$ is spanned and limited in the same manner as $P_1$, but is spaced 1 mm away from $P_1$. Both spaces are shown in FIG. 75. FIG. 77(*a*) and FIG. 77(*b*) illustrate that the intensity of the pressure field radiated by the transducer is concentrated in the y<2.5 mm area for both cases simulated. The symmetry of the radiated field is exploited in the simulations given. If the radiated pressure field was simulated at planar spaces $P'_1$={x=0, −5≤y≤0, −20≤z≤0} and $P'_2$={x=1, −5≤y≤0, −20≤z≤0} which are reflections of planar spaces $P_1$ and $P_2$ about the z-x plane, the intensity field simulated on these spaces would be a reflection of those on $P_1$ and $P_2$ about the z-x plane.

Quantization Noise

In analog-to-digital conversion, the magnitude of each data sample is converted into an approximated value with finite precision. Quantization is a non-linear process. The smallest quantization level is the resolution. It is determined by the full-scale input amplitude of an analog/digital (A/D) converter and the total number of quantization levels which are usually evenly spaced. The resolution is often expressed by the number of quantization level. A 10-bit A/D converter has 1024 quantization levels. A 12-bit A/D converter has 4096 quantization levels. The resolution of a 12-bit AID converter is four times smaller than that of a 10-bit A/D converter. Since the quantization error is expected to be smaller than the smallest quantization level, a higher resolution A/D converter is in general preferred.

If the quantization process rounds the input data value to the nearest quantization level and the errors obey the evenstatistical distribution over the quantization intervals, the mean value of the quantization error is clearly zero. The variance of the quantization error is given by $$\sigma_e^2 = \frac{\Delta^2}{12}$$

where Δ is the quantization interval.

The root-mean-squared (rms) value of the quantization error is the standard deviation $$\sigma_e = \frac{\Delta}{\sqrt{12}} \approx 0.29\Delta.$$

I we define a SNR to be the ratio of signal variance to the noise variance, the SNR of a B+1 bit A/D converter can be expressed in some embodiments as:

$$SNR = 6.02B + 10.8 - 20\log_{10}\left(\frac{X_m}{\sigma_x}\right)$$

where $X_m$ is the full scale level of the A/D converter, and $\sigma_x$ is the standard deviation of the signal.

The SNR limits for 8-bit, 10-bit and 12-bit in this example embodiment are 50 dB, 62 dB and 74 dB respectively. It is worth noting that the optimum SNR can generally only be achieved when the input signal is carefully adjusted to the full-scale amplitude of the A/D converter.

Preprocessing

Figure 18:
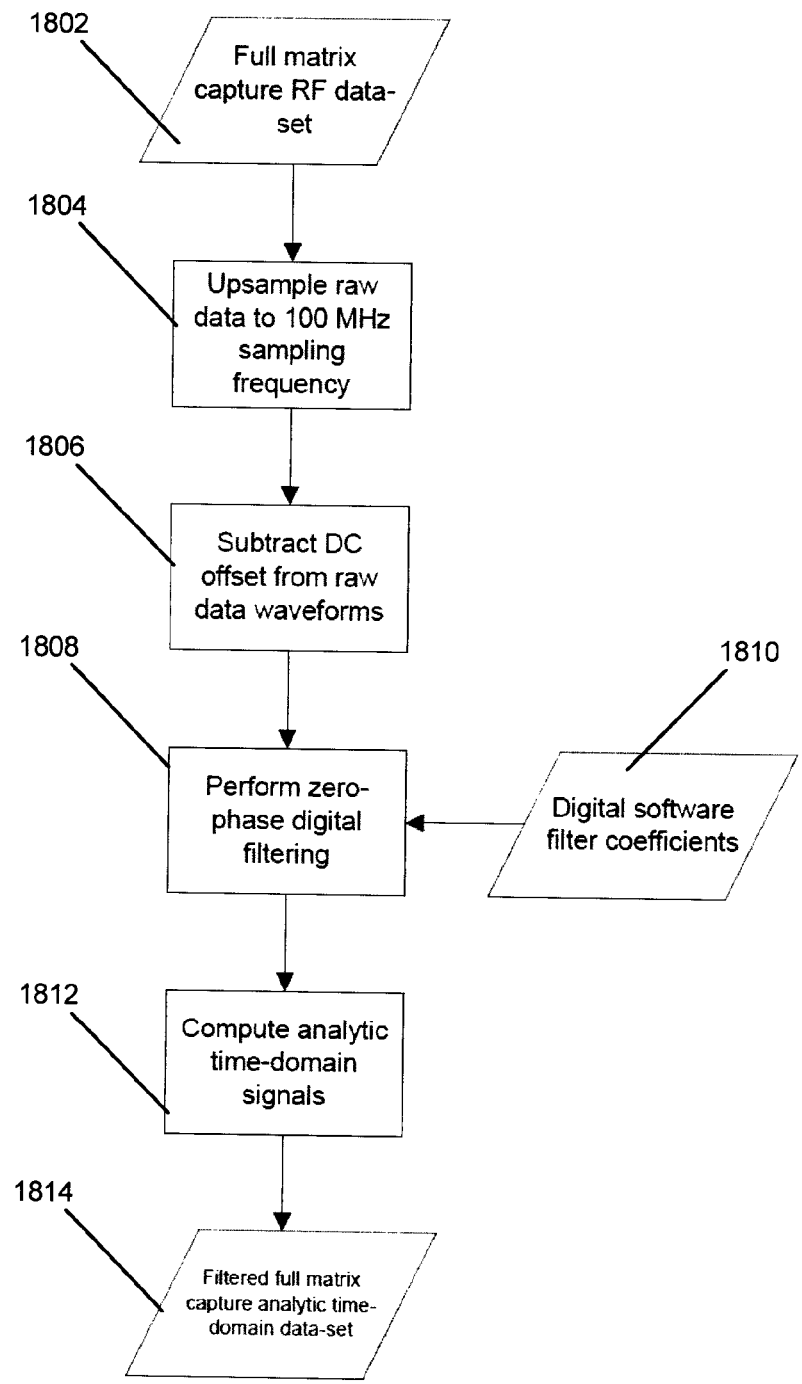
FIG. 18 is a flow chart showing the steps involved in pre-processing of captured ultrasound data according to an example embodiment.

In some embodiments, preprocessing consists of several operations which condition raw data for analysis via the SFM and IFM subroutines. In an example embodiment shown in FIG. 18, these operations are as follows: upsampling the full matrix capture raw data to a sampling frequency of 100 MHz 1804, subtracting the DC offset from the full matrix capture raw data 1806, filtering the full matrix capture data set to remove unwanted noise 1808 using digital software filter coefficients 1810, and calculating 1812 the analytic time-domain full matrix capture data-set 1814 from the acquired RF full matrix capture data set 1802.

In this example embodiment, full matrix capture (FMC) raw data 1802 is collected by the acquisition system at a sampling frequency of 50 MHz. Analyzing the raw data collected at this frequency may deliver results with insufficient accuracy. For this reason, the raw data is upsampled to 100 MHz at step 1804. The acquisition system in this embodiment is sensitive to frequencies less than 25 MHz, and data is collected at twice this rate, so due to the Nyquist Sampling Theorem, the raw data can be perfectly reconstructed at any sampling rate above 50 MHz. The FMC raw data is upsampled from 50 MHz to 100 MHz.

The acquisition system stores raw data via a 12-bit quantization scheme where only positive values are stored. In this embodiment, FMC waveforms are centered about $2^{12}/2=2048$. The analysis algorithms require that waveforms be centered about zero. In some embodiments, the theoretical DC offset value of 2048 may not be exactly accurate: there may be a DC offset inherent in the hardware controlling the ultrasound probe array. Experimentation may show the right DC offset value to use to get a zero value as closely as possible to reality; in some embodiments using specific hardware, the value is 2058. Therefore a DC offset of 2058 is subtracted from each FMC waveform. The exact value of the DC offset may be a user configurable parameter which can be changed to account for other deviations from the theoretical value. The DC offset is subtracted at step 1806.

Unwanted frequency content in the full matrix capture data will sometimes be present due to various noise contributions. These frequencies can be attenuated at step 1808 through the utilization of a digital software filter. Software filtering coefficients may be specified in the filtering process, such as parameters derived from the Filterbuilder program in the Matlab™ software application, at step 1810.

Assigning intensities to points in the inspection medium requires the full matrix data-set of analytic time-domain signals. The full matrix data-set output of the acquisition system 1802 contains the RF data-set (the real part of the analytic time-domain signals). To compute the analytic time-domain signals 1814 from the RF data-set at step 1812, the Hilbert transform of the RF data-set is calculated, multiplied by the imaginary number, i, and added to the RF data-set.

Detailed descriptions of functions used in an example embodiment of the system are set out in Table A1 at the end of the Description.

Shifting Aperture Focus Method (SFM)

Figure 20:
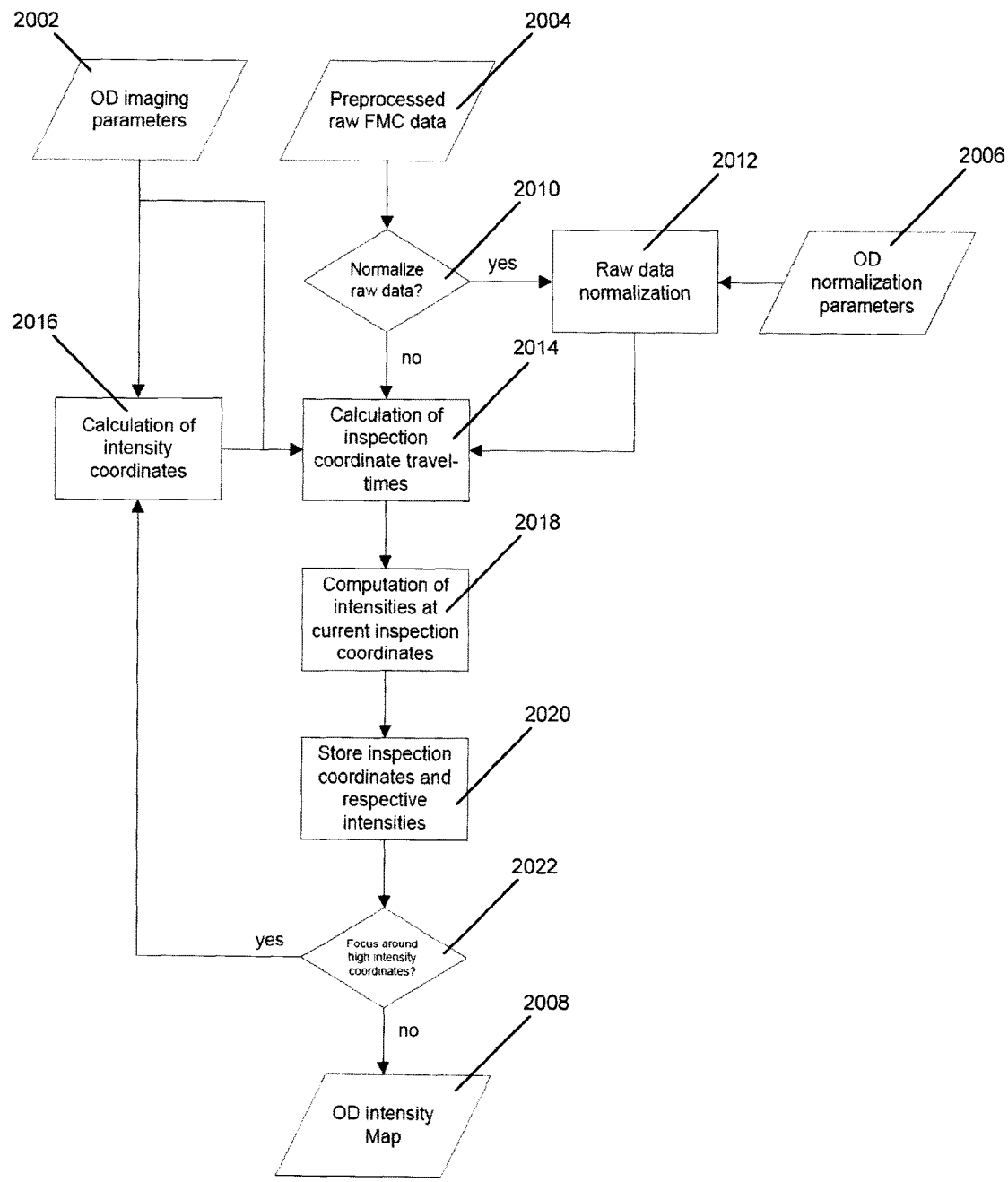
FIG. 20 is a flow chart showing the steps involved in building an intensity map using the Shifting Aperture Focus Method according to an example embodiment.
Figure 21:
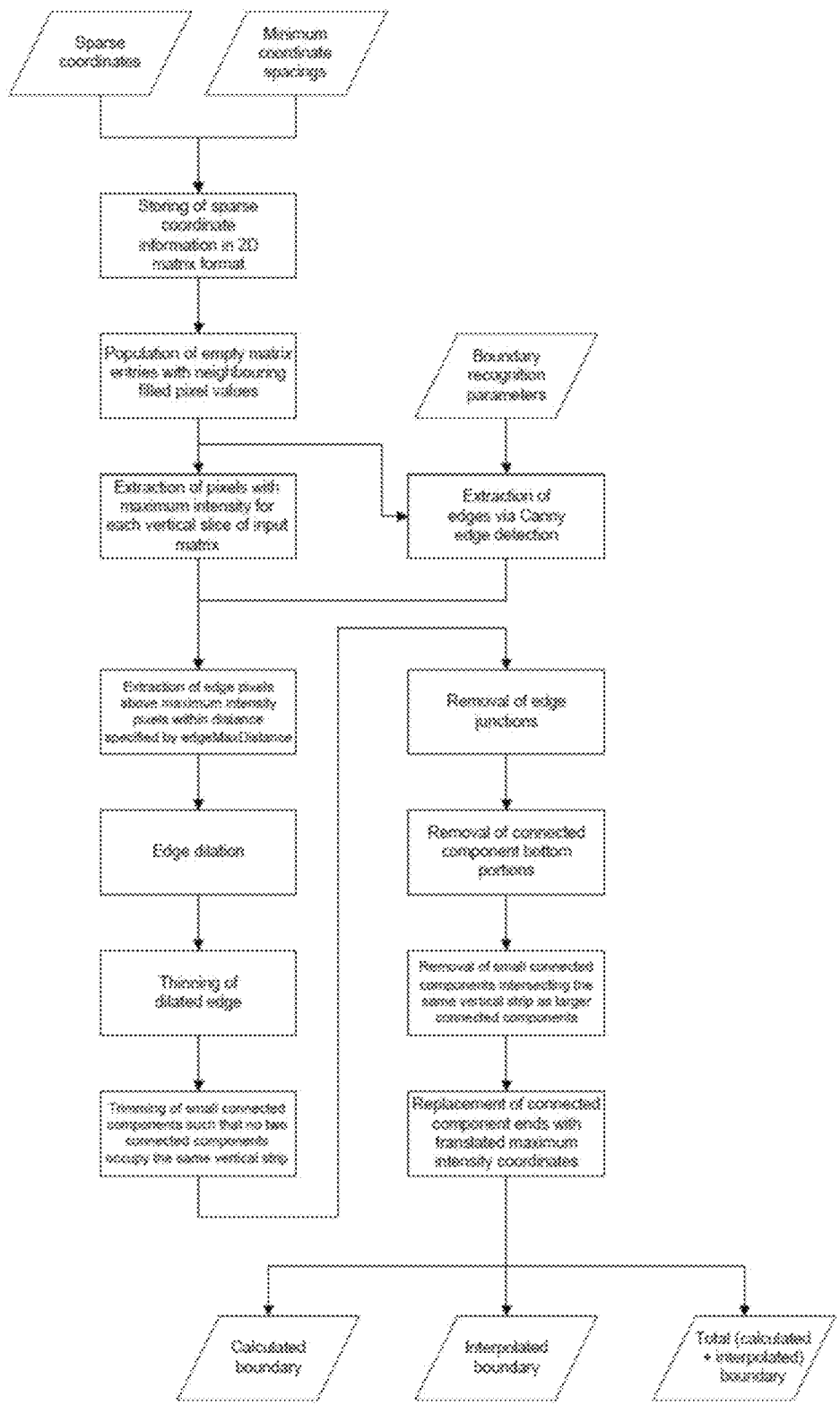
FIG. 21 is a flow chart showing the steps involved in boundary recognition of an intensity map according to an example embodiment.

Once pre-processing 1704 is done, the Shifting Aperture Focus Method (SFM) is applied to the pre-processed data at step 1706. The Shifting Aperture Focus Method is an algorithm whose purpose is to output an intensity map given full matrix capture raw data. The operation of the SFM to determine the OD intensity map is shown in the flowchart of FIG. 20. The pre-processed FMC data 2004 may or may not be normalized first, depending on the embodiment or on user-defined parameters for processing. The decision to normalize is made at step 2010. If the data 2004 is to be normalized, normalization occurs at step 2012 as further described below, based on OD normalization parameters 2006 either pre-defined or set by a user. The normalized or non-normalized data is then used to calculate inspection coordinate travel times at step 2014 as further described below, a process which may take into account intensity coordinates calculated at step 2016 based on OD imaging parameters 2002. At step 2018, the intensities at the current inspection coordinates are calculated. At step 2020, the inspection coordinates and their respective intensities are stored. At step 2022, the algorithm may focus further around high intensity coordinates; if it does, the intensity coordinates are calculated at step 2016, creating an iterative loop for steps 2014 to 2022. When the algorithm has iterated through this process one or more times, it stops re-focusing and outputs an OD intensity map 2008. These various steps are described below.

The Shifting Aperture Focusing Method is a variation on the Total Focusing Method (TFM). The Total Focusing Method is a known technique for imaging in a single medium where sound travels at speed c.

In the Shifting Aperture Focusing Method, first, an intensity function is computed for each point r in the scanning area by summing a function $g_{(i)j}(t)$ for each transmitting element i and each receiving element j within a fixed-width aperture a spanning a set number of adjacent elements in the array. (In some embodiments, the width of the defined aperture may be user-configurable.) Ultrasound elements i 210 and j 212 belong to aperture a. $g_{(i)j}(t)$ is the amplitude of the data-set of analytic time-domain signals from transmitter i 210 to receiver j 212 at time t (note that $g_{(i)j}(t)$ is defined for every i and j, since the full matrix of ultrasonic transmit-receive array data is acquired). i 210 is enclosed in parentheses to represent it as the transmitter, while j 212 is left without parenthesis to represent it as the receiver. The intensity at r is defined as:

$$I(r, a) = \left| \sum_{i,j \in a} g_{(i)j}\left(t = \frac{|e_{(i)} - r| + |e_j - r|}{c}\right) \right|$$ (Equation 2)

where r is the vector defining point r relative to a coordinate origin, $e_{(i)}$ is a vector defining the position of transmitter i relative to the coordinate origin, $e_j$ is a vector defining the position of receiver j relative to the coordinate origin, and c is the speed of light.

Total focusing is achieved by calculating the above for every point in the imaging area 14 (r is varied). By varying r over a set of points sufficiently close to each other such that I(r, a) does not vary significantly between adjacent values of r, an image of the inspection medium can be formed with image pixels of intensity I(r, a) at positions r. This image is called an intensity map.

The next step in the Shifting Aperture Focusing Method is to shift the aperture a along the array and perform the same calculation again for the new aperture. After intensities have been computed for each aperture, the highest such intensity value is used to represent the intensity of point r in the intensity map. Thus, SFM addresses the problem of how to relate intensities from different apertures in assigning an intensity value to r. In many instances, a surface contains reflectors that vary with respect to which apertures they reflect sound best to. For example, one reflector may return sound well to apertures $a_1$ through $a_6$, while another reflector may return sound well to only aperture $a_3$. In imaging a surface, however, reflectors should be imaged with equal intensity, irrespective of how many apertures individual reflectors reflect sound well to. This will lead to increased intensity levelness in imaging the surface. To this end, I(r) is defined as the maximum intensity at r of the set of computed intensities at r with respect to apertures a∈A. I(r) is defined as:

$$I(r) = \max_{a \in A}\{I'(r, a)\}$$ (Equation 3)

Implementation of the SFM routine can become very computationally intensive if there are many coordinates for which corresponding intensities are evaluated. Limiting the number of coordinates under consideration, while focusing at the appropriate density to meet inspection specifications, may require careful implementation of a focusing strategy. The strategy employed in some embodiments is to first calculate intensities of coordinates on a course grid lying in the area of inspection.

Detailed descriptions of OD Imaging Parameters used in an example embodiment of the system are set out in Table A2 at the end of the Description. Detailed descriptions of SFM Functions used in an example embodiment of the system are set out in Table A3 at the end of the Description.

FMC Data Normalization

Figure 15:
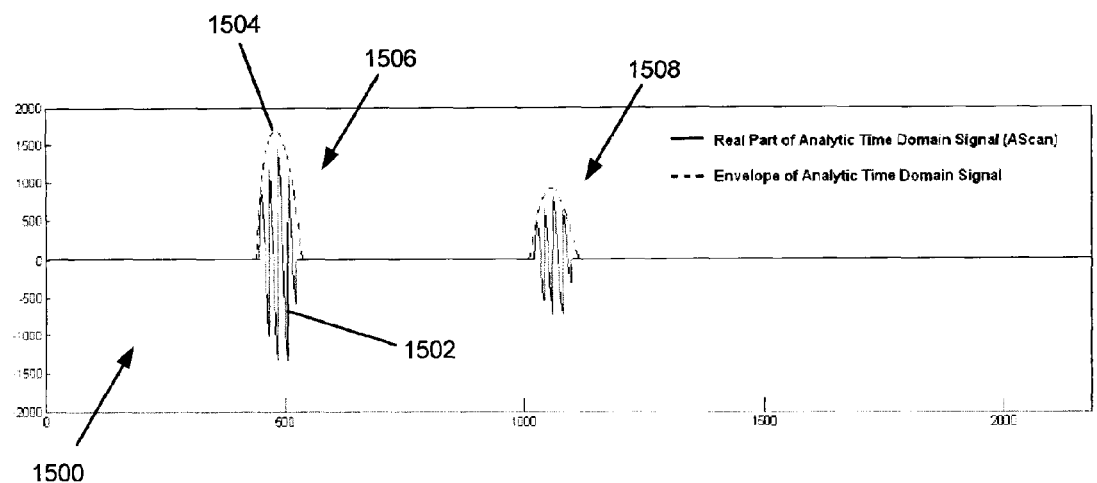
FIG. 15 is a graph of an the real part and the envelope of an A-scan signal before wave packet normalization.
Figure 16:
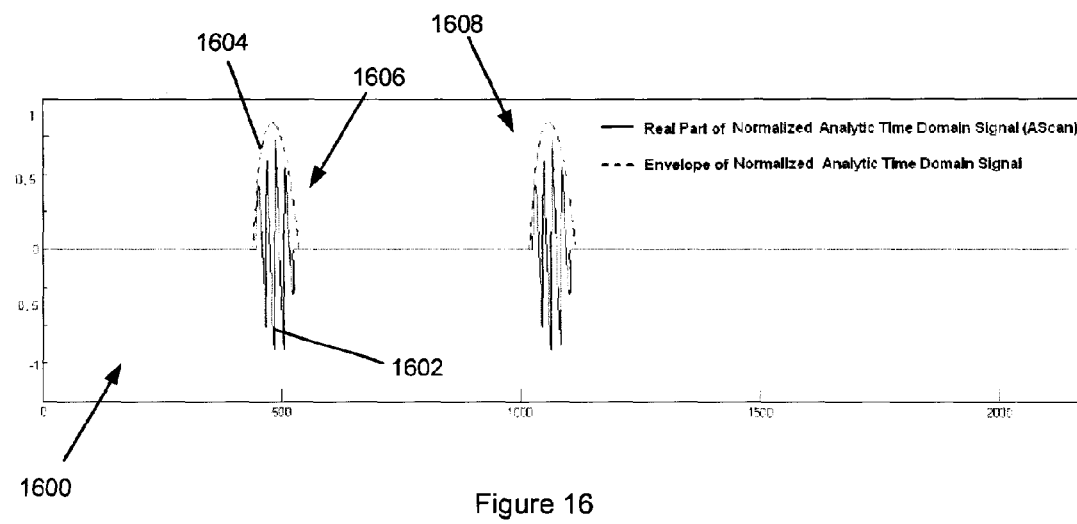
FIG. 16 is a graph of an the real part and the envelope of an A-scan signal after wave packet normalization.

The Total Focusing Method and Shifting Aperture Focusing Method (as well as a further variation, the Interior Focusing Method, described below) may use Beam Normalization. Beam-steering at angles away from the direction normal to an array may be optimized when individual elements are omnidirectional. A correction factor may be introduced in imaging to emulate beam-spread omnidirectionality. A potential problem with this method is that it presumes signals found in $g(i)_j(t)$ are located in the direction of r, when assigning a value to I(r,a). While this may not be a problem of great concern when attempting to image small objects, when imaging surfaces this may lead to amplified grating. Amplified grating causes a reduction in signal to noise ratio in areas of the image where the true surface and grating overlap. The method presented here for normalizing beam-spread is to normalize wave-packets found in the real and imaginary parts of $g(i)_j(t)$ such that the envelope of $g(i)_j(t)$, $|g(i)_j(t)|$, has peak(s) equal to an arbitrary constant. For simplicity, in this example this constant is equal to 1. Thus, if $g(i)_j(t)$ contains wave packets $W=\{w_1, w_2, \ldots, w_n\}$ and $|g(i)_j(t)|$ has peaks $P=\{p_1, p_2, \ldots, p_n\}$, to normalize the peaks of $|g(i)_j(t)|$ to 1, the wave packets W are scaled by $\{p_1^{-1}, p_2^{-1}, \ldots p_n^{-1}\}$. Let $g'(i)_j(t)$ denote $g(i)_j(t)$ with normalized wave packets. FIG. 15 and FIG. 16 illustrate this concept of analytic time domain signal normalization. The A-scan data 1500 in FIG. 15 has a real part 1502 that exhibits a first peak 1506 and a second peak 1508. The envelope 1504 of the signal is higher for the first peak 1506 than for the second peak 1508. After applying wave packet normalization as described above, the normalized A-scan 1600 is shown in FIG. 16. The real part 1602 of the A-scan 1600 has had the envelope 1604 of its first peak 1606 and its second peak 1608 normalized to the same constant value.

SFM Refocusing

At step 2022, depending on preset or user defined parameters, the SFM subroutine either ends, outputting the intensity map 2008 to the boundary detection subroutine, or proceeds to define new coordinates for which to calculate corresponding intensities at step 2016. If the latter course is taken, newly defined coordinates will be positioned around coordinates with high intensities already assigned to them. The cutoff intensity for coordinates of which newly defined coordinates focus around may be defined by a predefined vector. Once the new coordinates have been defined, potentially depending on user defined parameters, the SFM subroutine exits, or proceeds to further focus around coordinates of high intensity. The process of identifying high intensity coordinates and then refocusing around them can be executed an arbitrary number of times, which may be specified by a user in some embodiments.

Figure 19:
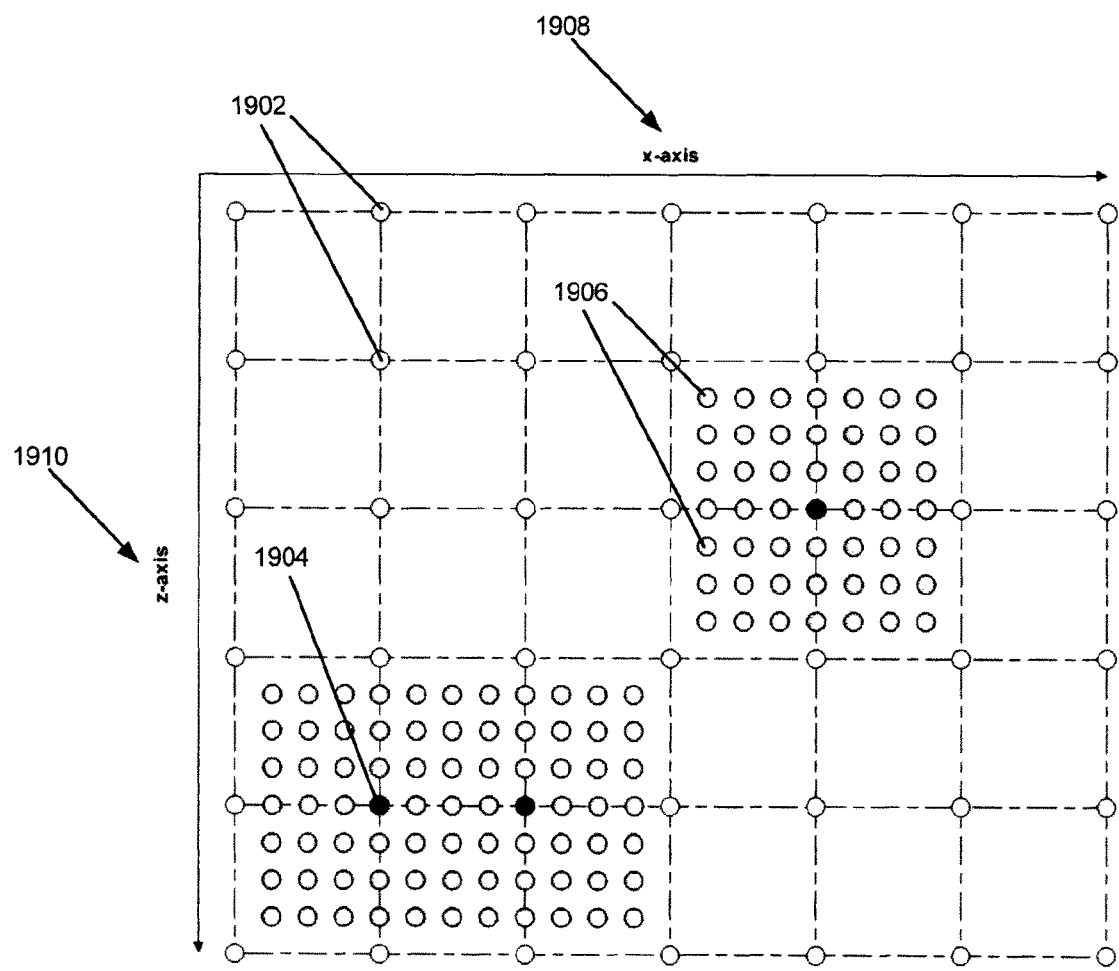
FIG. 19 is a cross-sectional view of an X-Z scanning plane through a pipe wall showing how an intensity map is built in an example embodiment.

One cycle of the refocusing process (steps 2014 to 2022) is illustrated in FIG. 19. Coordinates spaced coarsely apart are represented as either white circles 1902 or black circles 1904. The white circles 1902 represent those coordinates whose respective intensities are below the cutoff intensity for which new coordinates are defined. Conversely, the black circles 1904 represent those coordinates whose respective intensities exceed the cutoff intensity for which new coordinates are defined. The gray circles 1906 represent newly defined coordinates around high intensity coordinates. If the gray circles 1906 are defined on iteration i+1 of the coordinate definition and intensity assigning process, dx(i)/dx(i+1)=dz(i)/dz(i+1)=4 for the example illustrated by FIG. 19 with x-axis 1908 and z-axis 1910.

Intensity Maps

Figure 12:
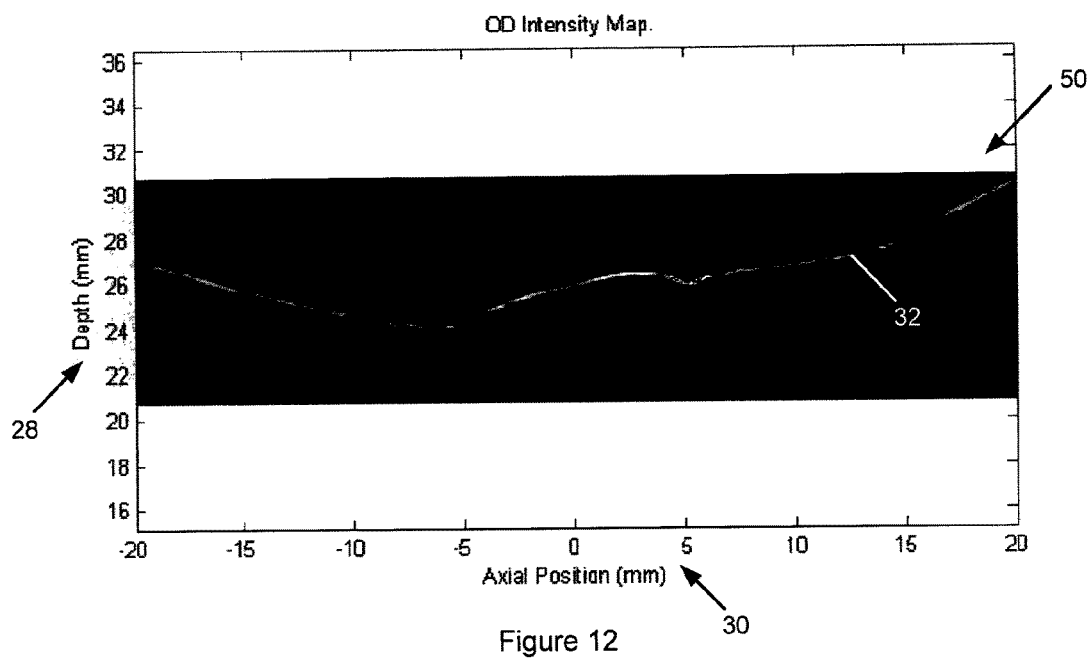
FIG. 12 is an intensity map in the scanning plane of the outer surface of a pipe wall.

An example intensity map of the OD (outer surface) of a pipe 2 is shown in FIG. 12. The OD intensity map 50 is mapped within the same plane as FIG. 11, with the depth 28 of the scan as the vertical axis and the axial position 30 along the longitudinal axis 4 as the horizontal axis. The high-intensity OD regions 32 in the OD intensity map 50 indicate the shape of the outer pipe surface in the axial direction at the radial position of the probe array 200 during the current transmit-receive cycle.

Boundary Recognition and Definition

The OD intensity map 50 can be further processed, either on its own or in conjunction with neighbouring intensity maps from separate transmit-receive cycles, to build a model of the outer pipe surface. In the example embodiment shown in FIG. 17, boundary recognition is performed at step 1708 followed by boundary definition at step 1710.

Boundary recognition is executed as follows. Given an intensity map (stored in sparse coordinates in some embodiments) of the OD coordinates or an intensity map of the ID coordinates along with corresponding boundary recognition parameters, the boundary recognition algorithm will output the surface boundary.

Boundary recognition and definition are intended to define the true boundary of the OD/ID (not edges of aberrations in the image), and the extraction of the boundary in the form of a set of coordinates. The algorithms and tolls used to accomplish this task are common challenges in the field of computer vision, and any of a number of algorithms could be employed to recognize and define the boundary of a surface given an intensity map.

In some embodiments, the tools used for these tasks are a robust edge detection algorithm, various morphology operations, and association of high intensity regions of the intensity map with potential boundaries. These tools are described in detail below.

In general, an image is given by A=f(m,n), where pixel (m,n) is located at row m and column n of the image. Both m and n are elements of the set of integers, Z. f is a function outputting a real number (an element of the set R) such that f:$Z^2 \to R$. If we restrict f(m,n) to values of either 0 or 1, then the image f(m,n) is referred to as a binary image.

Example Algorithms Used in Boundary Recognition and Definition

The following portion of the specification defines some basic set operations on images, which form the groundwork for higher level operations defined in subsequent subsections. We first introduce the translation and reflection operations. For an image A, the translation of A by x=(p,q) is represented by A and is defined as $$A_x = \{f(m+p, n+q) | f(m,n) \in A\} \quad \text{(Equation 4)}$$

The reflection operation, denoted Â, is given as $$\hat{A} = \{f(-p,-q) | f(p,q) \in A\} \quad \text{(Equation 5)}$$

Furthermore, introduced are the fundamental union and intersection operators, represented by ∪ and ∩ respectively. The union of two images A=f(m,n) and B=g(m,n) is defined as $$A \cup B = \{\max(f(m,n), g(m,n)) | f(m,n) \in A, g(m,n) \in B\} \quad \text{(Equation 6)}$$

whereas the intersection of the two images A and B is defined as $$A \cap B = \{\min(f(m,n), g(m,n)) | f(m,n) \in A, g(m,n) \in B\} \quad \text{(Equation 7)}$$

Regions of adjacent images which share the same values are identified as connected components. While there are different measures of connectivity, the present described example embodiment considers pixels which are 8-connected. If any two pixels are adjacent to one another (including diagonally adjacent), then they are considered 8-connected.

Dilation and Erosion

Different algorithms exist for labelling connected components of an image. In general, given an image A, a new image B can be defined such that the values of its pixels are the labels of the connected components in image A. For a given image of interest, A, a structuring set B, called the 'structuring element', is an image which, along with either a dilation or erosion operation, is used to modify the image of interest.

The dilation operation is defined as $$A \oplus B = \{x | \hat{B}_x \cap A \neq 0, x=(m,n), m,n \in Z\} \quad \text{(Equation 8)}$$

Effectively, the dilation operation enlarges image A by reflecting B about its origin and then shifting it by x. Erosion on the other hand is defined as $$A \ominus B = \{x | B_x \cap A = B, x=(m,n), m,n \in Z\} \quad \text{(Equation 9)}$$

Erosion preserves 1's in A which when B is translated by x and is intersected with A, equals B. Erosion has the effect of trimming boundary 1's from an image given an image B which is centered on the origin.

Figure 22:
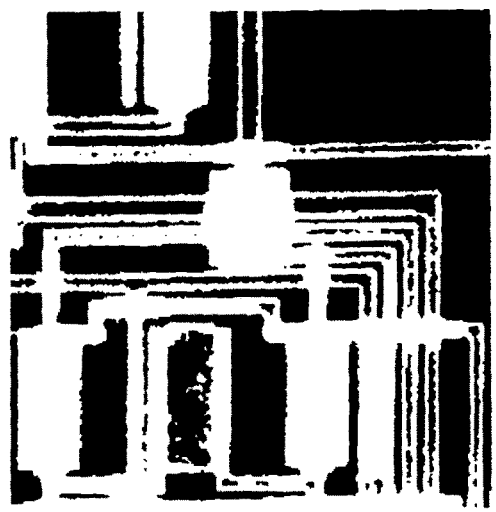
FIG. 22 is an example black-and-white image used in conjunction with FIGS. 23 through 25 to illustrate the effect of erosion and dilation operations.
Figure 23:
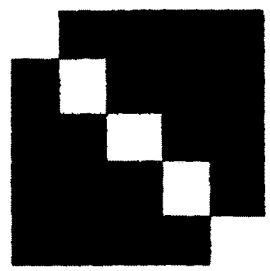
FIG. 23 is an example 5×5 matrix, centered around the origin, used as the structuring element in conjunction with FIGS. 22, 24 and 25 to illustrate the effect of erosion and dilation operations.
Figure 24:
FIG. 24 is a black-and-white image showing the effect of an erosion operation on FIG. 22 using the structuring element of FIG. 23.
Figure 25:
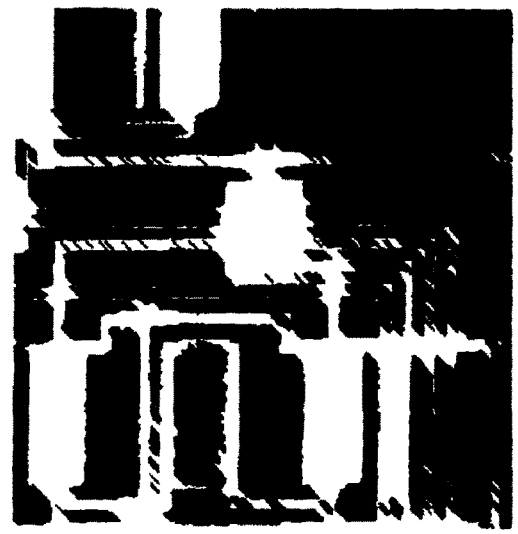
FIG. 25 is a black-and-white image showing the effect of a dilation operation on FIG. 22 using the structuring element of FIG. 23.

FIGS. 24 and 25 illustrate the dilation and erosion operations, respectively, performed on the image given in FIG. 22. The structuring element used in the dilation and erosion operations is a 5×5 matrix, centered on the origin, given in FIG. 23.

Edge Detection

Edge detection can be performed using an edge detection algorithm as known in the art. One of the most popular, robust, and versatile edge detectors used is the Canny Edge detector. It is described in detail below.

The first step in Canny edge detection is to smooth the input image. The purpose of this smoothing is to reduce noise and unwanted details and textures. The smoothing process is performed via convolution of the image with a two dimensional Gaussian function. Where the image is given by f(m,n), and the Gaussian is given by Gσ(m,n), the convolution is given by $$g(m,n) = f(m,n) * G\sigma(m,n) \quad \text{(Equation 10)}$$

The particular two dimensional Gaussian used here is of the form $$G\sigma(m,n) = A e^{-\left(\frac{m}{2\sigma_m^2} + \frac{n}{2\sigma_n^2}\right)} \quad \text{(Equation 11)}$$

where $\sigma_m$ and $\sigma_n$ are variances of the Gaussian in the vertical and horizontal directions respectively. In traditional implementation of Canny edge detection, $\sigma_m = \sigma_n$, yielding a simpler form of Equation 11. However, in the present described example embodiment, spacing between vertical pixels and horizontal pixels is not necessarily the same. For example, pixels adjacent to each other in the vertical direction may represent locations 0.01 mm apart, while pixels adjacent to each other in the horizontal direction may represent locations 0.015 mm apart. Therefore, if a Gaussian is used in the convolution process which is circular as opposed to elliptical in shape (not stretched in either the vertical or horizontal directions) with respect to actual locations of pixels, $\sigma_m$ will not be equal to $\sigma_n$ if spacing between vertical pixels and horizontal pixels is different. If the spacing between pixels in the vertical direction is a factor if c times as much as spacing between pixels in the horizontal direction, then $\sigma_m = \sigma_n/c$.

The second step in the edge detection process is to calculate the gradient of the convoluted image, g(m,n). Since g(m,n) is a discrete function, and generally non-analytic, operators have been developed to approximate the gradient of g(m,n), ∇g(m,n). The details of these operators are not described here. Utilization of any of the above mentioned operators produce $g_m(m,n)$ and $g_n(m,n)$ which are two images containing vertical and horizontal gradient approximations. Thus the magnitude and direction of ∇g(m, n) may be represented as M(m,n) and θ(m,n), where $$M(m, n) = \sqrt{g_m(m, n) + g_n(m, n)} \quad \text{(Equation 12)}$$

$$\theta(m, n) = \arctan\left(\frac{g_m(m, n)}{g_n(m, n)}\right) \quad \text{(Equation 13)}$$

Step three is to calculate those pixels in M(m,n) which are local maxima. To do this, for every pixel (m,n), two most neighbouring pixels perpendicular to the direction θ(m,n) are considered. If the value of M at these pixels are both less than that of M(m,n), then (m,n) is considered to be a local maximum. The set of all local maxima in M(m,n) is denoted as $\tilde{M}$(m,n).

Step four is to define two binary images as functions of two respective real numbers, $\tau_1$ and $\tau_2$, respectively, where $0<\tau_1<\tau_2<\tau'$. $\tau'$ is equal to the maximum value of M(m,n). $\tilde{M}\tau^1$(m,n) and $\tilde{M}\tau^2$(m,n) are defined as being images containing values of $\tilde{M}$(m,n) greater than $\tau_1$ and $\tau_2$ respectively. Thus, $$\tilde{M}\tau^i(m,n)=[(1 \text{ if } \tilde{M}(m,n)>\tau_i)_5(0 \text{ otherwise}), i=1,2]$$

The last step (step five) is an iterative process. $E_j$ is a Boolean image containing edges, output at iteration j of the process. $F_j$ is the intersection of those pixels adjacent (in an 8-connected fashion) to pixels with value 1 in $E_j$ and pixels with value 1 in $\tilde{M}\tau^1$(m,n).

Set j=1 $E_1$ as $\tilde{M}\tau^2$ (m,n). The iterative computation begins. If the union of $E_j$ and $F_j$ is equal to $E_j$, then the algorithm terminates, outputting $E_j$ as the canny detected edge. If not $E_j$ is defined as the union of $E_j$ and $F_j$, and j is incremented. The algorithm then loops, testing the equality of $E_j$ and $E_j \cup F_j$, until they are equal. The algorithm outputs $E_j$ when it is equal to the union of $E_j \cup F_j$.

This can be represented in pseudo-code as follows:

```
j=1;
E_j := M̃τ²(m,n);
While E_j ∪ F_j != E_j do
    E_j := E_j ∪ F_j;
    j=j+1;
end
output E_j
```

FIG. 26(a) shows an image of a set of coins, while FIG. 26(b) shows this image processed with Canny edge detection.

Thinning

A thinning algorithm may also be used in boundary detection. Reducing connected components in an image to their thin-line representation has a number of useful applications such as data compression, simple structural analysis, and elimination of contour distortion. One iterative thinning used in an example embodiment is presented here. The ∧, ∨, and symbols represent and, or, and not operations respectively.

Given an image A=f(m,n), the first step in the thinning algorithm is to divide it into two subfields in a checkerboard pattern. The algorithm then uses a parallel approach where the following two sub-iterations are executed in parallel repeatedly, until they have no effect on the image.

The first sub-iteration is to delete pixel p in the checkerboard if and only if conditions $G_1$, $G_2$, and $G_3$ are all satisfied.

The second sub-iteration is to delete pixel p in the checkerboard if and only if conditions $G_1$, $G_2$, and $G_3'$ are all satisfied. Conditions $G_1$, $G_2$, $G_3$, and $G_3'$ are listed as follows:

Condition $G_1$ is:

$$X_H(p)=1$$

where $$X_H(p)=\Sigma_{i=1}^{4}b_i \text{ and}$$

$$b_i=[(1 \text{ if } x_{2i-1}=0 \wedge (x_{2i-1}=1 \vee x_{2i+1}=1),(0 \text{ otherwise})]$$

$x_1, x_2, \ldots, x_8$ are the values of the eight neighbours of p respectively beginning with the east neighbour and numbered counter-clockwise until the south-east neighbour is reached.

Condition $G_2$ is:

$$2 \leq \min\{n_1(p), n_2(p)\} \leq 3$$

where $$n_1(p)=\Sigma_{i=1}^{4}x_{2k-1} \vee x_{2k}$$

$$n_2(p)=\Sigma_{i=1}^{4}x_{2k} \vee x_{2k+1}$$

Condition $G_3$ is:

$$(x_2 \vee x_3 \vee \bar{x}_8) \wedge x_1=0$$

Condition $G_3'$ is:

$$(x_6 \vee x_7 \vee \bar{x}_4) \wedge x_5=0$$

FIG. 27(a) shows a binary image without thinning FIG. 27(b) shows the same image after a thinning algorithm has been applied.

Junction Identification

An algorithm may also be applied to test if a pixel is a junction point of lines in a binary image. Given a 3×3 neighbourhood of a pixel p, p is a junction of lines if and only if when traversing the perimeter of p the number of transitions between 0 and 1 is either 6 or 8. FIG. 28(a) gives a junction of lines and FIG. 28(b) zooms in on this junction and illustrates its 3×3 neighbourhood. It is clear from FIG. 28(a) that the junction has 6 transitions between 0 and 1. Thus, the criterion for junction identification is satisfied.

Implementation of OD and ID Boundary Recognition and Definition

The algorithm employed to extract OD or ID boundary coordinates from an OD or ID intensity map in example embodiments may employ all the tools introduced in the previous subsection and tailor their use to the specific domain of ultrasound scanning.

The first step to extraction of the true OD/ID boundary from the OD/ID intensity map involves identifying canny edge detected boundaries near and above (on the side near to the array 200) maximum intensity pixels in the vertical direction of the intensity map. Given an intensity map, the true boundary may be extracted. The first question that arises is where the precise coordinates of the boundary lie, given the neighbourhood of and around high intensity pixels in an intensity map. It can be observed from a given intensity map (such as FIG. 30) that there is a relatively wide region of high intensity pixilation where the true boundary could lie. To answer this question, the method of calculation of distances from A-Scans is extended to intensity maps. To calculate the distance an ultrasonic wave has traveled in a medium from an A-Scan, the time from transmitter excitation to the leading edge of the received wave packet is multiplied by the speed of sound in the medium. The travel time (in samples at a particular digitization frequency) from transmitter excitation to the leading edge of a received wave packet is shown by numeral 2902 in FIG. 29. The formation of intensity maps involves the mapping of values of analytic time-domain signals (A-Scans along with their Hilbert transforms) to points in the intensity map, per Equation 2. The leading edges of wave packets of A-Scans are mapped to the leading edge of intensity map boundaries where the leading edge of intensity map boundaries are defined as the edges on the near side of the probe array 200. Thus, the OD/ID boundary is derived from leading edges in the intensity map boundaries.

Figure 30:
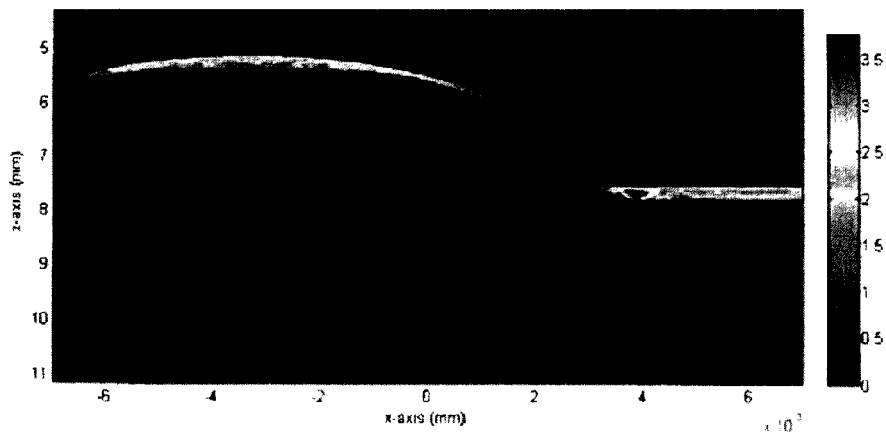
FIG. 30 is an example intensity map of a scanned area.
Figure 31:
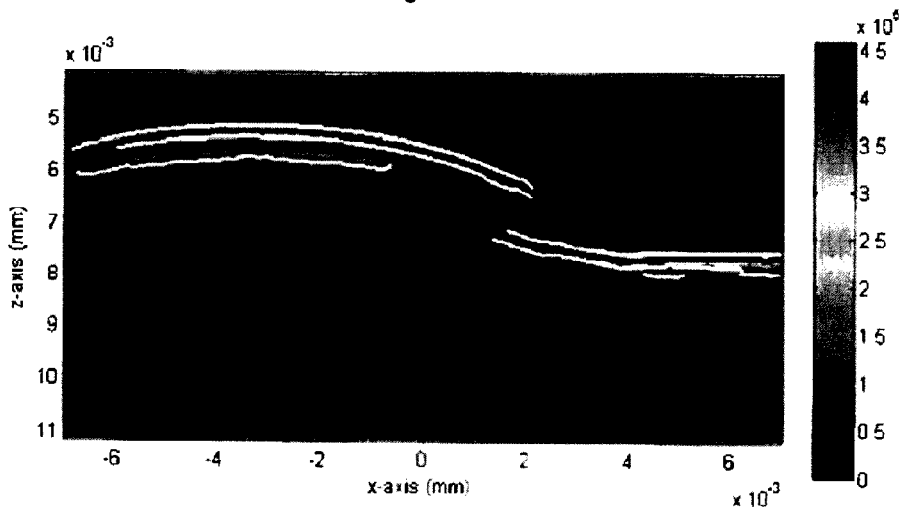
FIG. 31 is a plot of the edges of the intensity map FIG. 30 plotting the pixels of maximum intensity in the vertical direction.
Figure 32:
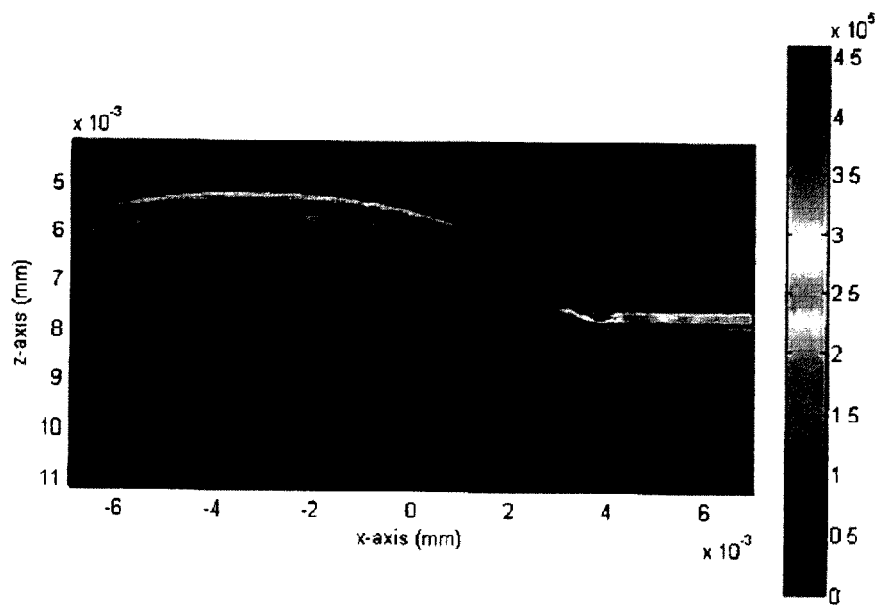
FIG. 32 is a plot of boundary edges near and above the high intensity pixels of FIG. 31.

The second question that arises is how to programmatically identify the true OD/ID boundary with the potential of imaging aberrations (features appearing due to mechanisms such as grating lobes or multiple back-wall reflections) present in the intensity maps. In FIG. 30, of the edges in the image, the true boundary is of the edges nearest to the regions of high intensity, contrasting the edges of aberrations due to grating or back wall reflections. Taking any vertical slice of the image, the true boundary will intersect this vertical slice just above where it will intersect the maximum intensity pixel in that slice. These observations motivate the first step of the boundary detection algorithm, isolation of the true boundary edges through identification of edges near and above the highest intensity pixels in the vertical direction. For a given intensity map such as the one given in FIG. 30, the edges of the intensity map and the pixels of maximum intensity in the vertical direction are plotted in FIG. 31. The true boundary edges are those that are near and above the high intensity pixels and are plotted in FIG. 32.

Identification of the OD/ID boundary solely through the methods employed described above may yield results which can be improved upon. Additional techniques may be used in some embodiments to eliminate error in the boundary defined via the methods described earlier above.

Aberrations can have higher intensity content than the true boundary, which can lead to false identification of the true OD/ID boundary. If these aberrations are small in size, however, operations of dilation and thinning, along with comparison of connected component sizes, can be employed to remove erroneous edges from the boundary definition extracted from the algorithm previously described. Elimination of erroneous edges at this stage in the boundary detection algorithm may be performed via three steps: dilation of the candidate boundary, thinning of the dilated boundary, and trimming of small connected components.

Elimination of Erroneous Edges

Figure 33:
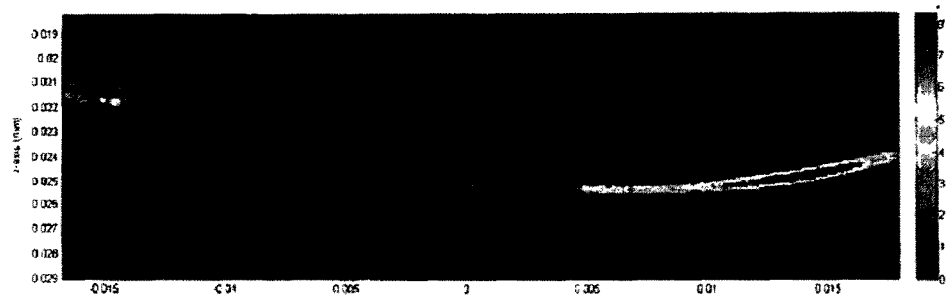
FIG. 33 is a plot of an example output of a boundary detection algorithm without error correction.
Figure 34:
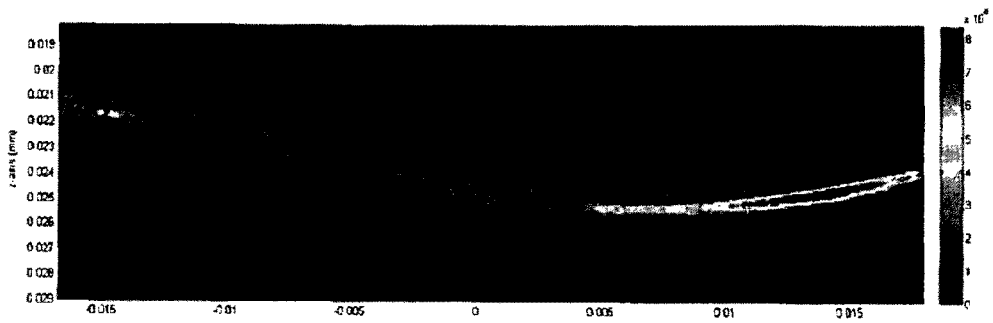
FIG. 34 is a plot of the boundary of FIG. 33 after a dilation operation is performed with a rectangular structuring element.
Figure 35:
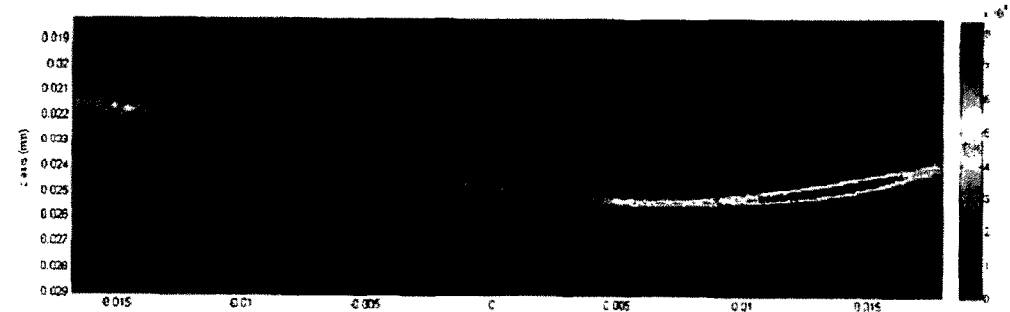
FIG. 35 is a plot of the boundary of FIG. 34 with a thinning algorithm applied to it.
Figure 36:
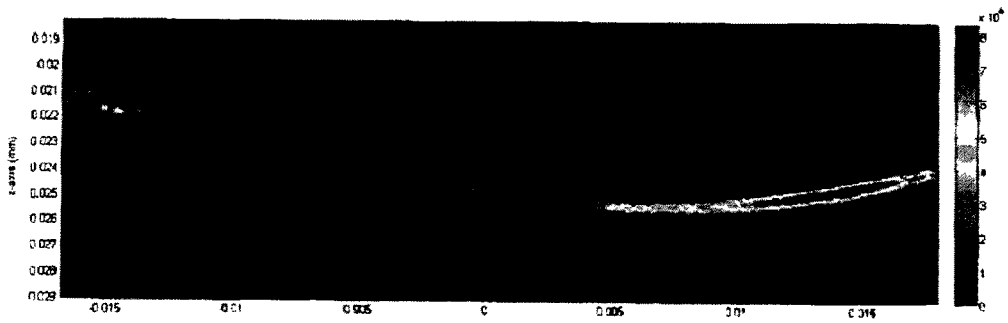
FIG. 36 is a plot of the boundary of FIG. 35 with erroneous pixels removed.

FIG. 33 to FIG. 36 give the boundary at various stages in the execution of an example algorithm for eliminating erroneous edges. The original boundary output from the algorithm given above is depicted in FIG. 33. Due to high intensity content in the aberration below the true boundary, the output boundary contains error. This is evident in that a small region of the output boundary appears above the aberration. FIG. 34 shows the boundary after the dilation operation is performed with a rectangular structuring element. The small gap in the location where the boundary should lie (FIG. 33) has been removed Thinning of the boundary reduces it back to its desired width. The thinned boundary is depicted in FIG. 35. Finally, a comparison of boundary pixels is performed. If there is more than one boundary pixel intersecting any vertical slice of the intensity map, only the pixel belonging to the connected component of largest size (of the pixels under consideration) is preserved. The rest are removed. This serves to remove the erroneous boundary pixels. FIG. 36 gives the boundary with erroneous pixels removed.

Removal of Edge Junctions

The dilation and thinning operations can introduce line junctions as previously defined. At this point in the boundary detection algorithm, junctions may be removed, as set out above, until no junctions exist in the defined boundary. This serves the purpose of preparing the boundary for removal of more erroneous edges, performed via the algorithms described below.

Figure 37:
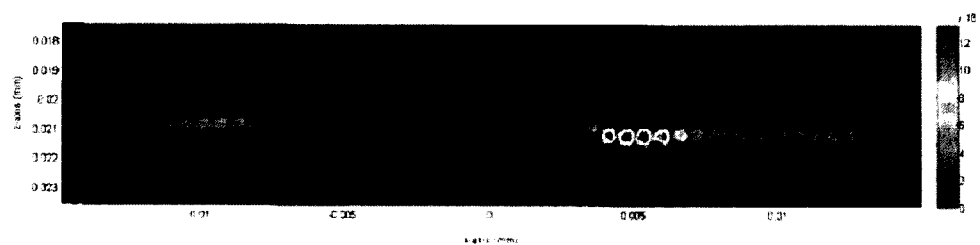
FIG. 37 is an intensity map image of an inner pipe surface (ID)
Figure 38:
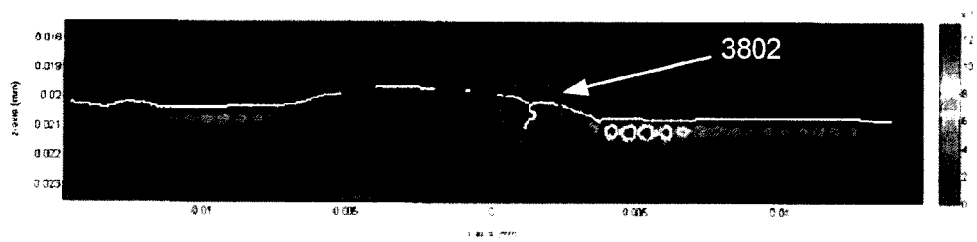
FIG. 38 is the intensity map of FIG. 37 after applying edge detection, dilation and thinning algorithms, with a junction area of the boundary circled.
Figure 39:
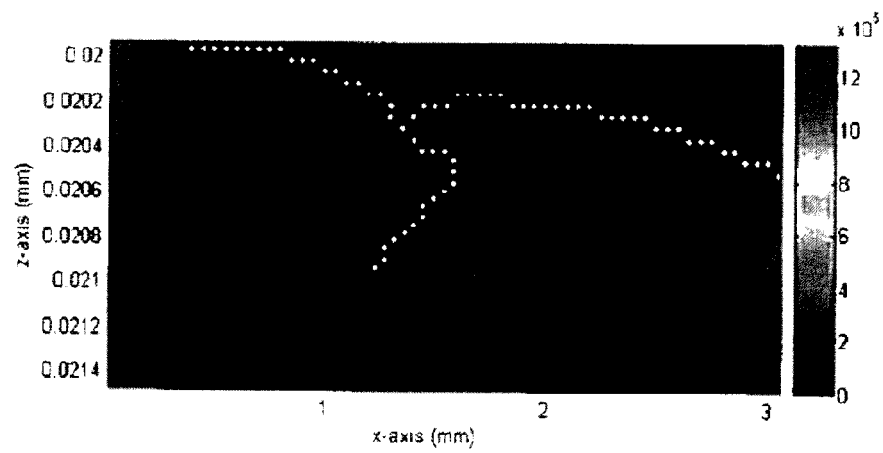
FIG. 39 is an enlarged view of the circled junction area of FIG. 38.
Figure 40:
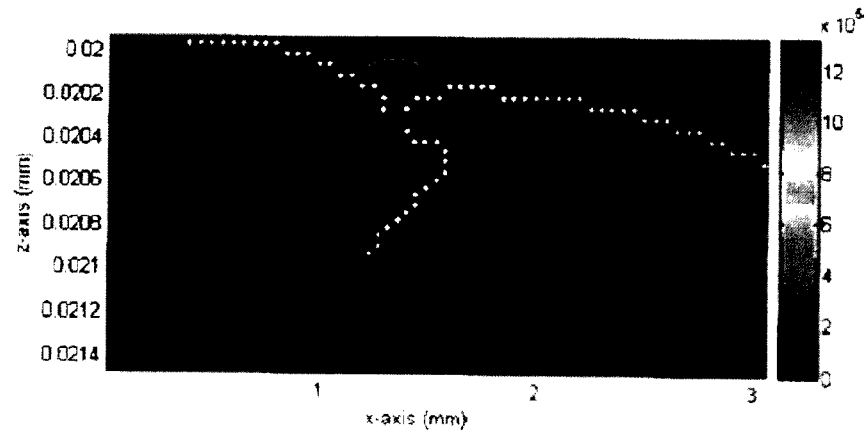
FIG. 40 is the enlarged view of FIG. 39 with the junction removed.

FIG. 37 gives an ID intensity map image. The edge detection, dilation and thinning algorithms give the boundary given in FIG. 38. The junction area 3802 of the boundary encircled in FIG. 38 reveals the area on and around the boundary to be removed as erroneous. This junction area 3802 is shown magnified in FIG. 39. FIG. 40 illustrates the junction area 3802 of the boundary with the junction removed.

Removal of Bottom Portions of Connected Components

Figure 41:
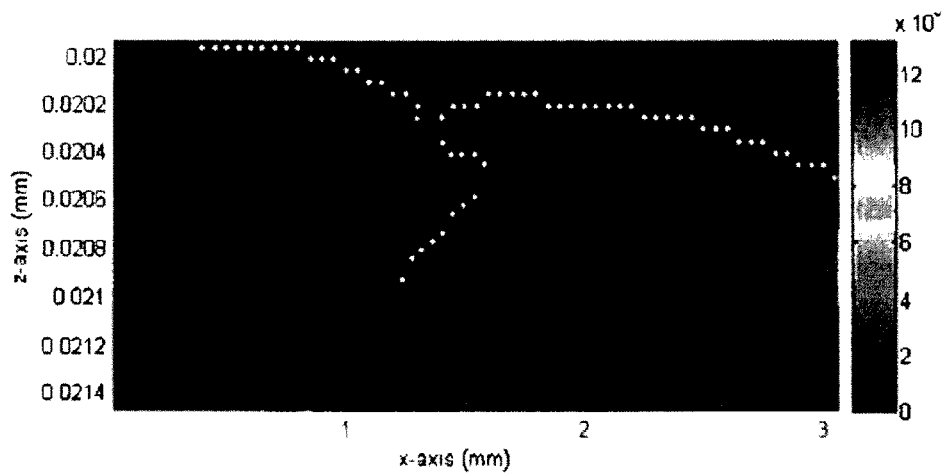
FIG. 41 is the enlarged view of FIG. 40 with bottom portions of connected components removed.

The next phase of the edge detection process is a removal of bottom portions of connected components. Removal of bottom portions of connected components consists of removal of lower connected component pixels. A lower connected component pixel is defined here as a pixel in some connected component having the same x-component as some other pixel(s) in the same connected component, but with greater z-component values (recall pixels with greater z-component values appear lower on intensity maps. FIG. 41 shows the boundary in FIG. 40 with bottom portions of connected components removed.

Removal of Small Connected Components

Figure 42:
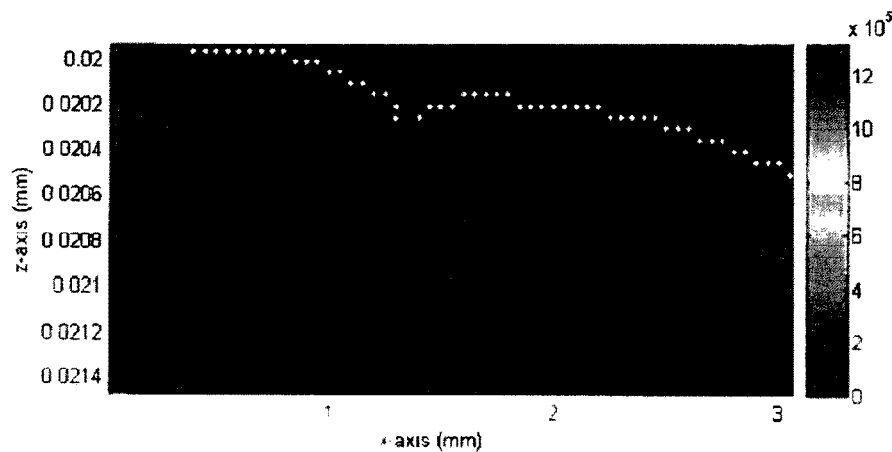
FIG. 42 is the enlarged view of FIG. 41 with small connected components removed.

Small connected components of erroneous edges can still remain in the intensity map. Removal of these edges increases the accuracy of the defined boundary. For every vertical strip of the intensity map, if more than one connected component intersects this slice, then only the largest one is preserved in the intensity map. FIG. 42 illustrates the edge boundary with small connected components removed. This image is the most accurate of any so far in the identification of the true edge boundary of the intensity map depicted in FIG. 37.

Approximation of Horizontal Ends of Connected Components

Figure 43:
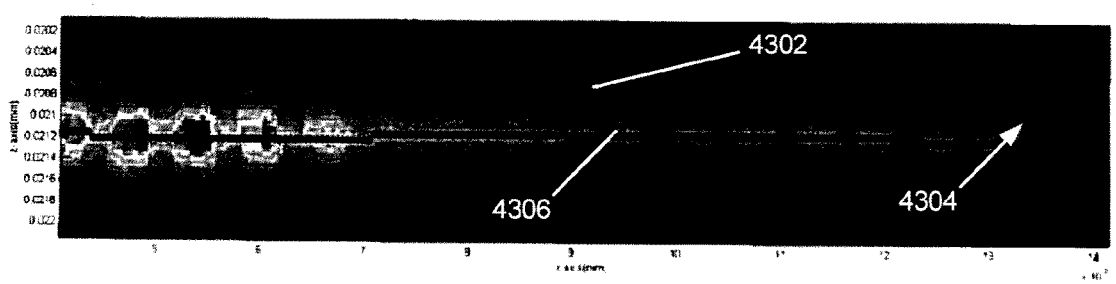
FIG. 43 is a pipe surface intensity map showing the edge output from a Canny edge detector and a graph of the maximum intensity pixels approximating the shape of the true boundary as a flat plate.

Intensity maps are formed from ultrasonic raw data. The decrease in usable ultrasonic raw data near the ends of boundaries will result in a thinning of high intensity content. Using the Canny edge detection process to determine the true boundary in these areas will result in poor determination of the true OD/ID boundary as the edges output curve around the high intensity content, where in fact the true boundary may be flat. FIG. 43 illustrates the edge output from the Canny edge detector 4302 in red. Indeed the curvature defined in the area 4304 where the intensity tapers off is very high and does not do a good job defining the true boundary. A better way to define the boundary in areas where the intensity content tapers off is to use the curvature of the maximum intensity pixels (in the vertical dimension) to approximate the curvature of the true boundary. FIG. 43 provides a good example where the maximum intensity pixels 4306 (in black) approximate the shape of the true boundary. The true boundary in this case is a flat plate.

The curvature of the boundary near the end of detected edges is thus approximated by the curvature of the maximum intensity pixels in the vertical strips of the intensity map containing both the detected edges and pixels of maximum intensity. This approximation is performed only if, when dilated, the pixels of maximum intensity are all connected to each other (i.e. they belong to the same connected component). The coordinates of the maximum intensity pixels are then translated vertically such that the pixel of maximum intensity near the side of the detected edge is connected horizontally adjacent to it.

Boundary Interpolation

Figure 44:
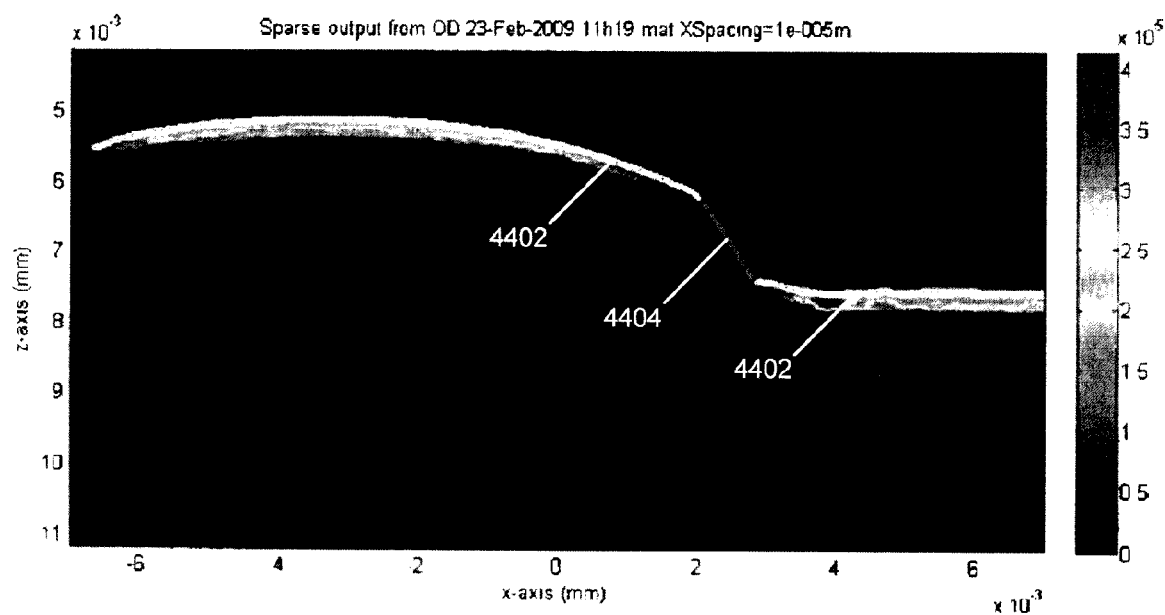
FIG. 44 is an pipe surface intensity map showing interpolation of the boundary with areas between two boundary segments extracted from the edge detection process connected with straight lines.

In areas between the definitions of the true boundary, where no true boundary edges are defined, the true boundary can be interpolated such that true boundary edges are connected together. This is the last step of the boundary definition process. FIG. 44 illustrates how the boundary can be interpolated. Areas between the boundary segments 4402 extracted from the edge detection process are connected with straight lines 4404.

Figure 45:
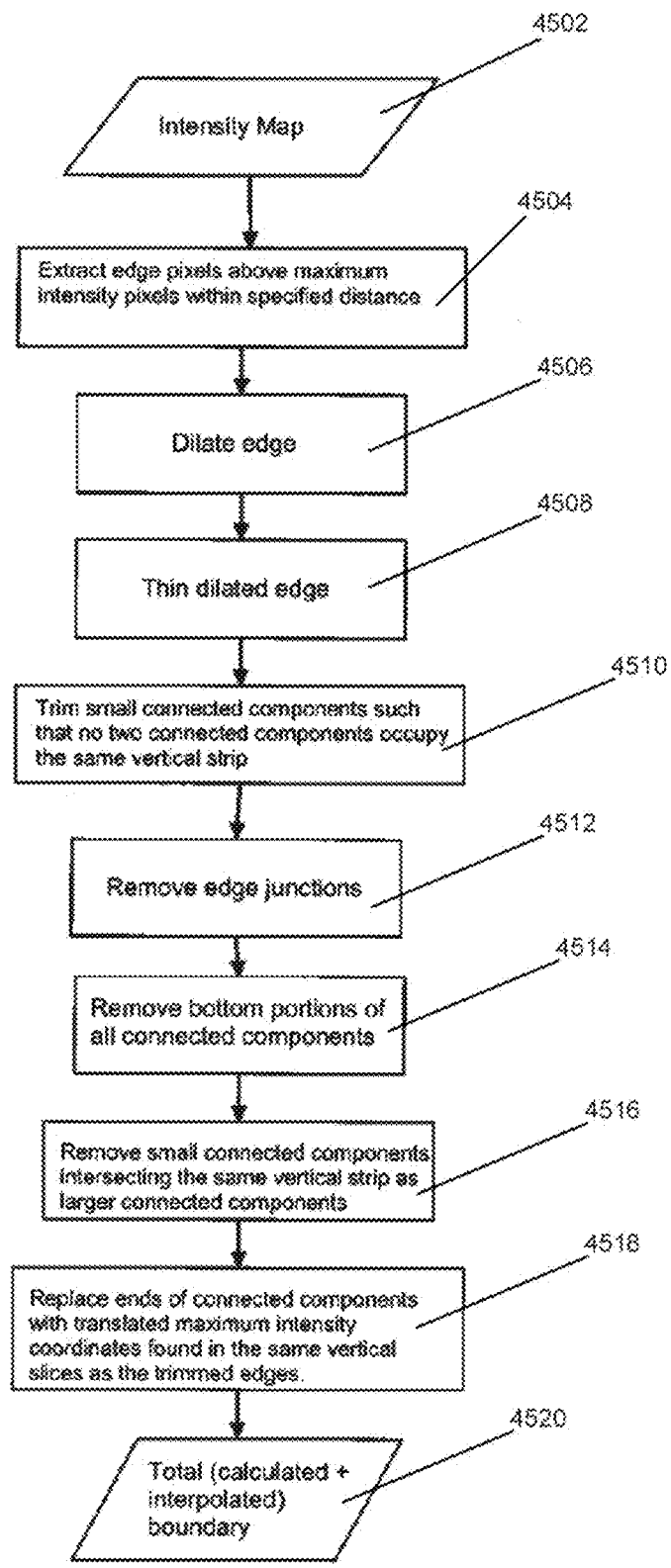
FIG. 45 is a flow chart of the sequential operation of an example algorithm for boundary recognition and definition.

The sequential operation of an example algorithm for boundary recognition and definition is shown in the flow chart of FIG. 45. The intensity map 4502 is subjected to a series of image processing algorithms, including edge detection 4504, dilation of the edge 4506, thinning of the dilated edge 4508, trimming of erroneous pixels 4510, edge junction removal 4512, removal of bottom portions of connected components 4514, removal of small connected components 4516, and horizontal end approximation 4518, finally outputting a total boundary 4520 that includes the calculated and interpolated result of the previous operations.

Figure 69:
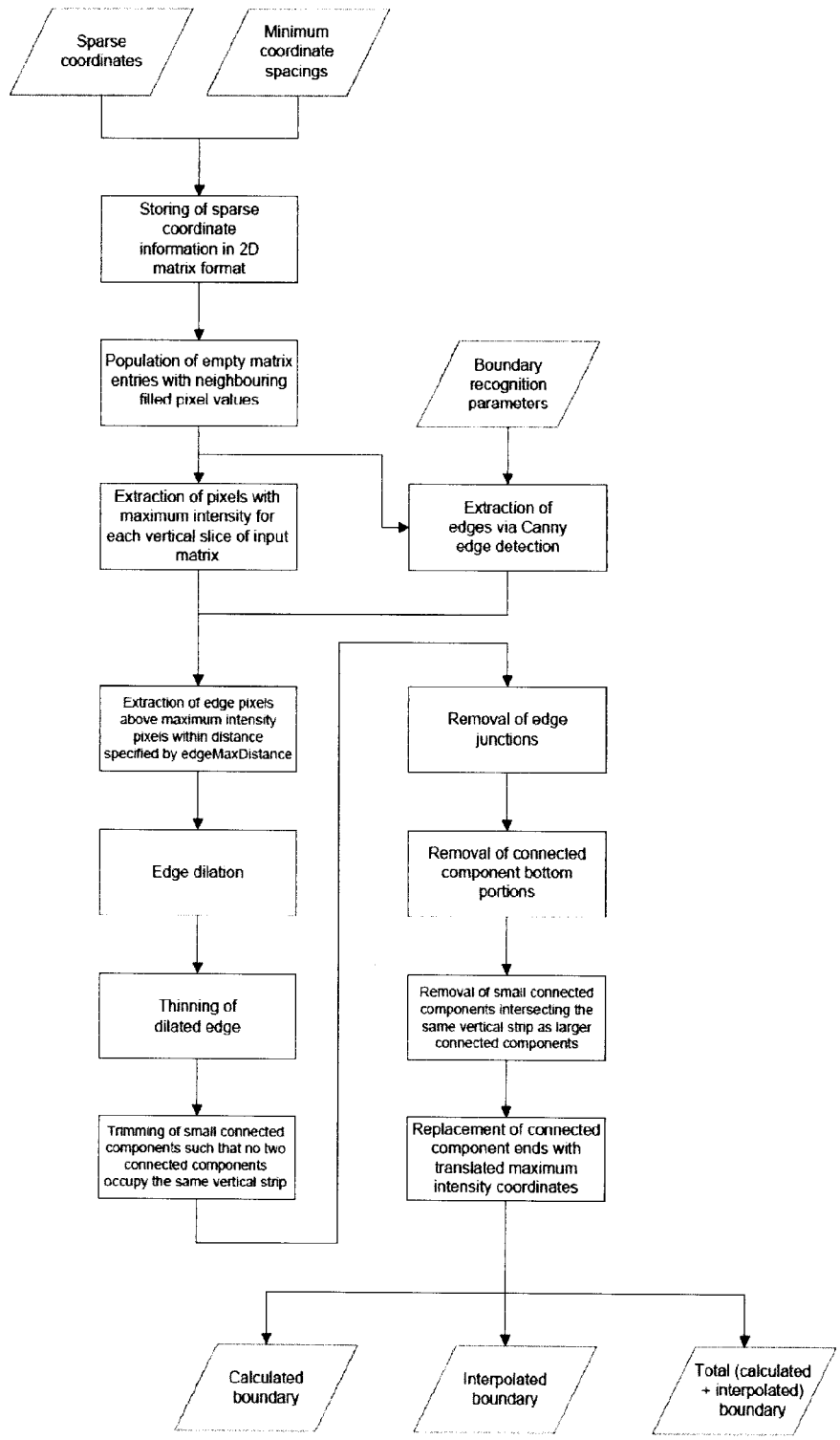
FIG. 69 is a flow chart showing the entire boundary recognition data flow according to an example embodiment.

A comprehensive flow chart showing the entire boundary recognition data flow is given in FIG. 69. Detailed descriptions of boundary recognition parameters used in an example embodiment of the system are set out in Table A4 at the end of the Description. Detailed descriptions of boundary recognition functions used in an example embodiment of the system are set out in Table A5 at the end of the Description.

Interior Focus Method (IFM)

The Interior Focus Method (IFM), like the Shifting Aperture Focus Method (SFM), is an algorithm whose purpose is to output an intensity map (an image where intensities are assigned to inspection coordinates of interest) given full matrix capture raw data and a smooth approximation of the OD boundary surface.

Once the OD intensity map has been determined and an OD surface model determined from the high-intensity OD regions 32, Fermat's Principle can be applied to model details of the inner pipe surface as well. Fermat's Principle is one of the tools by which total focusing is extended beyond the media interface (e.g. curve K 10 in FIG. 10), a technique which will be referred to as the Interior Focusing Method (IFM).

Theorem 1 (the Modern Version of Fermat's Principle) states that the path that sound takes from a point source emitter at point p, to another point q, is such that the time taken to traverse the path is a stationary value (i.e. a minimum, maximum, or inflection point).

Extending the intensity equation shown above (Equation 2) to the area beyond a media interface involves substituting the times t in the equation to those equalling travel path times whose paths experience refraction at the media interface. Fermat's Principle (Theorem 1) can be applied in solving for these times.

Since K is piecewise-smooth, $T_{ir}(K)$ has a finite number of stationary values. These stationary values are denoted as $t_{ir}^{K'}, t_{ir}^{K''}, t_{ir}^{K'''}, \ldots$ and the set of these stationary values as $T_{ir}^{K}$ where:

$$T_{ir}^{K} = \{t_{ir}^{K'}, t_{ir}^{K''}, t_{ir}^{K'''}, \ldots\} \quad \text{(Equation 4)}$$

Sets $T_{ir}^{K}$ and $T_{jr}^{K}$ are defined where i denotes element i 210 with position vector $e_{(i)}$ and j denotes element j 212 with position vector $e_j$. The set of summations of all possible combinations between elements of $T_{ir}^{K}$ and elements of $T_{jr}^{K}$ are defined as $T_{ij}^{K}(r)$ where:

$$T_{ij}^{K}(r) = \{t_{ir} + t_{jr} | t_{ir} \in T_{ir}^{K}, t_{jr} \in T_{jr}^{K}\} \quad \text{(Equation 5)}$$

By Fermat's Principle (Theorem 1), the above set contains travel path times which can be substituted in Equation 2, to extend the total focusing method to imaging areas beyond the interface 10 between media 6, 8. If the transmitter and receiver pair i 210 and j 212 are in the first medium 6, r is in the second medium 8, and K 10 is the curve which divides the first medium 6 and the second medium 8, the intensity of the image at r can be written:

$$I(r, a) = \left| \sum_{i,j \in a} \sum_{t' \in T_{ij}^{K}(r)} g_{(i)j}(t') \right| \quad \text{(Equation 6)}$$

These results can be extended to three dimensional interfaces, as Fermat's Principle holds in three dimensions. Furthermore, the results may be extended for focusing through multiple media interfaces; n media interfaces will imply sound paths that will traverse n+1 media. In this case Fermat's Principle can again be utilized to solve for the true travel paths. Some embodiments may employ these techniques to perform more complex analysis, such as scanning volumes containing more than two media or scanning in three dimensions at once rather than in a plane.

Figure 13:
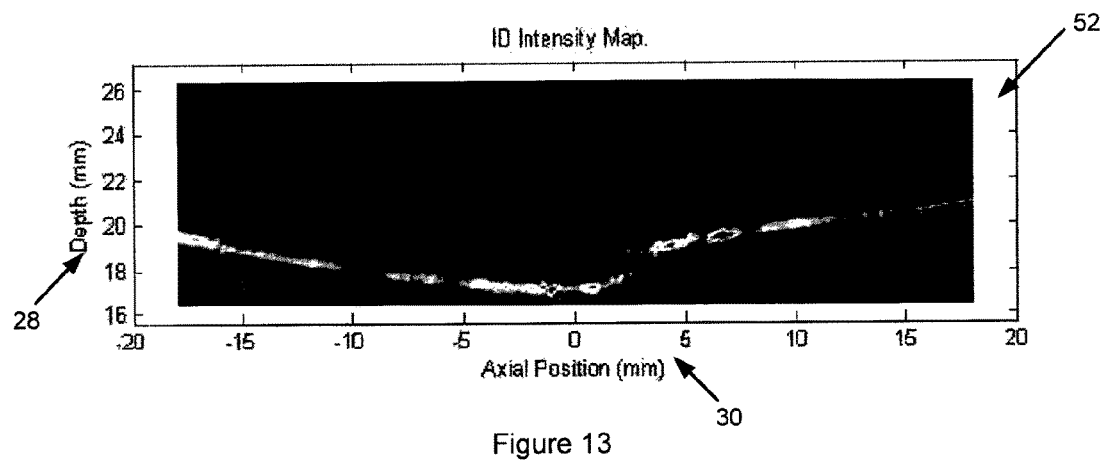
FIG. 13 is an intensity map in the scanning plane of the inner surface of a pipe wall.

IFM is applied to create an intensity map of the ID scanning plane, such as the ID intensity map shown in FIG. 13. After the ID intensity map 52 has been created, the steps of boundary recognition 1720 and boundary definition 1722 are applied using the same algorithms described above to create the ID boundary definition 1724.

Implementation of the IFM subroutine can become very computationally intensive if there are many coordinates for which corresponding intensities are evaluated. This is similar to the case for implementation of the SFM subroutine, the difference being the IFM routine is even more computationally taxing. The approach used to reduce the number of necessary computations in the IFM may be identical to the strategy employed in the SFM routine. Limiting the number of coordinates under consideration, while focusing at the appropriate density to meet inspection specifications, imposes the following focusing strategy. First, intensities of coordinates on a course grid may be calculated. The strategy that may be employed is to first calculate intensities of coordinates on a course grid.

At this point, depending on user defined parameters, the IFM subroutine may end, outputting the intensity map to the boundary detection subroutine, or proceed to define new coordinates for which to assign intensities. If the latter course is taken, newly defined coordinates will be positioned around coordinates with high intensities already assigned to them. The cutoff intensity for coordinates of which newly defined coordinates focus around is defined in some embodiments by the vector zoomPercentage (see Table A10). Once the new coordinates have been defined, again depending on user defined parameters, the SFM subroutine may exits, or may proceed to further focus around coordinates of high intensity. The process of identifying high intensity coordinates and then refocusing around them can be executed an arbitrary number of times, and may be specified by the user.

One cycle of the refocusing process is illustrated in FIG. 19. Coordinates spaced coarsely apart are represented as either white or black circles. The white circles represent those coordinates whose respective intensities are below the cutoff intensity for which new coordinates are defined. Conversely, the black circles represent those coordinates whose respective intensities exceed the cutoff intensity for which new coordinates are defined. The gray circles represent newly defined coordinates around high intensity coordinates. If the gray circles are defined on iteration i+1 of the coordinate definition and intensity assigning process, dx(i)/dx(i+1)=dz(i)/dz(i+1)=4 for the example illustrated by FIG. 19.

Figure 71:
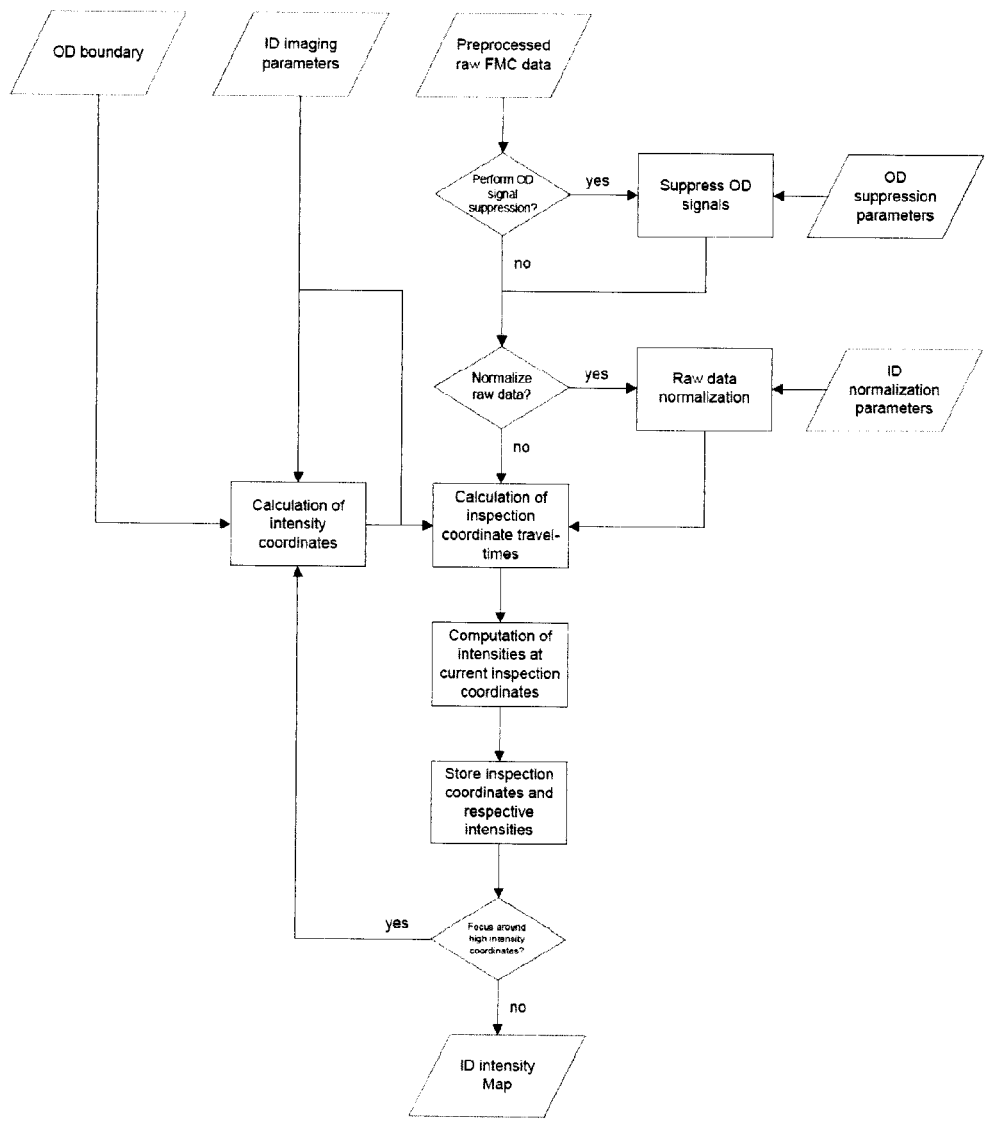
FIG. 71 is a data flow chart for the Interior Focusing Method process.

FIG. 71 provides a full data flow for the IFM process. Detailed descriptions of ID imaging parameters used in an example embodiment of the system are set out in Table A10 at the end of the Description. Detailed descriptions of ID imaging functions used in an example embodiment of the system are set out in Table A11 at the end of the Description.

Boundary Definition and Smoothing

The boundary output from the boundary recognition procedure described above may be susceptible to noise. Two main factors contribute to this noise. The first is due to the imaging of aberrations such as grating in the intensity map calculated via SFM. The second is due to the quantization of the intensity map grid. Errors (noise) can arise in a definition of a quantity due to a quantization of its state space.

To minimize the effects of noise in determining true boundary (either OD or ID) coordinates, standard filtering techniques may be employed. The boundary outputted from the boundary recognition algorithm may in some embodiments be filtered via two successive processes. The first filter used to eliminate noise from the input data may be a median filter of variable window size. This has the effect of removing high frequency noise from the input coordinates. The next filter used may be a Savitzky-Golay filter. This filter reduces quantization noise by approximating the input coordinates by an unweighted linear least-squares fit using a polynomial of a given degree. Utilization of polynomials of higher degrees makes it possible to smooth heavily while retaining data features of interest.

To initially eliminate noise from the calculated boundary, a median filter may be employed. Median filters implement a sliding window to a sequential data sequence, replacing the center value in the window with the median value of all the points within the window. Such a median filter may be chosen for its combination of good noise elimination coupled with its edge-preserving features. For both the OD algorithms and the ID algorithms, the window width of the algorithm may be configured by a user in some embodiments. In some embodiments, the window width may be set to 5 mm by default.

Savitzky-Golay smoothing filters may also be used due to their superior performance in smoothing out a noisy signal whose frequency range (without noise) is large, as the corroded regions under a pipe weld cap may be seen to be with their potentially sharp edges. Savitsky-Golay filters perform a least-squares fit of a windowed set of consecutive data points to a polynomial and take the calculated central point of the fitted polynomial curve as the new smoothed data point. A set of convolution integers can be derived and used as weighting coefficients for the smoothing operation, a computationally-efficient process. This methodology is exactly equivalent to fitting the data to a specified polynomial. The smoothed data point $(y_k)_s$ by the Savitsky-Golay algorithm is $$(y_k)_s = \frac{\sum_{i=-n}^{n} A_i y_{k+i}}{\sum_{i=-n}^{n} A_i}$$

where $A_i$ are the convolution integers, and the data window goes from $-n$ to $n$.

In some embodiments, the user-adjustable parameters for the Savitsky-Golay filters used in the OD/ID smoothing are:
1. Smooth Width: The smoothing window width expressed in mm. The algorithm uses the appropriate "X Spacing" parameter to determine the window width in elements:

$$\text{Number}_{elements} = \frac{\text{Smooth Width}}{X \text{ Spacing}}$$

2. Smooth Order: The polynomial order to be used in the Savitsky-Golay algorithm. It is generally smaller than the smoothing window number of elements. A typical value for Smooth Order is 4.

Figure 70:
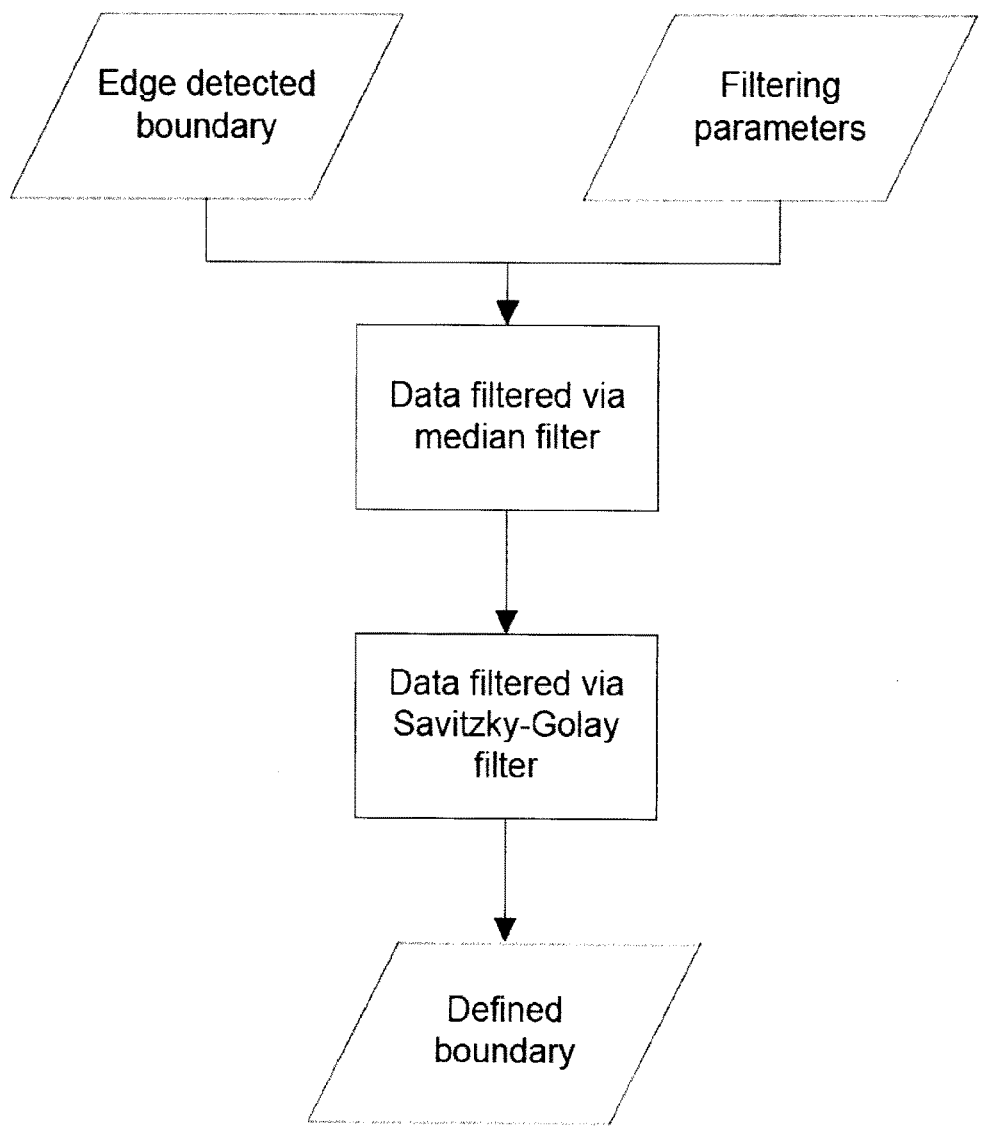
FIG. 70 is an example data flow for boundary definition.

An example data flow for boundary definition by the above processes is shown in FIG. 70. Detailed descriptions of boundary definition parameters used in an example embodiment of the system are set out in Table A6 at the end of the Description. Detailed descriptions of boundary definition functions used in an example embodiment of the system are set out in Table A7 at the end of the Description.

IFM Outer Diameter (OD) Boundary Preparation

The interior focus method (IFM) calculates travel times from probe array elements to points under the outer diameter via Fermat's Principle. Due to a change in the refractive index at the OD, refraction of ultrasonic waves will occur at this interface. Very small, high frequency variations in the definition of the OD surface will invite a large number of travel path solutions between probe array elements and inspection points under the OD, intersecting small regions in the defined OD surface. These travel path solutions are due to either true high frequency variations in the OD surface, high frequency noise introduced into the OD definition, or a combination of both. The signal processing techniques that are described below serve to both to eliminate erroneous travel time solutions caused by high frequency noise content in the input OD boundary and to reduce IFM computation time.

While smoothing the defined OD surface can eliminate spurious travel path solutions due to high frequency noise, it is not obvious what effect this will have on travel path solutions induced by true high frequency variations in the OD surface. Eliminating high frequency content of the defined OD surface may reduce the number of travel paths with solutions very close to each other, but will generally preserve effectively distinct solutions. For example, a series of travel path solutions 4.52 μs, 4.55 μs, 4.48 μs, 6.21 μs, 6.18 μs, 6.23 μs could feasibly be reduced to 4.53 μs and 6.22 μs. Programmatically, utilizing the latter travel time solutions may produce similar intensity maps output out of the IFM subroutine as those that can be produced utilizing the former travel time solutions, since travel times of interest are retained. Features of interest in the intensity map will be preserved, with the added benefit of reduced computation time of the IFM subroutine, due to a fewer number of computations involving travel time solutions being executed.

Thus, the smoothing operations may serve to eliminate the effects of noise with a beneficial side effect. Smoothing of the OD boundary serves firstly to eliminate erroneous travel time solutions due to high frequency noise, while reducing the number of travel time solutions to those that are effectively distinct. The smoothing methods employed on the boundary of the OD may include a median filter followed by a Savitzky-Golay filter. They may be the same filters used for the purpose of boundary definition. These filters have the effect of eliminating high frequency content while preserving data features of interest. Since the utilization of these filters for preparation of the OD boundary as input into IFM has objectives different than the utilization for boundary definition, filtering parameters used may be different. Larger window sizes may be used for the Savitzky-Golay filter in IFM OD boundary preparation than those used in OD boundary preparation, since preservation of high frequency content in the OD boundary is not desired.

Finally, the smoothed data may be downsampled. This has the primary effect of reducing computation time necessary to calculate travel times via the IFM subroutine, while retaining travel time solutions of interest.

Figure 67:
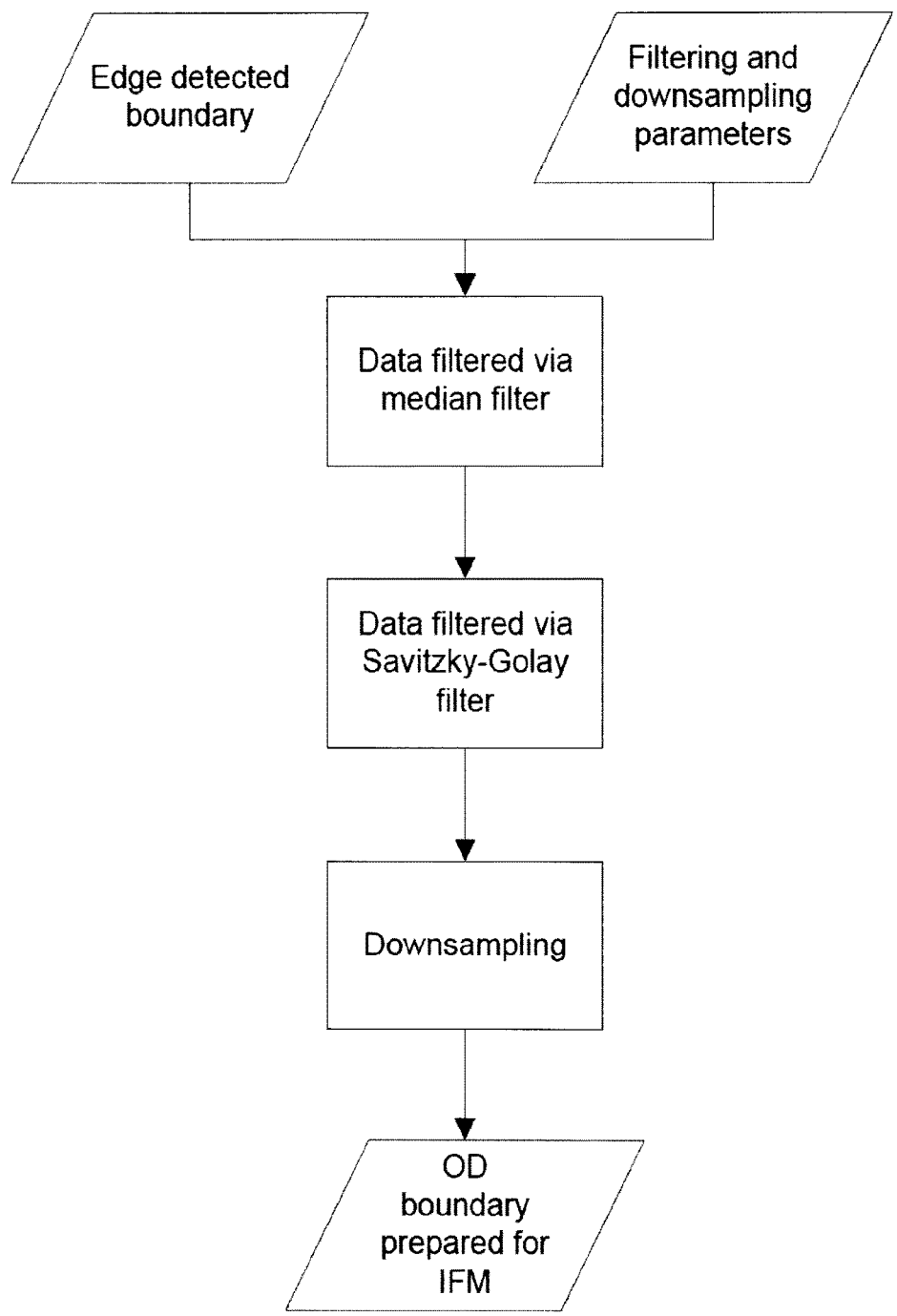
FIG. 67 is an example data flow for IFM OD boundary preparation.

An example data flow for IFM OD boundary preparation by the above processes is shown in FIG. 67. Detailed descriptions of IFM OD boundary preparation parameters used in an example embodiment of the system are set out in Table A8 at the end of the Description. Detailed descriptions of IFM OD boundary preparation functions used in an example embodiment of the system are set out in Table A9 at the end of the Description.

Adjustable Mirror

Figure 46:
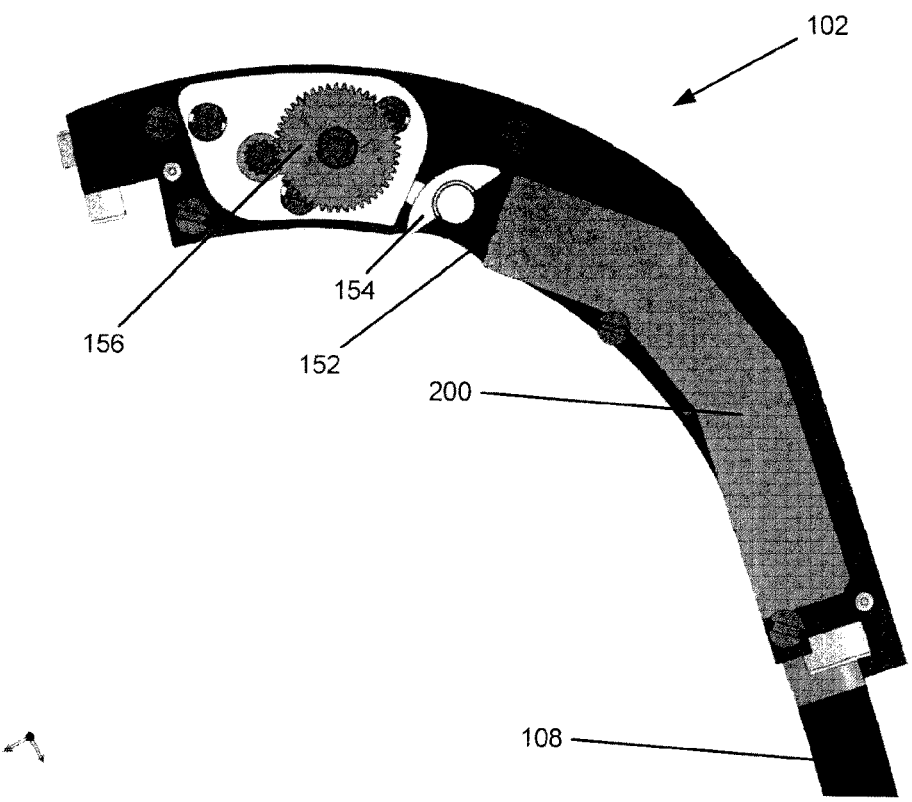
FIG. 46 is a side view of an ultrasound probe carrier showing an adjustable reflector, for use with the example manipulator of FIGS. 1 to 6.
Figure 47:
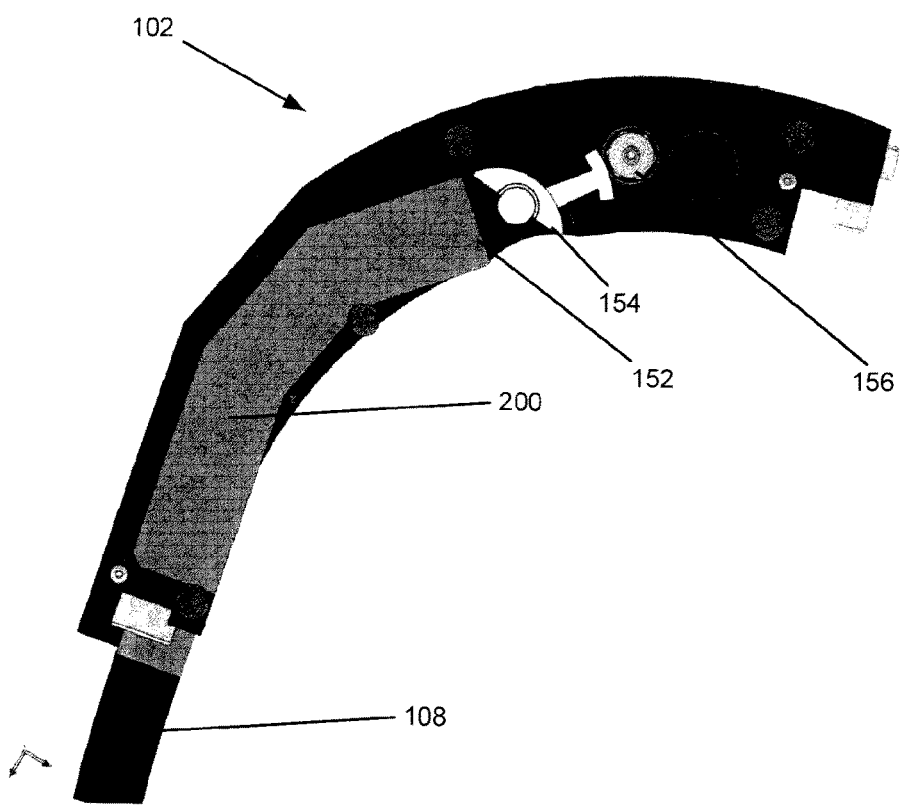
FIG. 47 is a side view of the ultrasound probe carrier of FIG. 46, shown from the opposite side.

Some example embodiments may be able to adjust the angle of projection of the ultrasound probe array 200 relative to the surface being scanned. For example, when scanning a pipe wall, some embodiments of the manipulator 100 may make use of an adjustable mirror 154 that reflects ultrasound projected from and reflected to the probe array 200. FIGS. 46 and 47 show an example embodiment of the carrier 102 having an adjustable mirror 154. The ultrasound probe array 200 projects ultrasound from a linear array of elements arranged on its active face 152. Ultrasound waves are projected toward the mirror 154, whose angle can be adjusted by a mirror adjustment assembly 156 including a motor. By projecting ultrasound from one or more elements and sensing with one or more elements at different angles of reflection, it is possible to optimize the angle of the mirror to ensure that the ultrasound waves are being projected normal to the pipe surface. In some embodiments, this optimizing procedure may be performed prior to each frame of FMC data collection. The mirror adjustment assembly 156 may be controlled by the external controller via the probe data connectors 108.

In embodiments having a mirror 154, the transducer is positioned to fire tangentially instead of radially to the inspection surface. The mirror placement is designed to optimize the range of alignment accommodation while minimizing the added UT beam transit distance to the inspection surface.

The manipulator 100 may also be controlled by software to adapt the change in inspection step size given possible changes in mirror angle. The control of the mirror may be achieved in some such embodiments by pulsing a group of elements 202 and summing their response. The amplitude of the response is monitored after a series pre-defined step increments. Should the response level drop below a user defined threshold, the module controlling the manipulator 100 will pulse the user defined control aperture while driving the mirror 154 through a defined range of angles at a defined step size. The system sums the responses at each step and then drives the mirror to the angle corresponding to the peak amplitude.

The user interface used in such an embodiment may have a GUI where all relevant control variables are entered. The user may have the capability to change the tracking parameters during a data acquisition scan as to effect an optimal control region on the inspection surface.

Further details on optimizing the scanning angle using the adjustable mirror are provided below in the description of the data acquisition procedure as applied to pipe weld inspection.

Application to Pipe Weld Inspection

Figure 14:
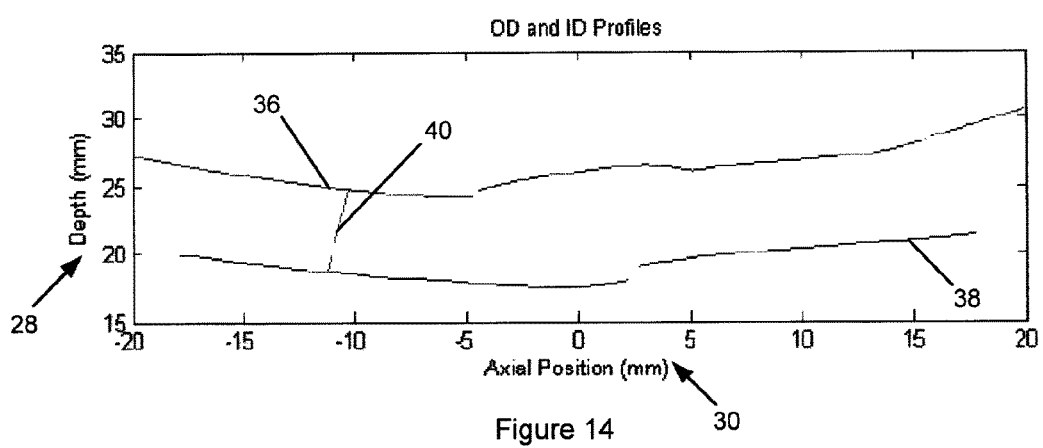
FIG. 14 is a graph of the outer surface and inner surface of a pipe wall derived from intensity maps in the scanning plane.

Once the OD and ID surface profiles have been modeled, they can be used to determine structural characteristics of the pipe wall or other scanned object. For example, the OD profile 36 and ID profile 38 for a single transmit-receive cycle are combined in the graph shown in FIG. 14. By juxtaposing these two profiles, information about the thinnest point 40 in the scanned portion of the pipe wall can be assessed and made visible to a user.

Figure 48:
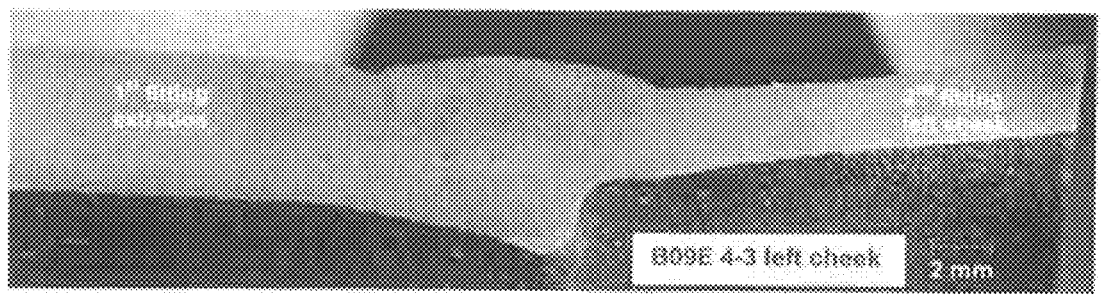
FIG. 48 is a cross-sectional side view of a pipe wall showing uneven thinning.

Thinning of feeder pipe material adjacent to and within the weld area is a concern for power generating stations and other industries Thinning may be found around the entire circumference of the joint with some highly localized areas directly under the weld cap. The location of these areas may not be predictable due to the association with the weld root condition. FIG. 48 shows an example of a pipe wall exhibiting thinning.

A procedure is described below which provides a method and requirements for performing thickness measurements on heat transport feeder piping welds at nuclear power generating stations, using a Micropulse™ ultrasonic inspection and data acquisition system. This example embodiment is illustrative, and the methods and devices described may be implemented in various embodiments and applied various contexts.

The inspection procedure described below is intended to detect localized and broadly based wall thinning in the regions adjacent to circumferential welded joints in feeder piping. This procedure applies to various pipe sizes.

Figure 49:
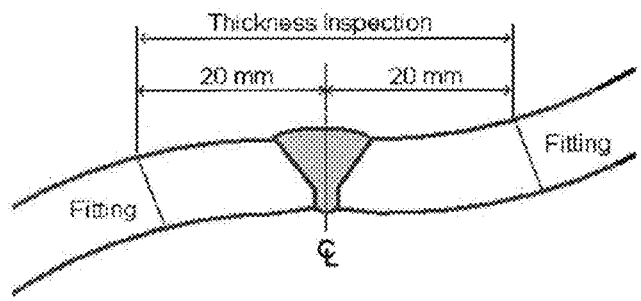
FIG. 49 is a cross-sectional side view of a pipe wall at a fitting to fitting weld showing a zone inspected for thickness.

As shown in FIG. 49, the region of inspection is 20 mm on either side of the weld centre line. However, geometric limitations may constrain the ability to achieve this coverage. This inspection records all ultrasonic signals transmitted from each element to all possible receiving elements. Each element in the array is fired in sequence. Thus, for a 128 element linear array, each of the 128 elements that has fired has 128 receptions for a total of 16,384 separate A-scans. This process is repeated at each location as specified in the inspection sequence.

The data recorded is then submitted for analysis. The data analysis software produces OD and ID profiles of each inspection data set. The data sets are acquired at discrete circumferential locations. Together the series of profiles around the feeder constitutes the results of the inspection. A separate table records the minimum distance between the OD and ID profiles for each circumferential location, the axial location of the minimum in the slice and the circumferential position of the slice.

Figure 50:
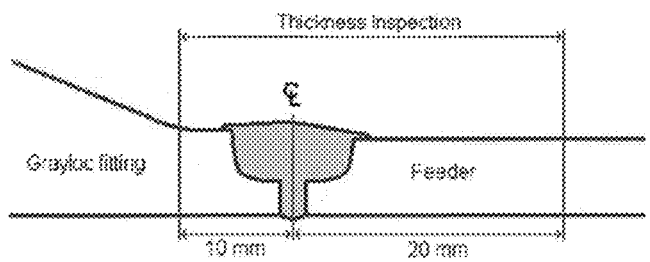
FIG. 50 is a cross-sectional side view of a pipe wall at a Grayloc™ fitting to fitting weld showing a zone inspected for thickness.

Special circumstances and exceptions to the procedure may exist. For example, hot spots or high local fields may create a situation where operators cannot access the work area. In addition, in the case of Grayloc™ fitting to pipe welds the inspection coverage may be modified to collect a zone spanning 10 mm on the Grayloc™ side of the weld centre line to 20 mm on the fitting side of the weld centre line, as shown in FIG. 50. (In the context of this embodiment, a Grayloc™ fitting refers to a conical pipe fitting with its narrow end matching the diameter of a straight pipe section.)

Definitions

The following definitions are used within the context of pipe weld inspection as described below.

FMC: Full Matrix Capture. Ultrasonic data collection strategy in which each element in the transducer is individually pulsed while all elements receive. This is repeated for each element in the transducer until all elements have been fired. This strategy creates a data array of n by n where n is the number of elements in the transducer. As a consequence the data files for a FMC inspection is significantly larger than for the equivalent conventional (e.g. phased-array) technique at the same resolution.

Home Position: Circumferential location of the inner rotating ring such that the manipulator may be safely unlocked from its closed position. Home position is indicated in both the VIM and the software as identified by the Hall sensor on the manipulator.

Main diagonal: A group of send-receive elements in the data collected using FMC where each transmitting element is its own receiver. The main diagonal view of the FMC data set is identical to the conventional linear electronic B scan. The main diagonal view is the default view of the FMC data B scan.

Matrix: Data structure created when using the FMC data collection strategy. If the columns of the matrix are assigned to identify the transmitting element, then the rows of the matrix correspond to the receiving elements. Each element of the array then corresponds to an A scan related to that transmitter receiver pair. For example: a combination of transmitting on element 17, receiving on element 32 would produce an A scan that would be located under the 17th column on the 32nd row of the FMC data matrix.

Start Position: Circumferential location, with respect to the manipulator, where the scan is initiated. The start location may correspond to the home location or can be offset from the home location.

TFM: Total Focus Method. Generic name for a variety of automated data analysis strategies that use the data created via the FMC method. TFM relies on summing up the amplitude values in a range of time indices in A scans from various transmitter-receiver combinations. Where valid surfaces exist, the amplitudes constructively interfere to image the surface. Where no such surface exists, the amplitudes destructively interfere forming no image. TFM is also described as being equivalent to focused phased array throughout the entire inspection volume.

Abbreviations and Acronyms

The following abbreviations and acronyms may be used within the context of pipe weld inspection as described below.

| A Scan | Time-Amplitude plot for a specific Tx-Rx pair |
|---|---|
| B Scan | Collection of A scans across the inspection array, in this case transverse to the weld, where amplitude is represented in gray or colour scale |
| DP | Digitization Point - point along the time axis of the A scan |
| feeder | Pipe carrying heavy water coolant to or from the individual fuel channels |
| FMC | Full Matrix Capture |
| Inspection Array | Multi element transducer used for FMC data collection |
| ID | Inside Diameter |
| NEOVISION | Custom UT data acquisition and analysis application for FMC data sets |
| NPS | Nominal Pipe Size |
| OD | Outside Diameter |
| Tmin | Minimum wall thickness |
| TFM | Total Focus Method |
| TSSA | Technical Standards & Safety Authority |
| UT | Ultrasonic Testing |
| WPIT | Weld Profile Inspection Tool |

Data Acquisition

FMC inspection superimposes a probe trajectory of a cylindrical geometry on the weld configuration. Depending upon the nature of the joint and the placement of the manipulator over the joint, some distortion of the OD and ID signals can occur. Areas where this may occur are the cheek areas of straight to bend geometries or Grayloc™ to bend geometries. A possible remedy for this is to attempt re-positioning the manipulator over the joint with the intent of optimizing the signals in the regions where distortion is experienced.

There are two types of obstructions that limit inspection of welds. The first type is adjacent structures which block installation of the tool in the desired inspection area. In this event the inspection area may be inaccessible. A second type of obstruction exists where the manipulator is prevented from achieving full rotation due to intrusion into the manipulator path by adjacent structures. The data acquisition software may have an option where, should an obstruction be detected, the manipulator will drive to the scan origin and then acquire data in the opposite direction until either full coverage is obtained or the manipulator again contacts the obstruction. In the latter case the portion of the circumference where no data has been obtained may be noted as access restricted.

Figure 51:
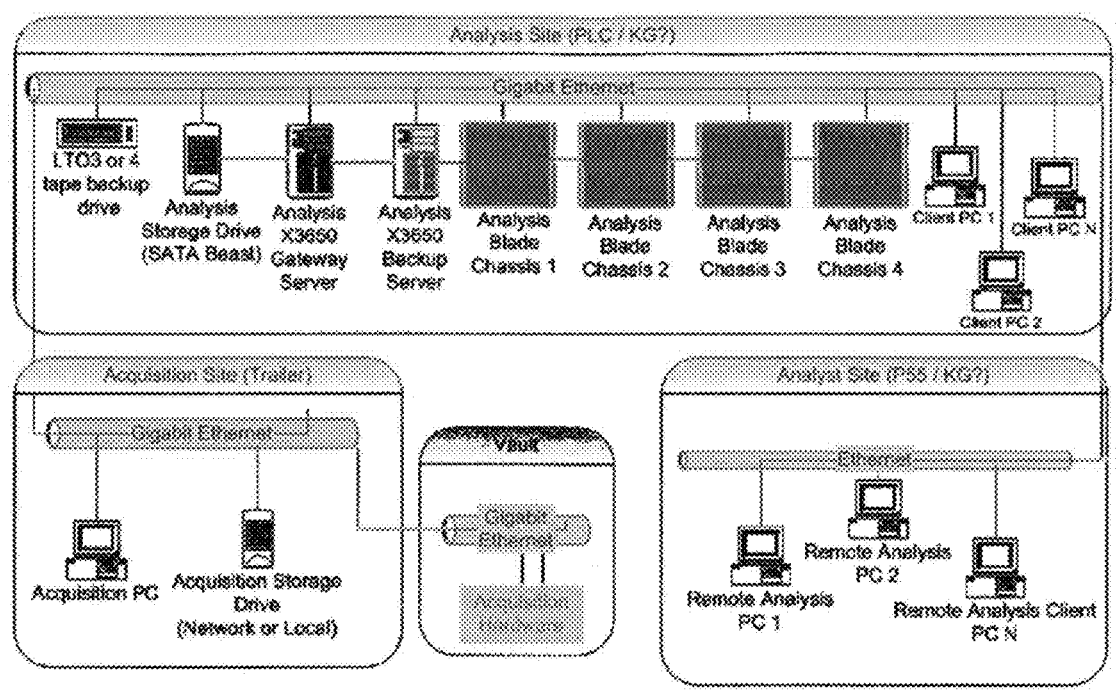
FIG. 51 is a network diagram showing remote data acquisition and analysis computers according to an example embodiment.

FIG. 51 shows an example configuration of the various data systems used in collecting and processing the inspection data. The inspection system as a whole is divided into two separate spheres; the data acquisition aspect and the data analysis aspect. The UT (Ultrasound Testing) data generated during data acquisition in the vault 5002 is collected, reviewed and recorded at the acquisition site 5004. After the recording process, the data is exported to the analysis site 5006 where the analysis blade system 5008 resides. The export process will take a few minutes (2-3) due to the file size and the network speed.

Analysts may be able to remotely access the analysis site 5006 such that data need not be transferred to the analyst machines 5010. The analysts evaluate the scan data to set processing parameters to appropriate values prior to submitting a job. Once the job has been processed, the analysis operator will be able to review the profiles and associated intensity maps.

Figure 52:
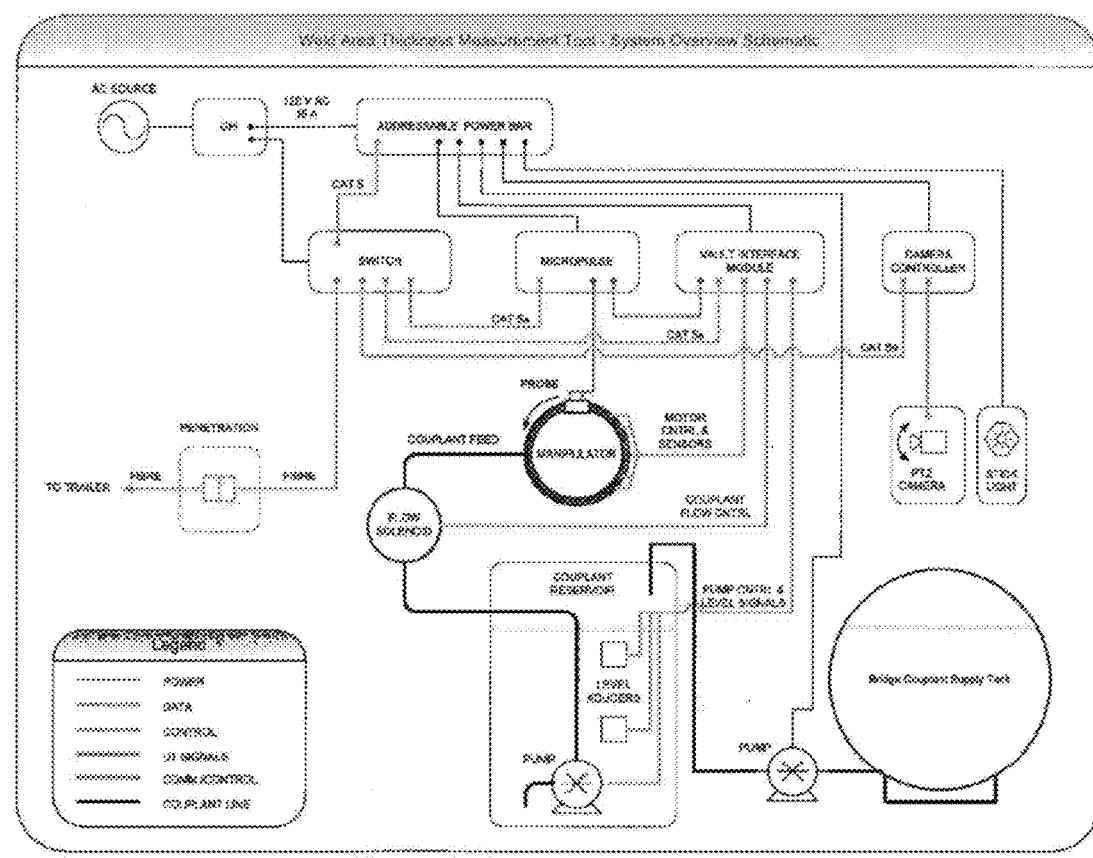
FIG. 52 is a network diagram showing the relation of local hardware components used at the inspection site according to an example embodiment.

A simplified diagram of the equipment configuration in the vault 5002 is given in FIG. 52.

Figure 53:
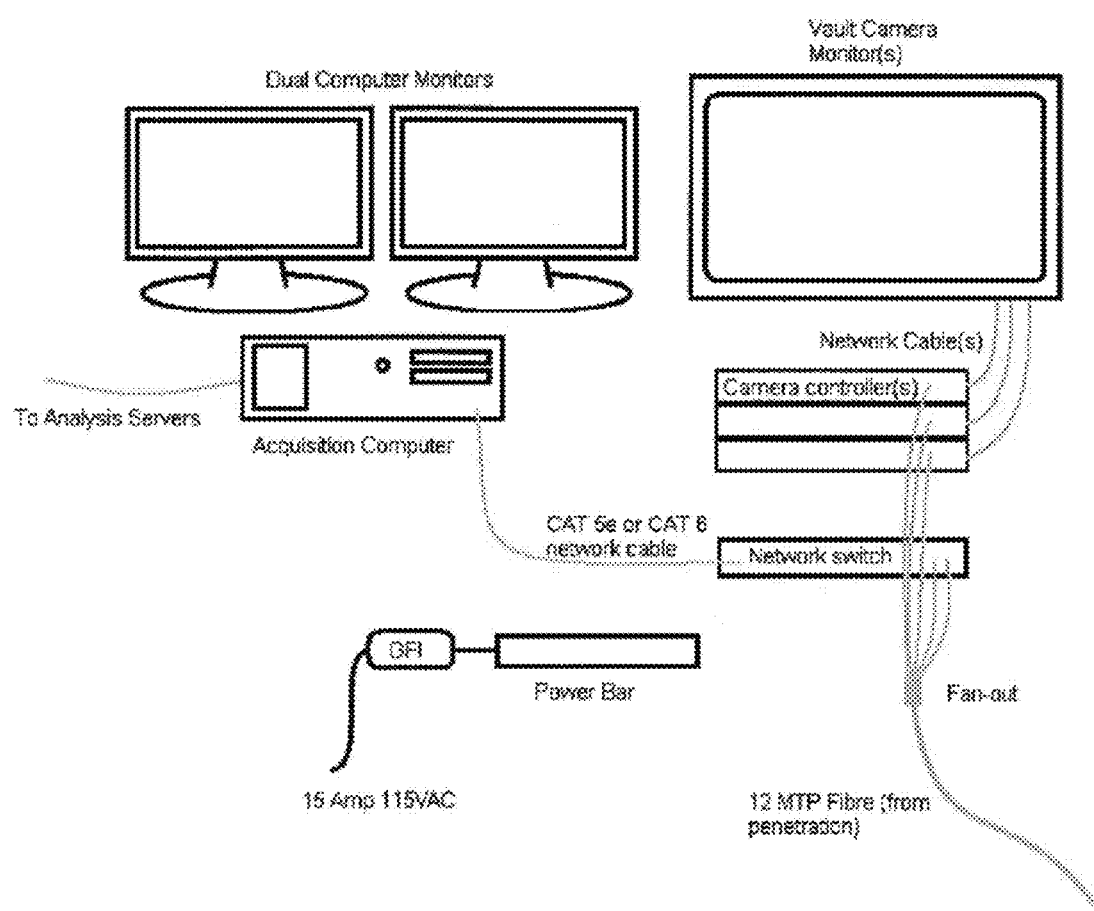
FIG. 53 is a diagram of the equipment configuration at the remote acquisition site according to an example embodiment.

A diagram of the equipment configuration at the trailer/remote acquisition site 5004 is given in FIG. 53. If 12 fibre MT has not been installed between the acquisition site 5004 and the acquisition hardware in the vault 5002, this fibre may be run to the from the acquisition site 5004 to the penetration.

The following is a list of equipment used for data acquisition under this example:

| Quantity | Item | Description |
| --- | --- | --- |
| 3 | Micropulse ™ 5PA | Data Acquisition Instrument - 128 channels with Gigabit Ethernet interface, Firmware version P1 4.5.1.29 and P2 4.5.0.10 or latest qualified release |
| 3 | Vault Interface Module | Interface unit for manipulators, Micropulse ™ and peripherals |
| 2 | Acquisition computer | 4 GByte memory, Core2 Duo 23 GHz or above, 32 bit Windows XP, 500 GByte HDD, Gigabit Ethernet interface, Dual 19" monitors |
| 3 | Neovision ™ software | Data acquisition software 1.0 R0 or most recent qualified release |
| 3 | Manipulator 2" | |
| 3 | Manipulator 2.5" | |
| 3 sets | Mounting Brackets for 0 degree configuration | |
| 3 sets | Mounting Brackets for 6 degree configuration | Provided by Kinectrics ™ |
| 3 | Array Transducer | Custom 128 elements, 7.5 MHz, 0.27 mm pitch, with 8 m cable and Hypertronix ™ connection |
| 3 | Temperature sensor | |
| 2 | Reference specimen 2" 0 degree configuration | |
| 2 | Reference specimen 2.5" | |
| 2 | Reference specimen 2" 6 degree configuration | |
| 4 | Reference Block stand Fibre Optic Cables | 12 fibre with MT connections for station side and vault side (lengths required vary depending upon configuration) |
| 2 | Network Switch | Should support Gigabit standard |
| 3 | CAT 5e or CAT 6 Ethernet cable | Use of CAT 5 cable is not generally recommended |
| 1 | Ethernet addressable power bar | |
| As required | Programmable headsets | Communications sets to be set to a dedicated channel |
| 1 | Couplant Pump | Submersible type with tubing |
| 1 | Water container | Large capacity - 60 litre suggested |
| 1 | Flow Control Module | |
| As required | Trailer/Remote vault camera monitor | As per current practice |
| As required | Vault camera control unit | As per current practice |
| As required | Containment side camera controller unit | As per current practice |
| As required | PTZ camera | As per current practice |
| 1 | Penetration insert | Universal or SG penetration (should support MTP fibre) |
| 1 | Stick Light | |
| 2 | GFCI | 15 Amp Fusible Link to U-ground |
| As required | Adapter | Twist lock to U ground |

Demineralised water for use as couplant is generally allowed to sit for a minimum of 48 hours, preferably 60 hours prior to use. This is to permit gases dissolved in the water to condense out. Heating the water to 50 C and then allowing it to cool will accelerate this process. If the water is not allowed a period to de-aerate it is very likely bubbles will nucleate on both the feeder and transducer surfaces. The bubbles will continue to grow and may impair the quality of the scan data. Swabbing a thin layer of gel couplant on the probe face may reduce the tendency for bubbles to form, however the couplant will dissolve in time with exposure to water.

As an alternate to having the water sit for an extended duration another method is available. Effective de-aeration may be performed by spraying the water into a suitable container using a common garden nozzle. The nozzle should be set to a fine pattern. The pressure drop at the nozzle causes the air to separate from the water. Properly done, the water should be ready for immediate use.

A catenary cable containing breathing air hose(s), 120 VAC power and communication fibre may be prepared and tied off at the platform with the other end tied off at a suitable point on the vault floor. The fibre may be connected to the penetration, the air hose(s) to a dedicated breathing air header, and the 120 VAC to a GFI and designated receptacle.

On the platform the fibre may be terminated at the switch and the power at the addressable power bar. The platform equipment may be mounted on a suitable cart or common instrument rack.

Instrument Calibration

Conventional UT data collection instruments may benefit from periodic calibration when employing techniques that utilize signal amplitude as a means to detect, discriminate and size indications. Conventional normal beam techniques as applied for feeder thickness measurement rely upon the accuracy and stability of the instrument time base. The time base of digital instrumentation is dependent upon the system clock, devices that are known for their long term stability. As such there may be no need to perform annual calibration of the instrument since signal amplitude is not a factor. The embodiments discussed in this application similarly do not rely upon signal amplitude for measurement; therefore periodic instrument calibration is not mandatory.

Calibration may be advisable when significant differences are noted when connecting a transducer to two separate instruments given the same set-up parameters. The data collection instrument may be calibrated at such times when replacing components, upgrading hardware or repairs to the instrument are necessary.

Transducer Characterization (Maintenance)

Transducers may be characterized upon receipt from the manufacturer or when first placed into service. Transducers may then be characterized at yearly intervals following being placed into service. The characterization activities may be conducted by qualified maintenance technicians. The characterization tasks are considered to be part of the system maintenance activities and are not part of the calibration activities during the inspection. The manufacturer's report for the transducer may be referenced during the characterization. Correct processing of inspection data depends upon accurate measurements of probe parameters. These parameters include:

(1) Element Functionality Check

The NEOVISION™ application has a feature which introduces a series of linearly varying delays into each channel that when viewed appear like a saw tooth pattern. This feature is the Probe Element Test and is found under the UT Calibration tab. A quick check of the main diagonal B scan response will highlight any missing elements. The operator may use the cursors to identify the channel number of the missing element(s). The channel numbers of any missing element(s) may be recorded in the maintenance record.

(2) Transducer Delay

The transducer can be evaluated on the reference block; however, slight misalignment can introduce errors in the delay measurement. Given the clearance dimensions in the various components of the manipulator, it is difficult to ensure precise location of the probe with respect to the reference block surface. For the purposes of this inspection, the transducer delay is measured separately on a metrology fixture. This value is recorded and is subsequently confirmed to be within an acceptable range once the transducer is mounted in the manipulator and measured on the reference block.

(3) Element Delay

In addition to the overall transducer delay, the delay of each element may also be evaluated. Transducer elements have been found to vary in delay significantly across the face of the transducer, in some cases up to ½ cycle. Significant variation will introduce error into the subsequent processing of inspection data.

(4) Frequency Spectra Test

The frequency spectra test acquires the individual responses of the elements from a defined target and then performs the Fourier transform on a segment of the A-scan. The resulting frequency spectrum is compared to the original as provided in the manufacturers report. This value is recorded and is subsequently confirmed to be within an acceptable range once the transducer is mounted in the manipulator 100 and measured on the reference block during maintenance.

(5) Pulse Duration Test

The pulse duration test is associated with the frequency spectra test. This particular test involves measuring the duration of the reflected waveform at both 6 dB and 20 dB drop points. This value is recorded and is subsequently confirmed to be within an acceptable range once the transducer is mounted in the manipulator 100 and measured on the reference block during maintenance in the rubber area.

(6) Beam Orientation

This test verifies the direction (angle) of the emitted beam with respect to the passive and active planes of the transducer. The beam is generally to be within 0.5 degrees of the vector normal to the transducer surface. Transducers found to be outside of this specification may not be suitable for FMC inspection.

Additional Tests (Maintenance)

This series of tests and steps are not associated with the transducer alone; however, they do affect subsequent data analysis processes. It is intended these checks be performed at a maintenance facility or in a properly equipped rubber area.

(1) Water DAC Curve

The water DAC (Distance Amplitude Curve) is created by scanning over the water column steps of the reference tube while the DAC curve is inactive. The gain is adjusted such that the interface echo does not exceed 80% FSH (Full Screen Height) on any of the steps. The data file is saved and then analyzed.

The maintenance technician using the cursors on the A-scan records the time of arrival and peak amplitude of the interface signal. The steps are measured in series from nearest to furthest. The amount of gain needed to raise the interface signal to 80% FSH is calculated and entered along with the time of arrival of the peak in the DAC table.

Figure 54:
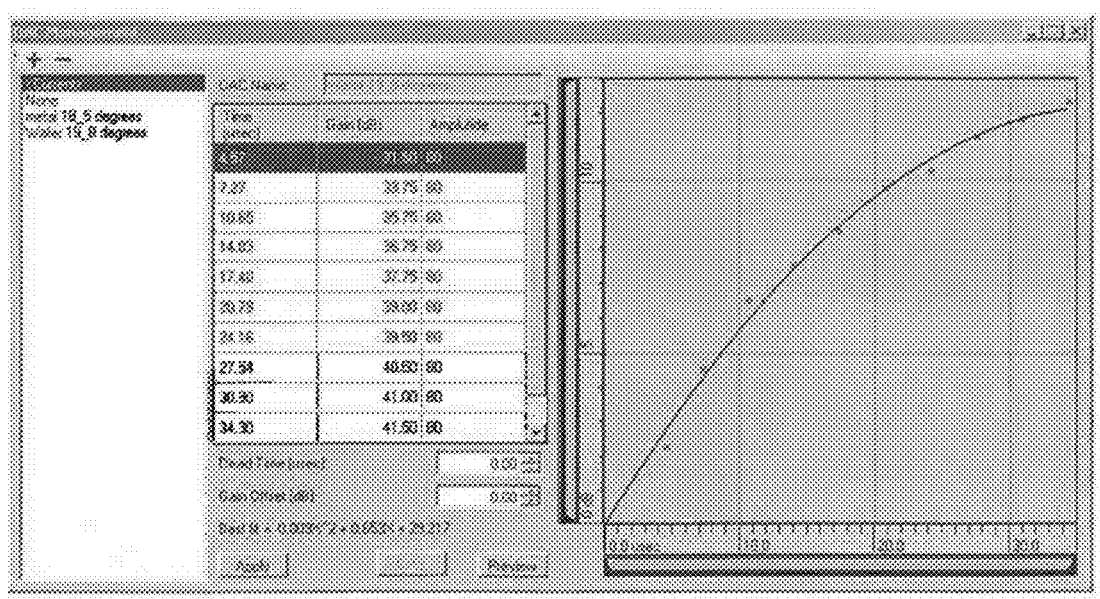
FIG. 54 is an example Distance Amplitude Curve (DAC)

A series of points is created and a best fit curve is plotted through the data series. Any significant outliers to the curve may be investigated for anomalies (potential air bubbles). See FIG. 54 for an example of a DAC curve. The Water DAC is then activated and a final scan of the reference tube is conducted to ensure all interface signals are at 80% FSH regardless of water column distance. If there is any deviation beyond 1.25 dB (+/−5% FSH) the curve should generally be recalculated.

The Water DAC curve in all other acquisition computers may be updated with the most recent curve. Note that while the Water DAC curve is unique to each transducer, any DAC curve demonstrated to provide the appropriate responses for other transducers may be applied.

(2) Transducer Gain Trim

Elements within a transducer can vary in sensitivity +/−4 dB or more from each other. Variation in instrumentation, cables and connectors can also compound the element to element sensitivity variation. The consistency of the TFM result may be improved when these variations are corrected.

The following test may be performed at a static position rather than as part of the calibration scan. The acquisition operator may use the calibration feature in the NEOVISION™ application to adjust and confirm the overall gain and the gain of the individual channels. The calibration feature is found under the UT Calibration tab in Set-up mode.

(a) The Acquisition Operator then prepares the gain trim calibration by setting the calibration gate to encompass the interface signal. The Acquisition Operator ensures there are no bubbles on either the transducer face or on the reference tube as these will invalidate the gain trim adjustment.

(b) The Acquisition Operator starts the calibration. NEOVISION™ will automatically adjust the gain and then after a short period (approximately 5-10 seconds) return a message indicating the range of gain needed to adjust the individual elements. In some cases the gain trim utility will report error(s) if elements are outside the nominal gain trim range. This may be the case for missing/dead elements and/or conditions where air bubbles exist either on the transducer/mirror or reference tube surface. The Acquisition Operator may investigate the error messages to correct any conditions beyond the expected result.

(c) The Acquisition Operator may evaluate the reported range to compare it to previous gain trim adjustment.

(d) The Acquisition Operator should generally note any differences in individual element response from the previous adjustment. The gain trim adjustment may in some embodiments be within 2.0 dB of the previous evaluation for the same transducer. Differences may arise from the presence of very small air bubbles or transducer aging. The differences may be resolved before proceeding. If the gain trim is within acceptable limits the Acquisition Operator may update the Probe File and apply the gain trim settings for the current inspection. This value is recorded and is subsequently confirmed to be within an acceptable range once the transducer is mounted in the manipulator and measured on the reference block.

(3) Metal DAC Curve

The metal DAC is created by scanning over the metal path steps while using the Water DAC but no secondary DAC. The gain is adjusted from the baseline gain of the Water DAC such that the first backwall echo does not exceed 40% FSH. This the difference between the Water DAC baseline gain and the gain required to being the first backwall reflection to 40% is the gain offset for the Metal DAC. The file is then saved and analyzed.

The maintenance technician using the cursors on the A-scan generally records the time of arrival and peak amplitude of the first backwall signal. The steps are measured in series from thinnest to thickest. The amount of gain needed to raise the backwall signal to 40% FSH is calculated and entered along with the time of arrival of the peak in the DAC table.

A series of points is created and a best fit curve is plotted through the data series. Any significant outliers to the curve may be investigated for anomalies. The Metal DAC is then activated and a final scan of the reference tube is conducted to ensure the all interface signals are at 40% FSH regardless of metal thickness. In some embodiments, if there is any deviation beyond 1.25 dB (+/−5% FSH) the curve should generally be recalculated.

The metal DAC curve is saved. The Metal DAC curve in all other acquisition computers may be updated with the most recent curve. Note that while the Metal DAC curve is unique to each transducer, any DAC curve demonstrated to provide the appropriate responses for other transducers may be applied.

(4) Temperature Transducer Check

The temperature transducer is checked for functionality and is not part of the transducer characterization. This can be conducted by measuring the temperatures in an ice water bath as well as boiling water. Alternatively calometric devices may be used to test and calibrate the temperature transducers. Although the temperature transducer is calibrated for a limited range, repeatable demonstration of the range will indicate the transducer is operating normally.

After calibrations defined in the previous paragraphs are performed, the resulting updated transducer file may be transferred to the Acquisition computer. The new file may be used when the tool containing the probe (e.g. the manipulator 100) is applied.

System Calibration

System calibration is defined as verifying the value for operating variables and confirmation of the continued performance of the FMC data acquisition system as a whole. The process of converting the UT data into the final result is time-consuming, thus analysis is not part of the calibration procedure. Instead it is generally sufficient to demonstrate the relevant UT parameters have not deviated from the recommended values over the course of the inspection.

System calibration encompasses checking:
1. Encoder verification
2. Element Functionality Check
3. Transducer—manipulator Alignment/Probe Axis Function Check
4. Metal path measurement verification
5. Transducer delay check
6. Water path attenuation check
7. Temperature sensor verification
8. Water path measurement check Should the calibration values fall outside of the prescribed or previous applicable values, the calibration may have failed. The Analysis Operator may address possible causes but not vary parameters (e.g. eliminate air bubbles but not change velocity) and re-attempt the calibration scan. If the calibration results are acceptable the inspection can proceed. If the calibration has failed then all inspection files obtained following the most recent valid calibration are generally discarded. The feeder welds in question may be rescanned.

Calibration Equipment

Figure 57:
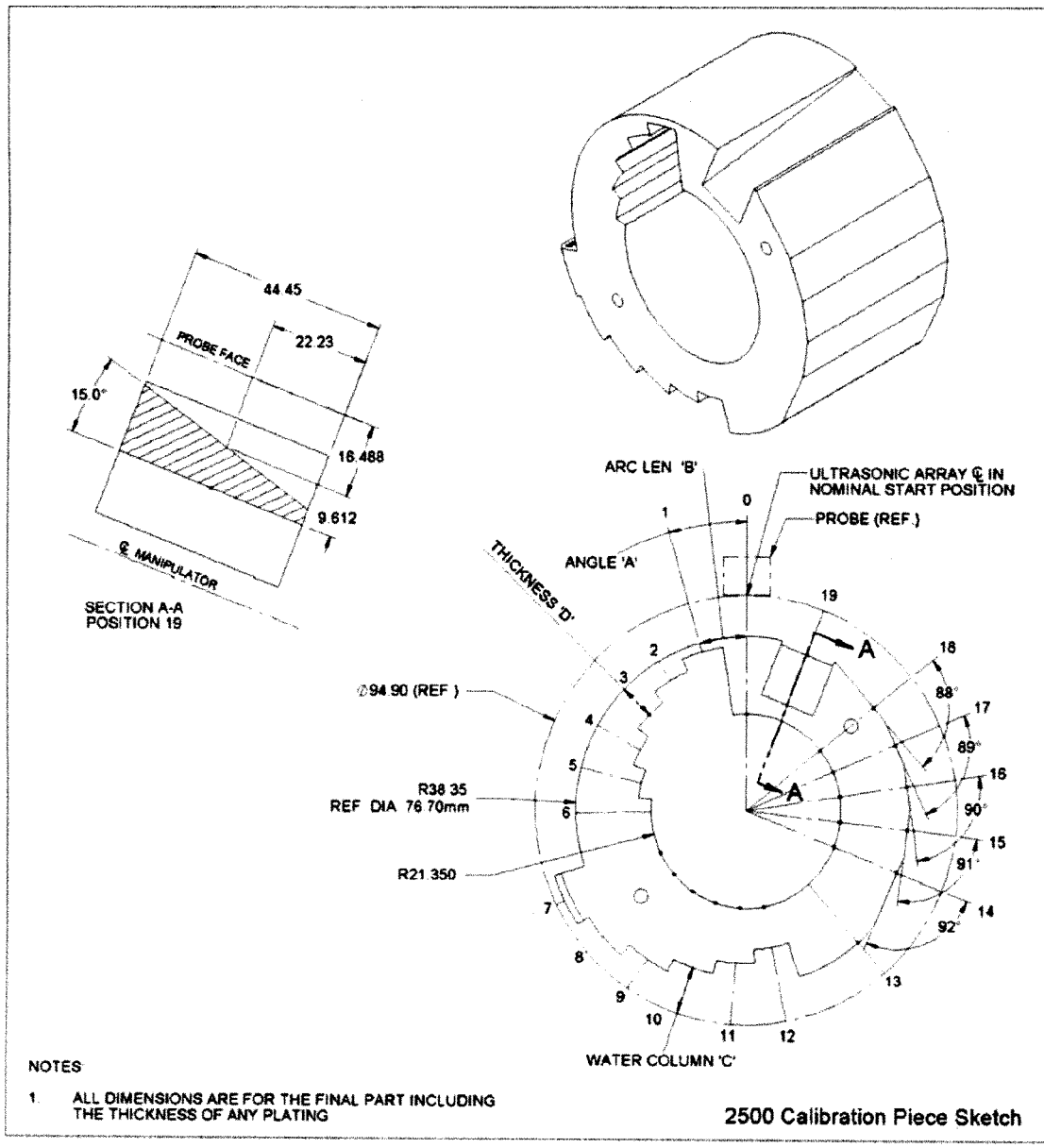
FIG. 57 is a 2.5" reference block specimen used for calibrating a 2.5" manipulator according to an example embodiment.
Figure 58:
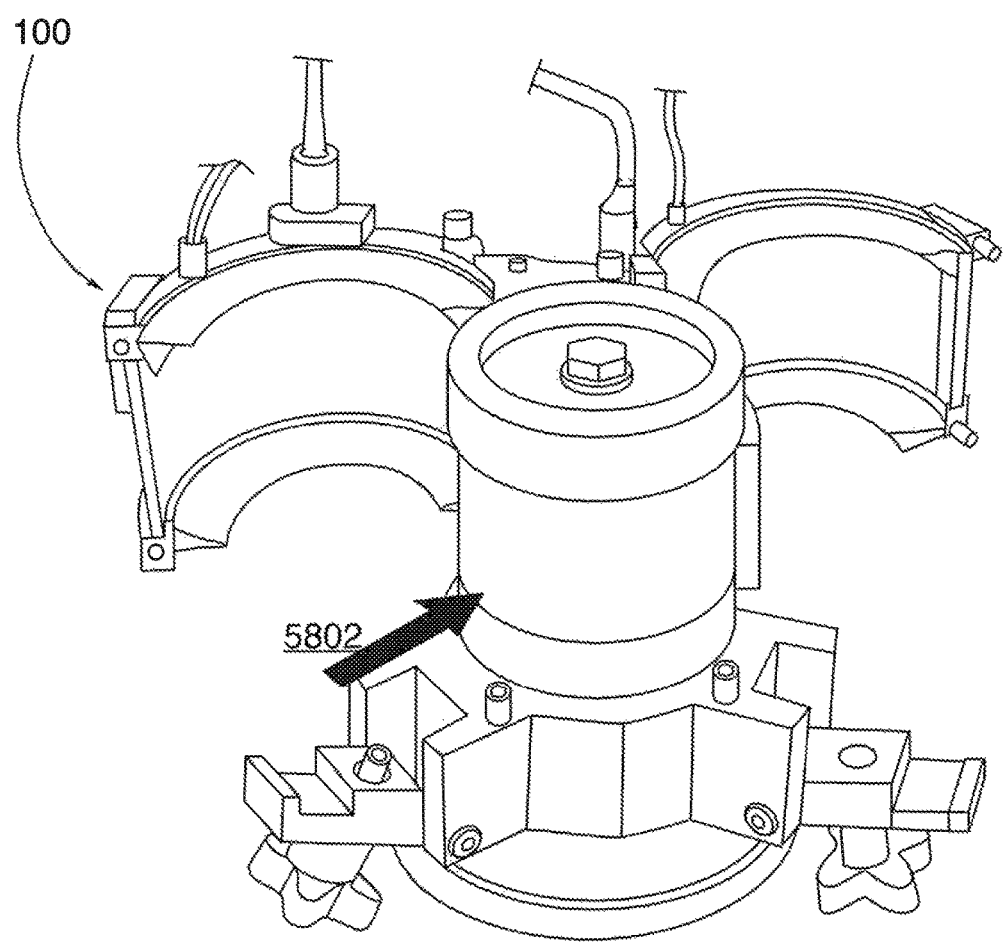
FIG. 58 is a perspective view of a calibration block setup showing an example manipulator in an open configuration prior to calibration.

The calibration equipment consists of the following items:
1. 2" reference block specimen (see FIG. 55)
2. 2" reference block specimen for 6 degree configuration (see FIG. 56)
3. 2.5" reference block specimen (see FIG. 57)
4. reference block stand
5. transducer/manipulator combination connected to UT instrument The calibration equipment is configured with the manipulator 100 installed on the reference block as depicted in FIG. 58, with the reference block specimen depending upon the manipulator size to be calibrated. The arrow 5802 in FIG. 58 indicates the approximate start point of the scan.

Calibration Method

The platform operator clasps the manipulator on the appropriate size reference tube ensuring the manipulator outer ring is engaged in the stand locator pins. In some embodiments there is a separate reference tube for the conventional and 6 degree manipulator configurations. Calibration of each manipulator configuration is conducted on the appropriate reference tube.

Figure 59:
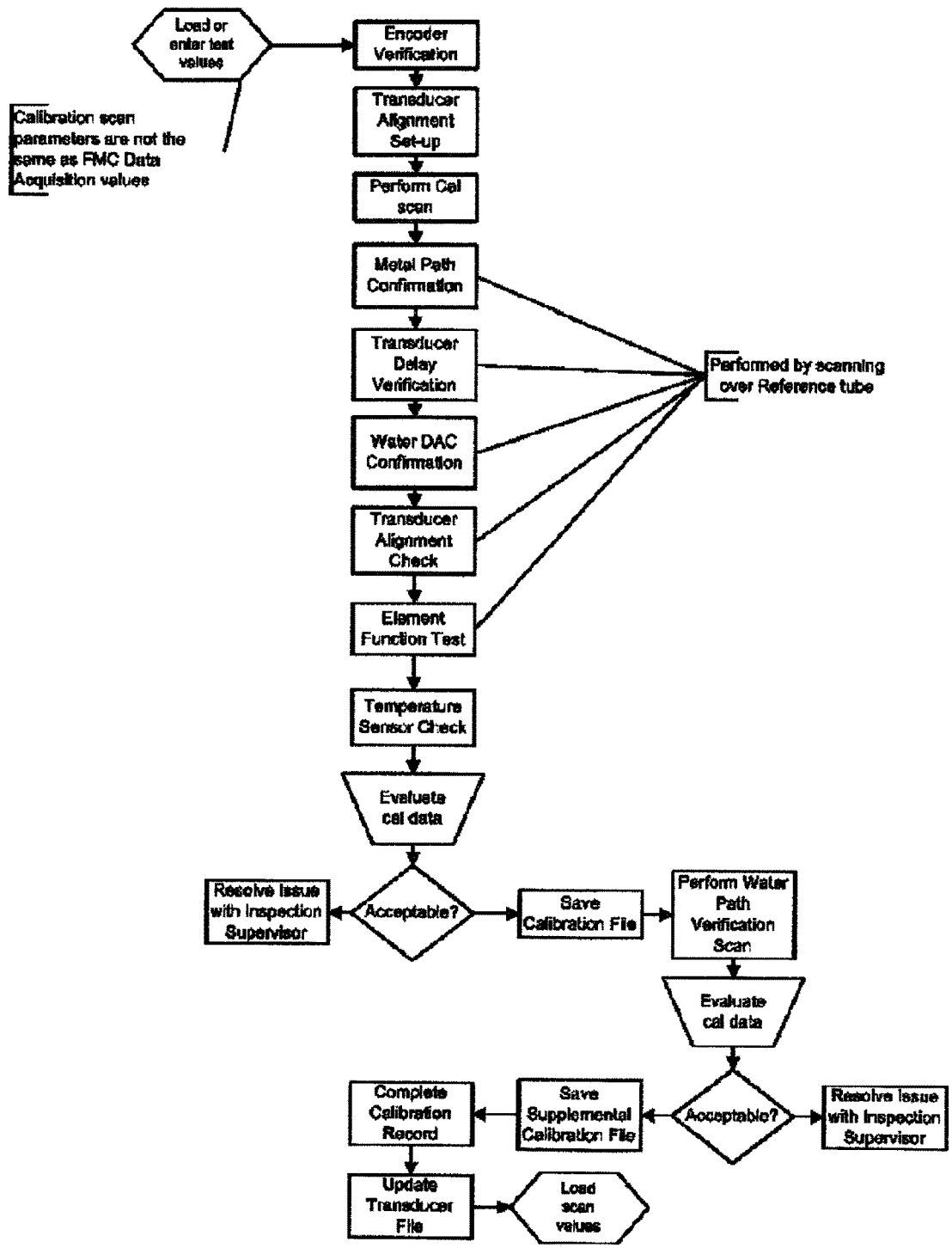
FIG. 59 is a flow chart showing the steps performed during calibration of an example manipulator using an example calibration block according to an example embodiment.

The stabilizing arms are then latched over the manipulator. The platform operator indicates to the acquisition operator when the system is ready for the calibration verification. A flow chart for the sequence of calibration steps is given in FIG. 59.

The acquisition operator starts the couplant pump and the scan under the set-up window of NEOVISION™. The acquisition operator observes signals in both A and B scan windows to confirm the manipulator is full of couplant. Should the manipulator not fill with couplant or be incapable of maintaining water column for the duration of the calibration exercise, the cause may be identified and fixed before continuing with the inspection.

1. Encoder Verification

Verification of the proper behaviour and values for the encoder is easiest to perform by driving the manipulator from the home position one full revolution to arrive back at the home position. These locations are easily observed by lining up the parting line inner ring halves with the parting line of the stationary ring halves. The value should generally match the circumference to within +/−0.3 mm. In example embodiments with a 2" manipulator and a 2.5" manipulator, the distance is: 195 mm for the 2" manipulator and 245 mm for the 2½" manipulator.

The following steps may be used by an operator:
(a) Approach the home position from the negative side by driving in the positive direction.
(b) When the split in the inner rings align with the split in the outer ring, set the position to 0.0 under the 'Motors/Relays'. If this position is overshot, the manipulator should not be driven in the negative direction, as doing so may build manipulator lash into the calibration. If the position is overshot, repeat the approach from the negative side.
(c) From this zero position, drive the manipulator in the forward direction, 195 mm for the 2" manipulator, and 245 mm for the 2.5" manipulator.
(d) The manipulator should generally perform a 360 degree rotation and stop so that the split in the inner rotating ring aligns with those of the outer rings. Any offset from this location may represent an error in the calibration or mechanical operation of the manipulator.
(e) The test is conducted in the opposite direction by returning the manipulator to the home position.

The final value in some embodiments should be 0 mm within +/−0.3 mm.

Failure to meet these requirements in either direction may be due to several possible causes: incorrect settings, electrical problems or mechanical problems. If the encoder is beyond these values in either direction the manipulator may be removed from service for further evaluation.

Measurement of encoder accuracy can be affected by backlash in the manipulator drive train. The backlash varies from manipulator to manipulator and can increase in time due to wear in the gear train and manipulator bearing surfaces.

2. Element Functionality Check

The NEOVISION™ application has a feature which introduces a series of linearly varying delays into each channel that when viewed appear like a saw tooth pattern. This test can be conducted in a static position while in set-up mode on the reference sample. Alternatively this test may also be conducted as part of the calibration record by noting the presence/absence of the element responses over a calibration feature on the reference sample.

A quick check of the main diagonal B scan response will highlight any missing elements. The operator may use the cursors to identify the channel number of the missing element(s). The channel numbers of any missing element(s) may be recorded in the maintenance record.

If the transducer and instrument combination fail to meet the requirement identified in the "Element Functionality" factor set out in Table 3 below, the transducer and/or instrument may be removed from service for repair.

The Acquisition Operator then loads the UT and scan settings for the Verification scan. See Tables 1 and 2 below. The Platform Operator may ensure proper cable routing for the calibration scan. When ready, the Acquisition Operator starts the calibration scan.

TABLE 1

Example UT Parameters for 0 degree calibration

| Parameter | Value | Comments |
| --- | --- | --- |
| Averaging | 1 | |
| Active aperture | 128 | |
| Pulser mode | Echo Trigger | |
| Digitizing Frequency | 100 MHz | Used for measurement accuracy |
| Zero Offset | Specific to probe - nominally 32 DP | |
| Range | 1250 | |
| Gate Start | 245 DP | |

TABLE 1-continued

Example UT Parameters for 0 degree calibration

| Parameter | Value | Comments |
| --- | --- | --- |
| Gate Length | 2500 DP | For acquiring 17 mm water column and angle |
| Gain | ~32-35 dB | Function of probe and system |
| Threshold | ~13% FSH | Adjusted as required to preclude triggering on Initial Pulse |

TABLE 2

Example UT Parameters for 6 degree calibration

| Parameter | Value | Comments |
| --- | --- | --- |
| Averaging | 1 | |
| Active aperture | 128 | |
| Pulser mode | Echo Trigger | |
| Digitizing Frequency | 100 MHz | Used for measurement accuracy |
| Zero Offset | Specific to probe - nominally 32 DP | |
| Range | 1500 | |
| Gate Start | 350 DP | |
| Gate Length | 3000 DP | For acquiring 17 mm water column and angle |
| Gain | ~32-35 dB | Function of probe and system |
| Threshold | ~13% FSH | Adjusted as required to preclude triggering on Initial Pulse |

The Acquisition Operator may evaluate the calibration scan once complete as per the items listed in the table below.

3. Transducer—Manipulator Alignment Check

Figure 55:
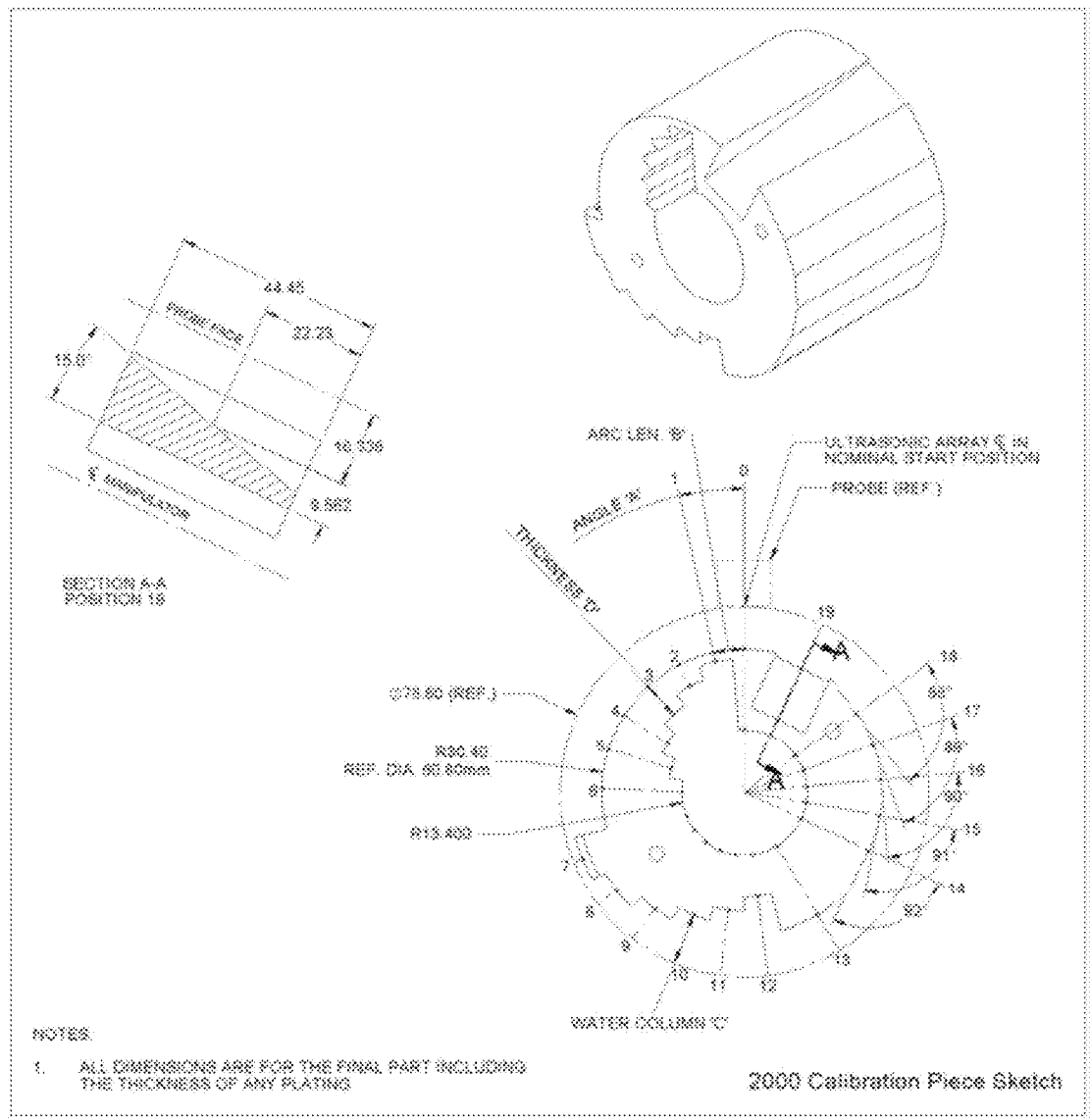
FIG. 55 is a 2" reference block specimen used for calibrating a 2" manipulator according to an example embodiment.
Figure 56:
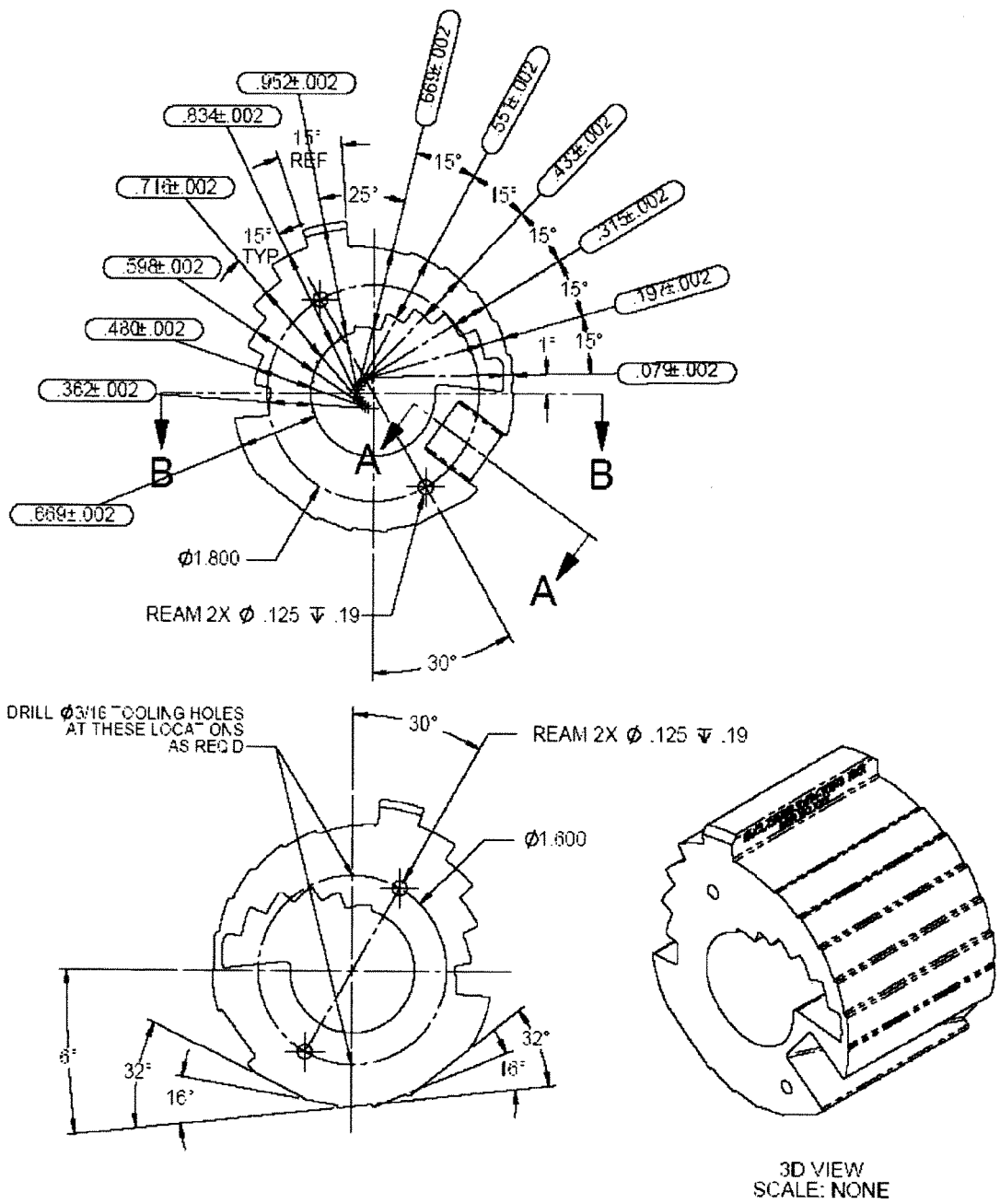
FIG. 56 is a 2" reference block specimen used for calibrating a 2" manipulator in a 6 degree configuration according to an example embodiment.

Transducer—manipulator alignment may be evaluated by scanning across the 5 flat regions of the reference block (such as the example blocks shown in FIGS. 55-57). These regions are inclined in some embodiments with respect to the reference block axis. When correctly set, the signal amplitude will rise from the 2 degree surface to the 1 degree surface, peak on the surface parallel to the transducer face and then fall to the 1 degree and again to the 2 degree surfaces.

The Acquisition Operator may drive the manipulator from the home position forward around the block by a distance of 145 mm for an example 2" manipulator and 185 mm for an example 2.5" manipulator. The Acquisition Operator may then set the motion increment to 0.1 mm and increment relative to the current position while observing the interface signal. The Operator may continue to increment the position until the signal is observed to peak and then fall. At this point the Operator may set the current position of the manipulator; to 149.1 for the 2" manipulator and to 189.6 mm for the 2.5" manipulator. Driving in the opposite direction may result in manipulator backlash being incorporated into the settings.

If the peak is found to occur on other surfaces, the transducer and manipulator may not be aligned and should be adjusted. The manipulator may be removed from service to address this issue.

Once the peak is identified and the manipulator circumferential position set as per manipulator size, the Acquisition Operator may drive the manipulator to a point beyond zero: −3 mm is suggested. This may be required to remove lash from the manipulator drive train. The Acquisition Operator may drive the manipulator back to the 0 position (not necessarily home position). The Acquisition Operator is then ready to perform the remaining steps of the calibration.

The Acquisition Operator should generally select the WPIT Verification scan, not the WPIT Calibration scan. The Verification scan confirms the function of the DAC curve whilst the Calibration scan builds the DAC curve.

The verification scan runs a series of positions around the Reference Block, the metal path series, followed by the water column series, followed by the angle verification and the angled surface.

This check may be varied or omitted in embodiments incorporating a reflector or mirror 154 that dynamically changes the scanning angle of the transducer. For example, in some embodiments having a mirror 154, transducer—manipulator alignment is evaluated by scanning across the continuously variable region of the reference block. This region is effectively a cam surface that passes through a range of angles. The control system will drive the mirror to an angle to optimize the interface signal. The angles reported should correspond to the angle of the surface at the various points that are checked.

To perform this function manually, the Acquisition Operator may drive the probe axis to peak the interface amplitude at various locations along the span of the continuous surface. The probe axis angle is reported and compared to the expected angle. The difference between the reported angle and the expected angle should not exceed +/−1 degree in some embodiments.

4. Metal Path Measurement Verification

The accuracy of the metal path measurement may be verified by checking various steps in the reference block. In some embodiments, a 2 mm, 8 mm, and 14 mm step are checked. Measurements specific to each example reference block shown in FIGS. 55-57 are found in Tables A12 to A15 at the end of the Description.

(a) This measurement is conducted on the A scan window of the matrix main diagonal channel selection corresponding to the linear electronic B scan. Any channel from the B scan may be selected for this measurement.

(b) For this measurement the time axis is set to half path and the velocity is set to carbon steel under the Display Options tab.

(c) The measurement is made by zooming in on the region of first two backwall echoes in the A scan such that the individual data samples can be distinguished.

(d) Using both pairs of cursors, the measurement is made by placing one cursor on the first rising zero cross of the first echo and the other cursor on the corresponding zero cross of the second echo. The measurement is the difference between metal path values of these two cursors. This value is directly obtained from the INFO button on the A scan window margin.

(e) The values for these steps are recorded in the calibration record.

If the value(s) fall outside the acceptable range, the cause of the discrepancy should be identified and remedied before the inspection continues. All data obtained prior to identification of the discrepancy may no longer be considered valid.

5. Transducer Delay Check

Due to the difficulty in precisely locating the manipulator on the reference sample the transducer delay can vary merely due to positional inaccuracy. Transducer delay is therefore generally performed only as an indication.

For this test, the interface signal and second interface multiple should be present in the scan data. This can be achieved on either of the 2 mm or 5 mm water column steps.

The transducer delay is evaluated by subtracting the measured water column distance from the design water column distance for that step. The delta will be the change in probe delay from that currently set. The most accurate measurement will be obtained from the first minimum of the respective signals as the subsequent distortion increases the error in the measurement. Note this distance is generally evaluated in digitization points instead of water velocity based half path.

The Acquisition Operator may use other steps or channels to confirm a reading that appears to be outside expected limits.

6. Water Path Attenuation Check

The water path attenuation curve may be verified by checking the amplitude of the interface signal.

The calibration software (WPIT verification) used in some embodiments has a feature that reports the range of amplitude height variation for a given element on the various water column steps. The amplitude of the interface signal should generally remain within 50 to 99% FSH for any main diagonal channel on all steps of the reference block. Deviation from this amount in the absence of other possible factors (air bubbles) suggests the water path attenuation curve is not accurate.

If the reported level is outside the range for an individual element, the Acquisition Operator may perform a manual assessment using another transducer element response. The Acquisition Operator may set the cursor level in the A scan window to 80% FSH. The Acquisition operator may select the desired channel and examine the amplitude response from the range of water column steps. If the responses fall within 50 to 99% FSH, the attenuation check is generally acceptable. If deviation is found to exist on several elements of the transducer, or if the range of deviation is found to be excessive, resolve the issue.

7. Temperature Sensor Verification

Given the robustness of these type of devices it is usually sufficient to verify the temperature reading is both stable and within expected bounds. Nominal bounds anticipated for inspection are generally 15 to 45 degrees Celsius.

The Acquisition Operator may save the calibration scan and record the results of the calibration in an FMC Feeder Calibration Record. In preparation for the supplementary scan the manipulator is driven to the home position if not already there.

Any anomalies may be resolved by appropriate steps (e.g. component replacement, eliminating air bubbles), and re-calibrated before proceeding with inspection.

8. Water Path Measurement Check

A supplementary scan may be required to perform a water path measurement check. The scan generally runs from 60 mm to 100 mm on the Reference block in steps of 0.5 mm. This scan may be conducted for both the 0 degree and 6 degree configurations, however only the 0 degree result may be evaluated at this time.

In some embodiments, water path measurement is confirmed by checking the measurement deltas between the 2, 5, 8, 11, 14 and 17 mm water column steps in the reference block. This measurement is conducted on the A scan window of the matrix main diagonal channel selection corresponding to the linear electronic B scan. Any channel from the B scan may be selected for this measurement. Measurements specific to each reference block may be kept on record and used as a reference in the calibration process.

For this measurement the time axis may be set to half path and the velocity may be set to water under the Display Options tab.

The measurement is made by zooming in on the region of interface echoes in the A scan such that the individual data samples can be distinguished. Using both pairs of cursors, the measurement is made by placing one cursor on the first rising zero cross of the interface echo and then indexing to the image of the next step, placing the other cursor on the corresponding zero cross of the interface echo. The measurement is the difference between water path values of these two cursors.

This value is directly obtained from the INFO button on the A scan window margin. Subsequent water column step measurements are then made in the same manner.

Parameters & Values for Calibration

Table 3 below identifies the parameter to be measured and applicable target value to be obtained.

TABLE 3

List of example calibration criteria and values

| Factor | Value | Range | Comments |
|---|---|---|---|
| Element Functionality | Not applicable | No more than 13 missing, no more than 3 adjacent missing | Reject transducer if greater than 13 or 3 adjacent elements |
| Probe delay | 32 DP | 2 DP | Note - when at 100 MHz sampling rate |
| Water column DAC | 80% FSH | 99%-50% FSH | |
| Metal path measurement | Block specific, Refer to Tables A12 to A15 | +/−0.03 mm | |
| Transducer - manipulator alignment | 0 | +/−1 | |
| Temperature sensor function | Not applicable | 15-45° C. | Observed to be functioning and rational |
| Encoder check | 0 to 195 (2") or 245 (2.5") | +/−0.3 mm | Check for backlash or excess play - replace manipulator if necessary |
| Water column measurement | Block specific, Refer to Tables A12 to A15 | +/−0.01 mm | Measure the difference between the steps of the Reference Block |

Calibration Record Contents

The FMC Feeder Calibration Record may generally contain the following information:

Date and Time of calibration file
Name of the calibration file
Transducer serial number, manipulator serial number
Micropulse serial number, Vault Interface Module serial number
Reference tube serial number
Name of Acquisition operator performing calibration
Name of Platform Operator performing calibration
Data table recording the results of the calibration Intervals A calibration scan of the reference block may be conducted at the following intervals:

start of a shift
4 hour intervals
change of acquisition operator

In addition to the above, calibration scans may be performed whenever a transducer, manipulator or instrument is changed. The calibration check is a confirmation that the inspection system remains in calibration and is fully operational. The calibration check file may be recorded with the inspection data.

Ultrasonic Equipment Settings

The ultrasonic equipment settings may be available in a pre-defined configuration (set-up file). The Inspection Supervisor responsible for the initial set-up of the equipment for the inspection campaign may ensure the most recent version of all set-up files are loaded into the NEOVISION™ software.

Nominal values for the settings are given Table 4, below.

TABLE 4

Nominal values for Ultrasonic testing

| Parameter | Essential | Value | Comments |
|---|---|---|---|
| Probe Element Spacing | Yes | 0.195 mm | Fixed per probe specification |
| Probe Element Pitch | Yes | 0.27 mm | Fixed per probe specification |
| Probe Element Elevation | Yes | 5.0 mm | Fixed per probe specification |
| Probe Element Count | Yes | 128 elements - no greater than 13 elements non responsive with and no greater than 3 elements adjacent | Fixed per probe specification |
| Probe Centre Frequency | Yes | As measured, within +/−10% of nominal | Fixed per probe specification |
| Transducer element gain trim | Yes | Elements should be within +/−2.0 dB of previous | As determined via procedure |
| Zero Offset | Yes | Should be within +/−2DP of known delay, however current designs are ~32 DP @ 100 MHz or 16 DP @ 50 MHz | As measured via probe characteristics |

TABLE 4-continued

Nominal values for Ultrasonic testing

| Parameter | Essential | Value | Comments |
|---|---|---|---|
| Pulse width | Yes | 40 to 60 ns | Optimized to transducer |
| Pulse Voltage | Yes | 70 V | Exceeding 100 V will accelerate transducer aging |
| Delay | Yes | ~30 DP but not less than 20 DP | Variable - Feeder and weld cap geometry influence the range of this variable |
| Range | Yes | ~500 to 850 DP | Function of thickness & water column range |
| Digitization Rate | Yes | 50 MHz | Optimized for data transmission rates |
| Digitization Resolution | Yes | 12 Bit | |
| Averaging | Yes | 1 | |
| Data Collection Mode | Yes | FMC | |
| Active Aperture | Yes | 128 | |
| Gain | Yes | Variable - nominal values in a range of 40 to 47 dB | See procedure for details |
| Filter | Yes | None | Using the filter influences subsequent processing |
| Water DAC | Yes | On - as determined by procedure | |
| Metal DAC | No | Off | As per Neovision ™ 1.0 analysis software |
| Interface Gate | Yes | On | |
| Set interface to Zero | Yes | Off (unchecked) | |
| Interface Gate Start | Yes | ~225-350 DP but not less than 200 DP | Function of scan type, i.e., 0 degree, 6 degree in case of 2" |
| Interface Gate Range | Yes | ~1000 DP | Function of feeder geometry |
| Interface Gate Amplitude | Yes | ~11% FSH | |
| Prem-trigger acquisition | Yes | On - 30 DP | |
| Gate 1 | No | Off | Input for data quality indicator |
| Gate 1 Start | No | | Input for data quality indicator |
| Gate 1 length | No | | Input for data quality indicator |
| Gate 1 Amplitude | No | 5% FSH | Input for data quality indicator |
| Outer Diameter Aperture | No | 18 | Input for data quality indicator |
| Minimum Percentage | No | 50% | Input for data quality indicator |
| Preferred Percentage | No | 80% | Input for data quality indicator |
| Inner Diameter Aperture | No | 32 | Input for data quality indicator |
| Minimum Percentage | No | 50% | input for data quality indicator |
| Preferred Percentage | No | 80% | Input for data quality indicator |

Ultrasonic Test Set-Up

Table 4 above identifies the nominal Ultrasonic parameters generally used in this inspection. The Acquisition Operator may confirm the appropriate parameters have been loaded following the calibration run.

Figure 79:
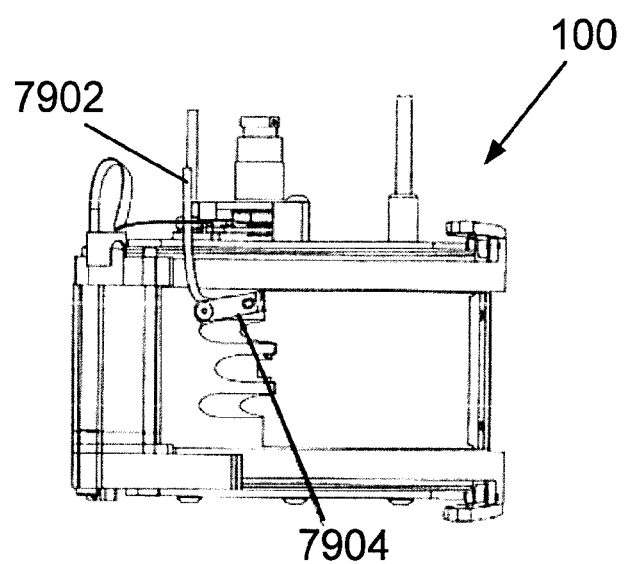
FIG. 79 is a side view of an example probe manipulator having a temperature sensor.
Figure 80:
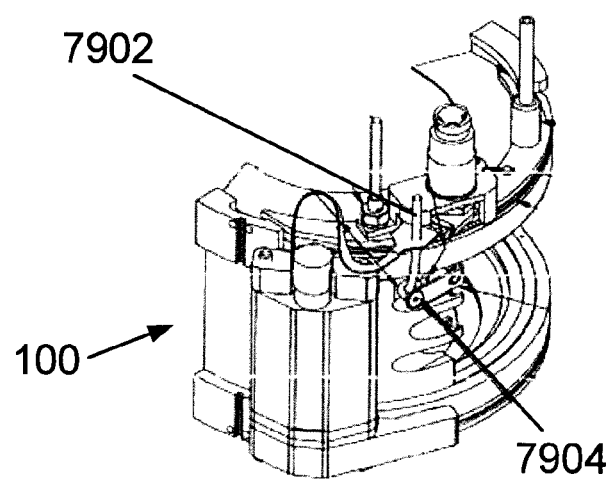
FIG. 80 is an isometric partial view of the example probe manipulator of FIG. 79.

The temperature of the colt/plant during acquisition can change by an appreciable margin, with a typical range of 18 to 40 degrees and, in some instances, beyond this range. There is a corresponding change in sound velocity within the couplant. Unlike other inspection methods, velocity change in the couplant can have a significant effect on the results. Therefore the temperature at which the inspection is conducted should generally be monitored. Acceptable temperature range for inspection in some embodiments is 15 to 45 C. If temperatures are encountered outside of this range, efforts to bring the temperature within the specified range may be made, A temperature sensor may be included in the hardware in some embodiments. FIGS. 79 and 80 show an example temperature sensor 7902 connected to the manipulator 100 by means of a temperature sensor attachment clip 7904. The Neovision™ application may record the temperature for each acquisition position.

Data Validation Indicator

Some embodiments may include a Data Validity Indicator software feature as an aid to the Acquisition Operator in evaluating the data set. The Indicator displays the presence of signals in the interface gate and gate 1 for the OD and ID surfaces respectively.

Input parameters are:
Interface gate
Interface gate amplitude
Gate 1

Gate 1 amplitude

OD aperture size, minimum percentage, preferred percentage

ID aperture size, minimum percentage, preferred percentage

Input parameters may be adjusted in set-up mode.

Inspection Sequence Definition

A separate inspection sequence may be defined for the 2" and 2.5" manipulators. The settings for the manipulators are given in Tables 5 and 6 below.

TABLE 5

Inspection sequence parameters - 2.5" manipulator

| Parameter | Value | Comments |
|---|---|---|
| Start | 0 | Start position may differ from home position |
| End | 245 | Based on pipe diameter |
| Scan Interval | 0.5 | Procedure requirement |
| Speed | 10 | |
| Counts/mm | 91.80 | Calculated value |
| Manipulator radius | 47.45 | Design value |
| Reduction ratio | 3748.6 | Calculated value |
| Maximum current | 500 | Related to maximum surge current - do not exceed |
| Stall current | 450 | Related to maximum continuous current |
| Proportional Gain | 2000 | Determined via testing |
| Integral Gain | 80 | Determined via testing |
| Derivative Gain | 1000 | Determined via testing |

TABLE 6

Inspection sequence parameters - 2" manipulator

| Parameter | Value | Comments |
|---|---|---|
| Start | 0 | Start position may differ from home position |
| End | 195 | Based on pipe diameter |
| Scan Interval | 0.5 | Procedure requirement |
| Speed | 10 | |
| Counts/mm | 65.64 | Calculated value |
| Manipulator radius | 39.3 | Design value |
| Reduction ratio | 2133.3 | Calculated value |
| Maximum current | 500 | Related to maximum surge current - do not exceed |
| Stall current | 450 | Related to maximum continuous current |
| Proportional Gain | 2000 | Determined via testing |
| Integral Gain | 80 | Determined via testing |
| Derivative Gain | 1000 | Determined via testing |

Scans and Inspection Zones

Due to offset between the feeder and the manipulator as well as surface variation of the feeder, the manipulator in some example embodiments can only acquire UT signals in specific orientations. A compromise may be effected wherein the manipulator is configured in a 0 degree mode to acquire intrados and extrados areas, a 6 degree forward configuration to acquire the left cheek and a 6 degree reverse to acquire the right cheek. The UT signals may be degraded when the manipulator is scanning over areas other than the intended region.

The start location for the 0 degree scan is in some embodiments defined as the location where the transducer is directly over the right cheek. The manipulator is oriented with the cables facing toward the header (away from the Grayloc™) and the scan proceeds in the positive direction through the intrados of the bend to the left cheek, then to the extrados of the bend terminating on the right cheek.

The start location for the 6 degree forward scan is in some embodiments defined as the location where the transducer is slightly to the right of the fitting intrados. The orientation of the cables is the same as the 0 degree configuration, facing toward the header, away from the Grayloc™. The scan proceeds from the intrados over the left cheek to just past the extrados centre line. The scan should generally acquire both intrados and extrados and not be less than 100 mm in length.

The start location for the 6 degree reverse scan is in some embodiments defined as the location where the transducer is slightly to the left of the fitting intrados. The orientation of the cables is opposite the 0 degree configuration, facing away from the header, towards the Grayloc™. The scan proceeds from the intrados over the right cheek to just past the extrados centre line. The scan must acquire both intrados and extrados and not be less than 100 mm in length.

The Acquisition Operator may identify the scan type, start and length in the Inspection Record.

In some embodiments having an adjustable reflector or mirror 154, the dual axis configuration may improve the capabilities of the system. By articulating the UT beam via a mirror 154, the tool may be capable of gathering the required data in one scan for most configurations. In the case of compound joints 2 scans may be required, one that tracks on the first fitting, and a second scan that track on the 2nd fitting.

Manipulator Set-up on Inspection Sample

The following steps may be carried out generally in all scan types:

(1) The platform operator may install the manipulator on the feeder, ensuring that the manipulator halves meet and are securely fastened. If direct access to the inspection area is not possible the Platform Operator can install the manipulator at an accessible area of the feeder and reposition the manipulator over the area to be inspected. The drive enclosure on the manipulator should generally be at the top of the feeder for horizontal feeder runs, or with the gear train at the bottom in case of vertical runs. The platform operator may also check the seals on the manipulator to ensure the direction they are flexed in is uniform.

(2) The platform operator may loop the cable over an adjacent end fitting to relieve strain on the manipulator, ensuring that there is sufficient transducer cable slack available to permit rotation of the manipulator in the intended direction.

(3) The platform operator and the acquisition operator may re-confirm the identity of the feeder to be inspected after the manipulator has been installed on the feeder.

(4) Once manipulator placement is confirmed, the acquisition operator may start the couplant pump to fill the manipulator. The platform operator may check the manipulator seals for excessive leakage. Adjustment of the seals may be required to reduce leakage. The platform operator may be required to adjust the flow rate to optimize couplant consumption via the valve on the couplant flow solenoid assembly.

(5) Coincident with checking the seals, the Platform Operator may also check and confirm that both halves of the manipulator are securely latched. Excessive leakage and poor motion control may be encountered if the halves are not fully engaged.

Inspection Process

Figure 60:
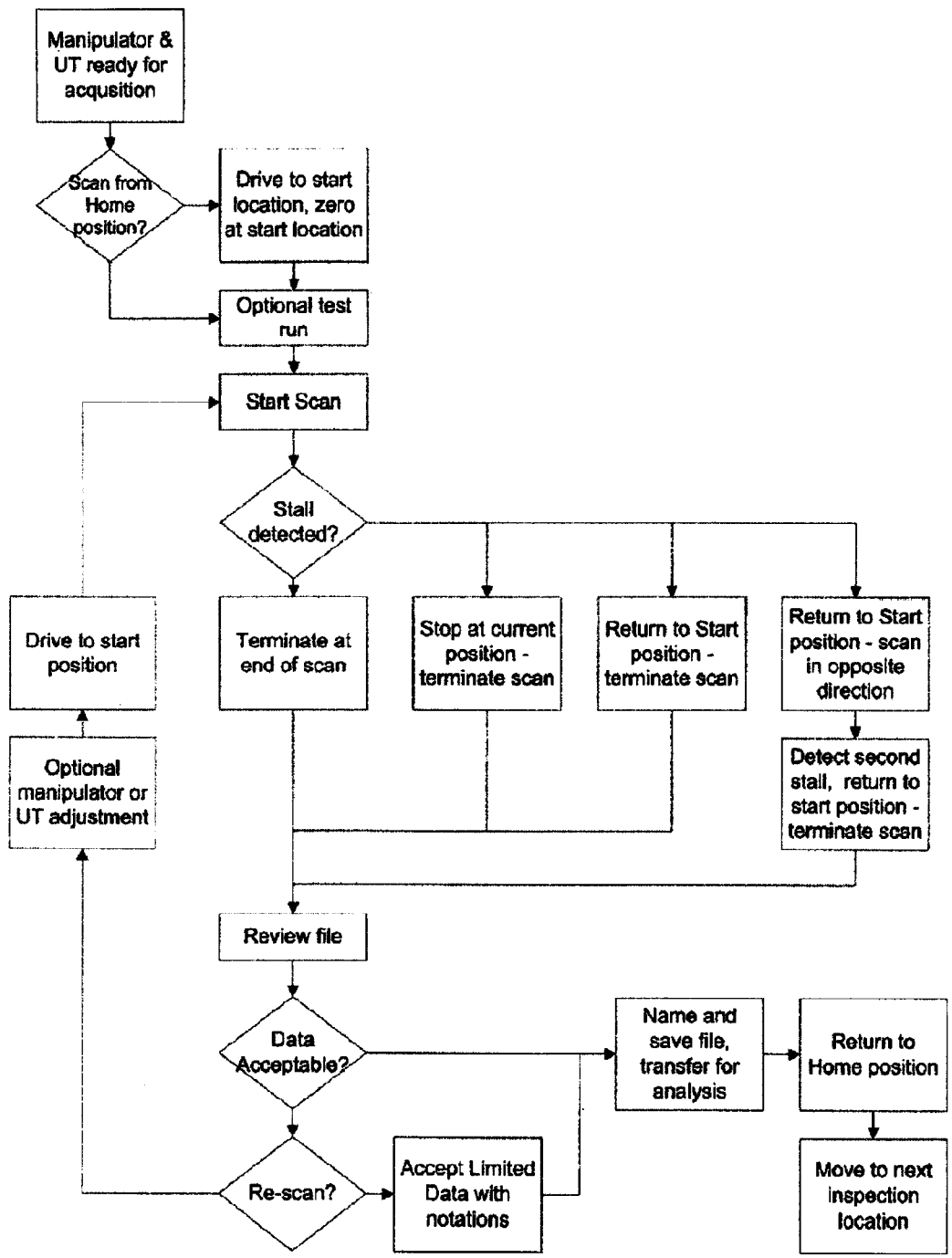
FIG. 60 is a flow chart showing the steps performed during inspection of a pipe diameter according to an example embodiment.

A flowchart for the inspection process is given in FIG. 60. The Acquisition Operator has the option of using different manipulator scanning modes depending upon the circumstance encountered. The following steps may be carried out generally in all scan types:

(1) The Acquisition Operator may start the static scan once the couplant pump has been started and couplant is confirmed to be leaking from the manipulator. The B scan window should be populated with linear B scan image, the A scan window should be populated with an A scan from the B scan window. If the B scan is present without the A scan, the Acquisition Operator may re-establish the link of the A scan selection to the B scan window. If neither window is populated, the Acquisition Operator and Inspection Supervisor may investigate and remedy the cause before proceeding. Once the A and B scans have been established the Acquisition Operator should make a cursory assessment of the scan quality to identify and correct any obvious deficiencies.

(2) The Acquisition Operator may jog the transducer to the desired start location, if not using the Home position as the start position. In the alternative the Platform Operator can perform this task using the local control on the VIM. When the transducer has been positioned at the scan start position the Acquisition Operator may set Start position to zero. Again, the Platform Operator may ensure sufficient cable slack and proper cable feed for the intended direction of travel.

(3) If at any time the Platform Operator sees the possibility of interference or restricted access for the inspection, the Platform Operator may notify the Acquisition Operator. The Acquisition Operator may choose to start the scan at a more advantageous position if clearance is an issue.

(4) The Acquisition Operator may choose to perform an optional test run. The purpose of the test run is to check the position of weld, signal amplitude over weld cap, manipulator alignment, presence of air bubbles or pockets, or other conditions/artefacts. The suggested value for circumferential resolution is 10 to 15 mm in some embodiments. Any adverse conditions noted in the test run can be corrected before the scan is conducted.

(5) The Acquisition Operator may initiate the scan from the start position. The platform operator may monitor the progress of the manipulator, paying close attention to proper cable feed. The acquisition operator may monitor the main diagonal B scan and corresponding A scans for data quality. In regions of reduced clearance the transducer may contact adjacent obstructions. It is usually preferable for the manipulator to stall out rather than the transducer pushing the manipulator aside. In the latter case, erroneous data may be recorded.

(6) The manipulator control may return the manipulator to the start position upon completion of the scan provided a stall condition has not been detected. If a stall condition has been detected, the behaviour of the manipulator may be as per the scan option chosen by the Acquisition Operator.

(7) The Acquisition Operator may review the completed file for factors affecting scan acceptability. The Acquisition Operator may shut off the couplant pump while reviewing the file. If the scan is not acceptable the Acquisition and Platform Operators may attempt to correct the deficiency and rescan the weld. There are no specified limits to the number of attempts at acquiring acceptable data. The Acquisition Operator may save data that does not meet a set of quality criteria if a number of scan attempts have been made. Notations describing the limitations may be made in the inspection record.

(8) If the Acquisition Operator deems the file to be acceptable, the Acquisition Operator may save the file and the Inspection Record.

(9) The Acquisition Operator may drive the manipulator to home position if it not there already.

(10) The Acquisition Operator may direct the Platform Operator to either detach the manipulator or move it to the next location if on the same feeder.

(11) The Acquisition and Platform Operators may perform the calibration at specified intervals as noted above. Data obtained subsequent to the most recent valid calibration scan may be discarded and the affected welds may be re-inspected.

Extent of Inspection

The extent of the inspection may be as per scope defined above and in FIGS. 49-50. Note the inspection zone defined for these geometries is based on a known position of the weld centreline. The manipulator may in some embodiments be built to track a cylindrical profile and may not necessarily track the weld centreline on complex geometries. On these geometries, the weld centreline may follow a sinusoidal trajectory in the scan data. Users may elect to reposition the manipulator for a second pass if it is deemed necessary to obtain data from other areas of the feeder.

Recording Criteria

With respect to the NEOVISION™ application, all signals following the interface signal may be recorded.

Evaluation and Acceptance Criteria

The Acquisition Operator may review the data file with respect to the following criteria to determine scan acceptability. Given the number of factors contributing to signal quality, the Acquisition Operator may monitor the data as it is acquired and spend time after acquisition performing any detailed review of selected areas.

The following criteria apply to the area of interest for the scan in question, i.e., extrados/intrados in the case of the 0 degree configuration, left cheek for the 6 degree forward scan, right cheek for the 6 degree reverse scan according to the example embodiments described above. Adverse conditions encountered in areas not relevant to the scan are generally not considered in data quality evaluation.

Signal Quality (1) Skew & Offset: Skew conditions may occur when the transducer is not aligned with the inspection surface in the axial direction. Offset is a similar condition, but may instead occur when the transducer, while parallel to the pipe axis, is a lateral distance sideways from the pipe axis. Both of these conditions may lead to a significant drop in OD signal amplitude as well as splitting of the OD signal. Under these conditions the ID signal may be completely lost. These conditions may be, to a degree, inherent when inspecting tight elbows or joint to joint configurations, but should not generally exceed 40% of the total circumference. Repositioning the manipulator in the axial and/or radial position with respect to the pipe surface may reduce the amount of distortion in the scan.

(2) Air bubbles: Air bubbles can occur in 3 places: on the inspection surface, on the transducer surface or oscillating in the water column. Air bubbles in general have a negative effect on data quality. Of the three conditions, air bubbles on the pipe surface have the least effect due to their localized nature and their tendency to be small in size. The larger of these bubbles may yield a response that causes acquisition to occur prematurely. Surface air bubbles are excessive when they result in an observable decrease in OD or ID signal amplitude. Air bubbles on the pipe may be reduced by a combination proper cleaning of the pipe surface and use of a surfactant during the cleaning process. Alternately, moving the manipulator axially along the pipe such that the seals scrub the surface can dislodge the majority of the bubbles.

Air bubbles located on the transducer/mirror face are more significant insofar as they constantly dampen the pulse from specific elements for the entire duration of the inspection. This type of air bubble is detected by an abnormal persistent drop in OD/ID signals particular to a few elements. This behaviour can be confirmed on the reference block. This type of air bubble may be unacceptable in some embodiments when it causes a drop of 2 dB or more in the OD/ID signals for the length of the scan. Air bubbles on the transducer/mirror face may be mitigated by gently swabbing the surface of the transducer with an approved UT gel couplant.

Air bubbles in the water column are evident as erratic triggering of the data acquisition interface. The most common cause of this type of air bubble is air entrained in the couplant supply. Inappropriate triggering of the data acquisition may lead to problems in the data analysis routines and could, under some conditions, give rise to erroneous results. Given the size of the water column, air bubbles in the water column should not generally occupy more than a few individual scan lines of the entire data file in some embodiments. If air bubbles in the water column are found in any appreciable quantity (more than 5% of scan locations in some embodiments), the source of the air bubbles should be identified and eliminated. Rescanning the affected weld may be conducted and noted in the inspection record.

(3) Air pockets: Air pockets may occur at the upper extremity of the manipulator and may be caused when the leak rate exceeds the couplant supply rate. An air pocket is observed when there is a partial to complete loss of UT signal across the transducer on consecutive scan lines. If the loss of signal is isolated to few channels or is short in duration (~5 frames) the acquisition operator may accept the scan file. Otherwise it may be advisable to address the cause of the excessive leak rate and/or increase the flow to the manipulator and rescan the feeder weld.

(4) Signal range limits: Factors such as position of the manipulator on the feeder surface, weld cap height and feeder geometry may have a significant influence on the range of water path distance in the scan. Excessive variation in the water path length may have an adverse effect on the scan quality. The most problematic situation may occur when the transducer is too close to the inspection surface (less than 200 DP in some embodiments). In this case the interface signal may merge into the run down from the initial pulse of the transmitting element, potentially leading to a false trigger. Furthermore the interface signal at this point may be adjacent the near zone for the element, in which case the signal amplitude is highly variable. Both of these conditions may introduce errors in the analysis process. The most significant effect, however, may be that the second water column interface will be captured in the data. This feature may be erroneously identified as the backwall since the amplitude may be greater than the true ID signals. In extreme cases such as excessive weld bead height, there may be insufficient clearance between the transducers and the inspection surface resulting in damage to the transducer itself.

A potentially less problematic condition is where there is excessive distance between the transducer and the inspection surface. This may occur on the opposite side of the feeder from the condition found in the above paragraph. The effect on data analysis is more subtle as the further away the transducer is from the inspection surface, the more restricted the viewing angle to any given feature.

One way to correct for range limit related problems is to reposition the manipulator with the intent of bring the manipulator close to the pipe on the long water column side while moving the manipulator away from the pipe on the short column side. The weld may be rescanned after re-positioning the manipulator. Note that problems introduced by excessive weld cap height might not be addressed by re-positioning the manipulator.

(5) Electrical Noise: Electrical noise in the scan may be identified as random (in few cases, repeating) signals in the one or more A scan traces. Under the assumption the noise is not correlated, i.e. does not form a repeating signal, the noise may be effectively averaged out in the data analysis. Problems may occur if the amplitude of the noise becomes high relative to the amplitude of the ID signals (within −6 dB of ID in some embodiments). The source of the electrical noise could be from a number of areas related to transducer, cable or connector damage or in some instances may be related to the Micropulse™ unit itself.

If electrical noise is identified in scan data, one means to address the problem is to replace the transducer or the Micropulse™ instrument and rescan the weld.

(6) Temperature Range: The temperature range for the data may be 15 to 45 C in some embodiments. Temperature outside this range may cause inaccurate results. Acquisition Operators may rescan such that the temperatures are within these bounds.

(7) Missing/dead elements: Missing or dead elements can arise from the natural aging of the transducer, damage to the cable or connector, or a fault in the Micropulse™ instrument. The scan is generally acceptable if no greater than 13 dead/missing elements are identified, provided that of the 13 elements, no more than 3 are immediately adjacent each other. If the fault can be traced to the Micropulse™ it is generally recommended that the Micropulse™ be removed for repair and the weld rescanned.

(8) Interface amplitude: The gain may be set to a level that under nominal conditions interface amplitude is saturated by 6 dB. The purpose of this setting is to ensure the weld cap interface signal remains at a sufficiently high level to trigger data acquisition. Excessive gain settings can be problematic for subsequent data analysis. If the weld cap signals are insufficient to trigger data acquisition, the gain may be raised, preferably not more than 6 dB in some embodiments, along with increasing the interface gate amplitude. Caution is advised when lowering gate amplitude since unwanted signals may now cause false acquisition.

(9) ID signal amplitude: Under nominal conditions, transducer normal to surface, stable water column, inspection surface at intermediate range, the pipe ID signals should attain an amplitude of approximately 10% FSH in some embodiments. If the pipe ID signals deviate by more than +/−6 dB from this value the cause may be investigated and corrected if possible (air bubbles, loose surface dirt).

(10) Inspection Coverage: Inadequate inspection area cover with respect to the desired coverage may require repositioning of the manipulator and rescanning. In some instances the inspection geometry may limit one-pass coverage necessitating two passes to achieve desired coverage. If this is the case two files may be used for the inspection with appropriate notations made in the inspection record. If obstructions limit the ability to position the manipulator to attain the required coverage, appropriate notations may be made in the inspection record.

(11) Start/End Correspondence: The beginning and final frame of a full circumference scan may display the same UT feature at the same location to within +/−2.0 mm in the axial direction and within +/−50 DP in the radial direction in some embodiments. If the start and end frames do not correspond to within these limits, the manipulator may have been displaced during scanning. If so, the scan may be repeated.

Data Files

The Acquisition Operator may export the data file to the analysis site. The analysis site may have multiple redundant storage devices to retain the data files. Analysis of the data may occur upon completion of the data acquisition phase.

Inspection Record Contents

The Inspection Record in some embodiments is a document that logs the parameters for the inspection conducted. There may be a separate inspection record for each feeder inspected. Note there may be multiple welds associated with any given feeder.

The following information may be contained in the inspection record: Station, Unit, Date, Time, Face, Feeder, Weld, File Name, Transducer, Manipulator, Micropulse Serial, Vault Interface, ID, Serial Number, Number, Module SN, Acquisition, Platform, Reference Tube ID, Calibration File, Operator, Resolution, Data Quality, Scan start, Scan length, Scan Type, Restrictions, a sketch of the actual feeder identifying the location and nature of any scanning restrictions, and any other relevant information about the inspection.

Data Analysis

The data acquisition method for inspection of feeder weld profiles in the present described examples is the application of the Full Matrix Capture (FMC) inspection technique. This method uses multiple independent elements to transmit and receive sound, and thus acquires a very large data array. The array is so large as to effectively preclude manual analysis of the data.

The basis for this analysis method is sequential back propagation of time indices in the source A scans. This technique is sometimes generically referred to as the Total Focus Method (TFM). The result of the analysis method is Computed Ultrasonic Tomography (CUT).

The following section defines the procedure by which FMC data may be analyzed using the NEOVISION™ software application in an example embodiment. It provides the procedures for using the NEOVISION™ software application as an analysis tool in the inspection of a feeder weld area. The data to be analysed is obtained from the inspection of feeder weld joints. This procedure is applicable to FMC data sets obtained from: pipe to pipe, pipe to fitting, fitting to fitting, and fitting to Grayloc™ welds. See FIG. 49 as an example of a section of a fitting to fitting weld. The intended coverage is 20 mm on either side of the weld centreline. However geometric limitations may constrain the region of access.

This example embodiment accommodates the analysis of data files obtained using both 0 and 6 degree offsets as described in the example acquisition procedure above.

FMC UT data from the inspection campaign is provided prior to analysis. A multi processor blade server system may be used to support the Neovision™ analysis software application. This system in some embodiments is linked by an appropriate network to both the acquisition and analysis sites. The network connections should be able to support a data transfer rate 1 GBit/s.

Equipment and Tools

Table 7 below lists example equipment used under this procedure in an example embodiment.

TABLE 7

Hardware and software required for data analysis

| Quantity | Item | Description |
|---|---|---|
| 1 per user | Desktop PC (remote) | 4 GByte memory, Core2 Duo 2.3 GHz or above, 32 bit Windows XP ™, 500 GByte HDD, 1 GBit Ethernet interface, Dual 19" monitors |
| 1 | Client PC | Configured as required to support the Desktop PC |
| 1 | Storage Device | Network based local device for storage of inspection data and processed results. Suggested size 5 TB minimum |
| 1 | Analysis Blade Server | Analysis system consisting of 2 servers and 28 dual processor quad core blades |
| 1 | Linux ™ OS | SUSE |
| 1 | Matlab ™ | Version 2008b |
| 1 | Windows ™ 64 bit XP Server | SP3 |
| 1 | NEOVISION ™ | Version 1.0 or most recent qualified release |

Verification

Data Analysis

Verification of the analysis results is achieved by having a second qualified analyst independently perform analysis on the same data set. In this strategy the initial work is called the primary analysis while the following work is termed the secondary analysis.

Any qualified analyst may perform either primary or secondary analysis on any data set. Generally, the same analyst does not perform both primary and secondary analysis on the same data set.

The value and location of the minimum thickness for both primary and secondary analysis are compared. If the results are within 0.06 mm for the same location in some embodiments the results of the lesser of the two are reported. If the results do not agree within these bounds a third analyst, Lead Analyst, may perform independent evaluation of the data.

Procedure

A Results Coordinator may be responsible to ensure the analysis is conducted per this procedure.

Analysis of FMC Data Sets—Procedure

Analysis of FMC data sets is a serial chain of processing steps, the results of any given step are built upon the results of the preceding steps. Thus any inaccuracy or loss of data may significantly impair all subsequent steps. The reliability of the results is a function of the input data quality.

Figure 61:
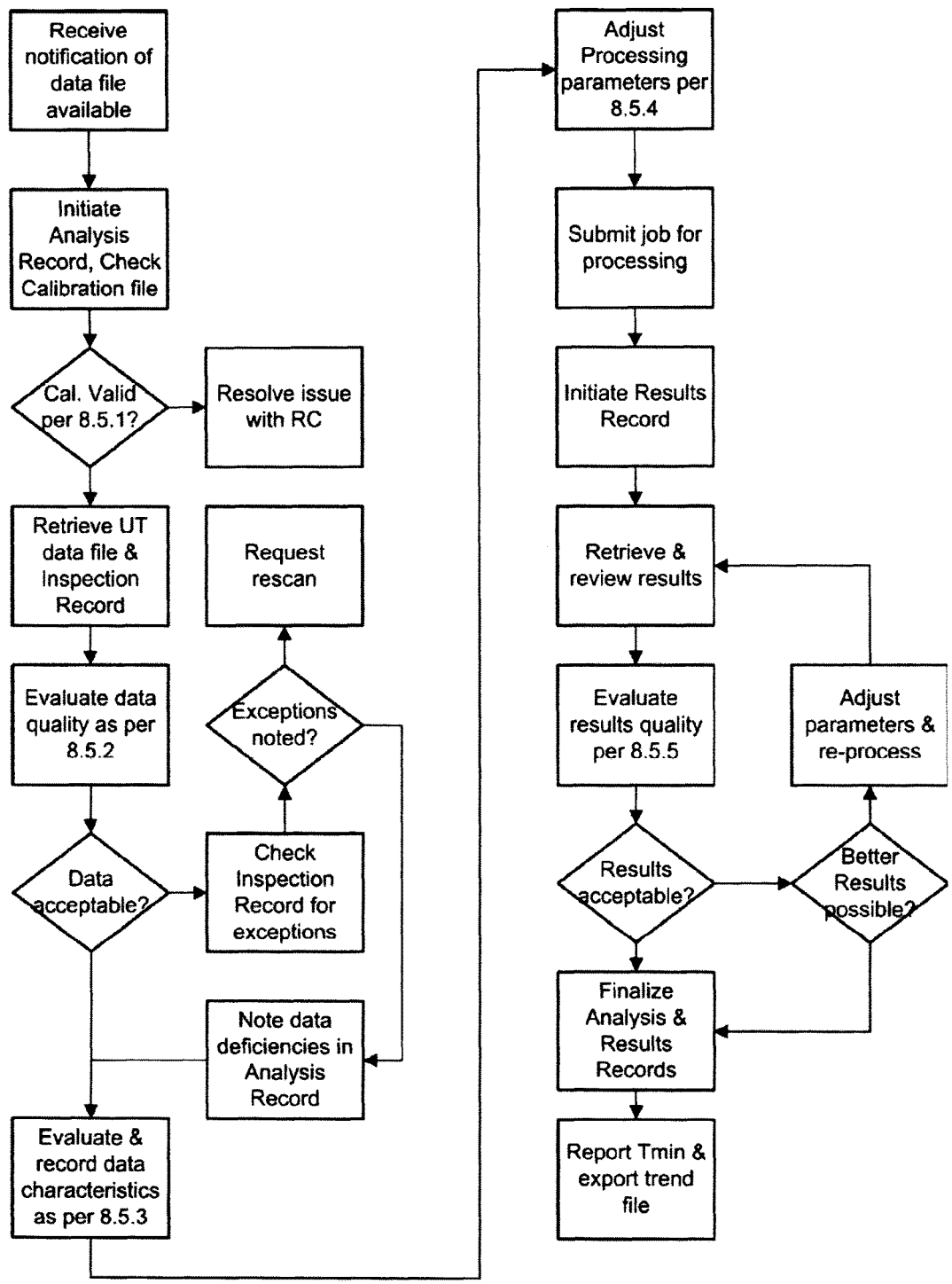
FIG. 61 is a flow chart of steps performed by a data analyst in the process of inspection data analysis according to an example embodiment.

The following two sections discuss the Analysis workflow and Analysis data flow. The workflow describes the steps taken by the analyst in order to generate the final results. See the flow chart presented in FIG. 61. The data flow describes the processing performed by the software. The data flow is summarized here to provide background information when determining the processing parameters. The data analysis algorithms are discussed in the previous sections above.

Analysis Workflow Overview

The first step in the workflow is initiated in the Data Acquisition phase. The Acquisition Operator uploads a completed scan file that meets the acceptability criteria to the Gateway server. A completed Inspection Record generally also accompanies the data file.

The Analyst may then retrieve the UT data file and the corresponding Inspection Record form and initiate an Analysis Record form for the job. The Analyst may then load the UT data file and review the data quality as per acceptance criteria. Any deviations or exceptions from the acceptance criteria should generally already be identified in the Inspection Record for the file. If so, the exceptions may be noted in the Analysis Record. If exceptions to data quality are identified in the UT data that are not reflected in the Inspection Record, the Analyst may initiate a request for rescan of the weld.

The Analyst may then review the file recording the UT parameters that influence the analysis settings. The processing parameters may be adjusted as per the guidelines described above. Processing parameters may be recorded in the Analysis record. The job is then submitted for processing.

When the processing has been completed the Analyst may retrieve the Results file. The Analyst may initiate a Results Record form. The Analyst may evaluate the results against a number of criteria for overall validity. The data may be re-processed with different series of parameters to address areas that do not meet the validity criteria.

When the Analyst has completed evaluation and no further gains in results are obtained, the Analyst may record the minimum thickness information in the Results Record. The Analyst may also produce trend file(s) as specified below.

Analysis Data Flow Overview

Figure 62:
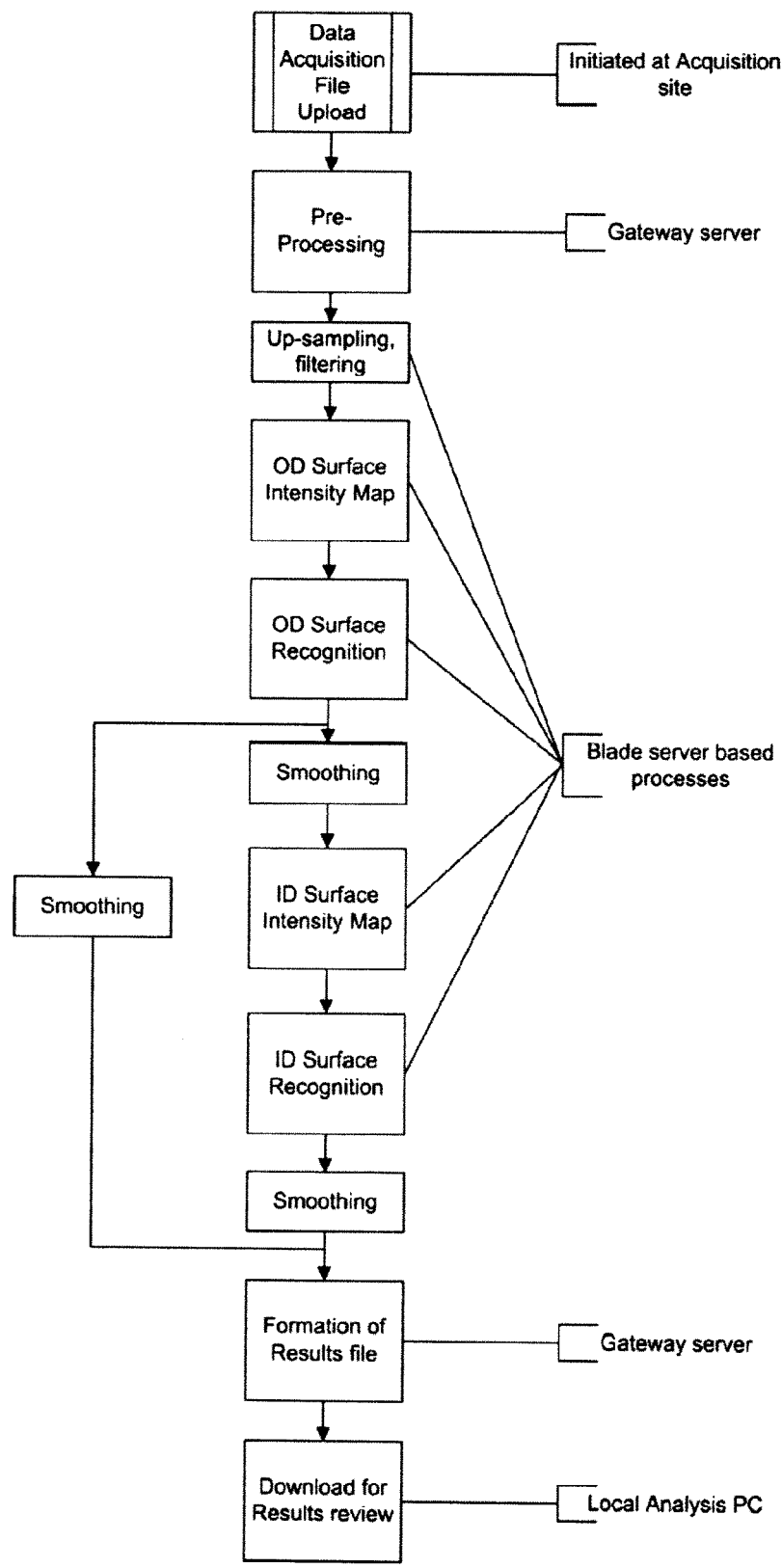
FIG. 62 is a flow chart of steps performed by a data analyst and the various steps applied by the analysis algorithms on the gateway server, blade server, and local analysis PC in the process of inspection data analysis according to an example embodiment.

The analysis data flow is depicted in FIG. 62. In the example embodiment described currently, the process is initiated with the transfer of data from the acquisition site to the Gateway server. The job list will update as the Gateway receives the data, preprocessing of the data begins immediately. Pre-processing includes such steps as data file conversion and digital filtering.

The files for the individual scan frames are downloaded to available processors located in the Blade servers. The following steps are performed in sequential order.

Up-sampling the data set to equivalent of 100 MHz sampling rate.

Compensation for DC offset and digital filtering of UT data

OD Intensity Map formation. The OD Intensity map is formed by evaluating the time indices to each defined point in the inspection volume for each element as per the parameters set. The time indices are summed for each transmitter-receiver pair and the amplitude of the A scan at that time index is summed into the intensity map. The summation process is repeated for all transmitter-receiver combinations that are valid for the specified point in the inspection volume.

OD Surface Recognition. The OD surface is defined using the parameters provided. The X,Z coordinate pairs are generated by the algorithm. Interpolation may be conducted on low level or missing portions of the Intensity Map. The OD Surface is smoothed as an input to the next processing step. A separate smoothing value is applied for output purposes. Note the OD Surface X,Z pairs form part of the Results output.

ID Intensity Map formation. The ID Intensity Map is calculated applying the parameters modified. The ID Intensity Map is calculated in a similar manner as the OD Intensity Map however the X,Z coordinates of the OD surface are used to determine the appropriate time indices for the various transmitter-receiver pairs. Options such as OD signal suppression and signal normalization are implemented at this stage prior to forming the ID Intensity Map.

ID Surface Recognition. The ID surface is defined using the parameters provided. The X,Z coordinate pairs are generated by the algorithm. Interpolation may be conducted on low level or missing portions of the Intensity Map. The X,Z coordinate pairs are smoothed for output purposes. Note the ID Surface X,Z coordinate pairs form part of the Results output.

The processed OD and ID coordinates are transferred back to the Gateway server as part of the Results file. This process is repeated for all individual frame files in the Gateway queue. When all available FMC frame files have been processed the job status on the Gateway server is updated to "post-processing". A short interval after the job status is updated to "complete".

Results Review—Screen Layout

Main Results window

Figure 63:
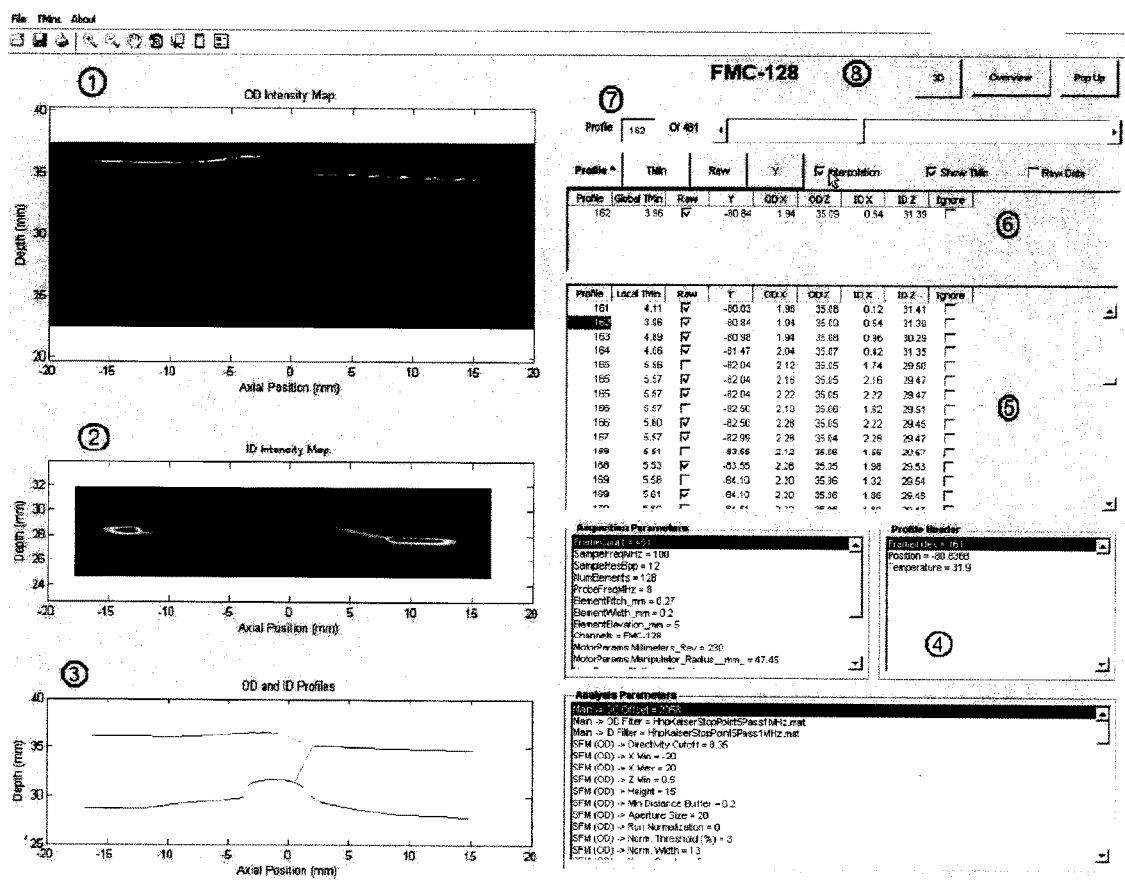
FIG. 63 is an example Main Results window in the NEOVISION™ application used by a data analyst in some embodiments.

The Main results window is illustrated in FIG. 63. The Analyst can use this window to step through the results for each one of the frames. The contents of the Main results window are listed below:

(1) OD Intensity map is plotted in the upper left hand of the Results window (2) ID Intensity map is plotted in the middle of the left hand of the Results window (3) The combined OD/ID profiles (X,Z coordinates) are plotted in the lower left hand of the Results window.

(4) Acquisition, Analysis and File information are listed in the lower right hand of the Results window.

(5) A listing of all TMIN values and locations for each frame, located in the mid right hand side of the Results window.

(6) The global TMIN is found in the upper right side of the Results view.

(7) Controls for scrolling through and sorting the Results data are found in the upper right hand.

(8) Options for generating various 3D views are located in the upper right hand of the Results view.

3D Generation Windows

The 3D Generation windows are a group that provide a 3D reconstruction of the inspected volume. The reconstruction is achieved by plotting the OD and ID profiles either in a linear space or in a radial format. These views are exceptionally useful when assessing OD surface or ID surface related features or evaluating thinning trends. The usefulness becomes compromised however when an appreciable number of the scan profiles have significant interpolation or incorrectly identify Intensity map artefacts.

3D Window

Figure 64:
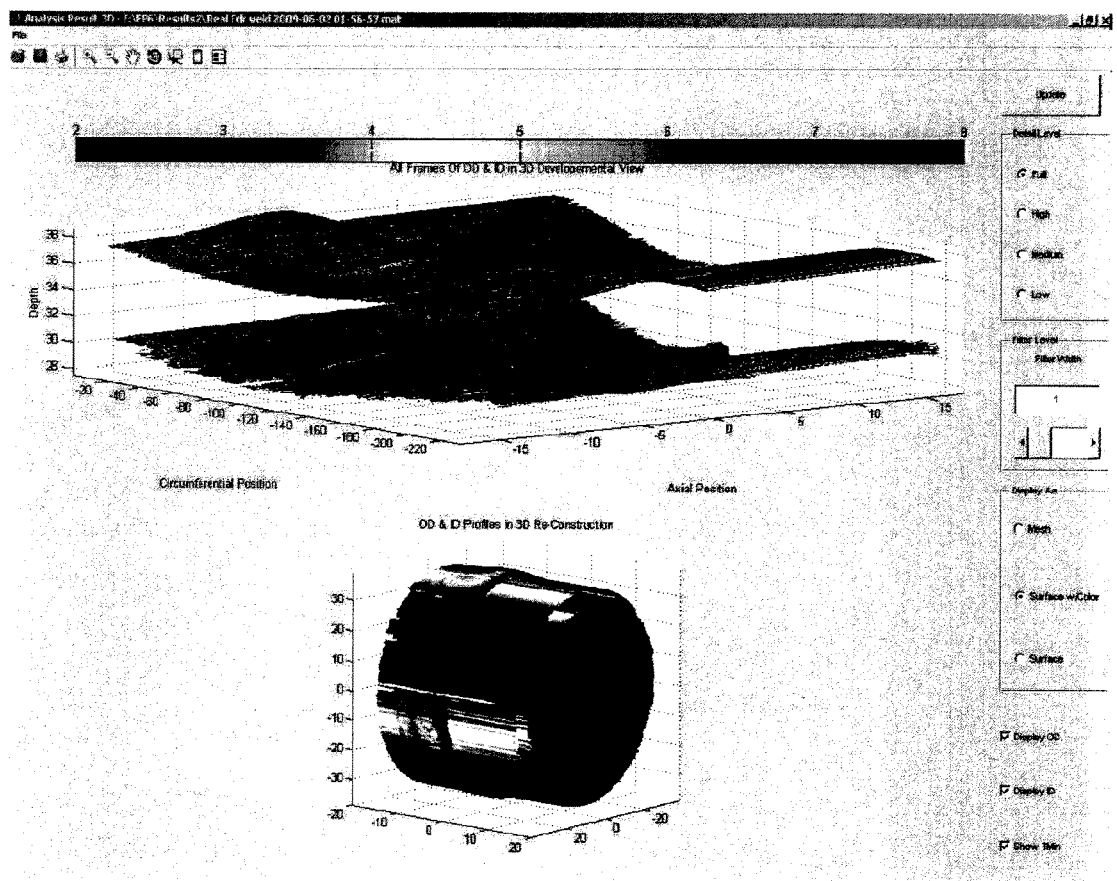
FIG. 64 is an example 3D window in the NEOVISION™ application used by a data analyst in some embodiments.

The 3D window provides the base 3D development and 3D radial views. An example of this window is given in FIG. 64. Display options located on the right side of the window permit the Analyst to vary the degree of detail in the view, the content of the view, surface filtering, pan, rotation, zoom and the colour scale applied.

Overview Window

Figure 65:
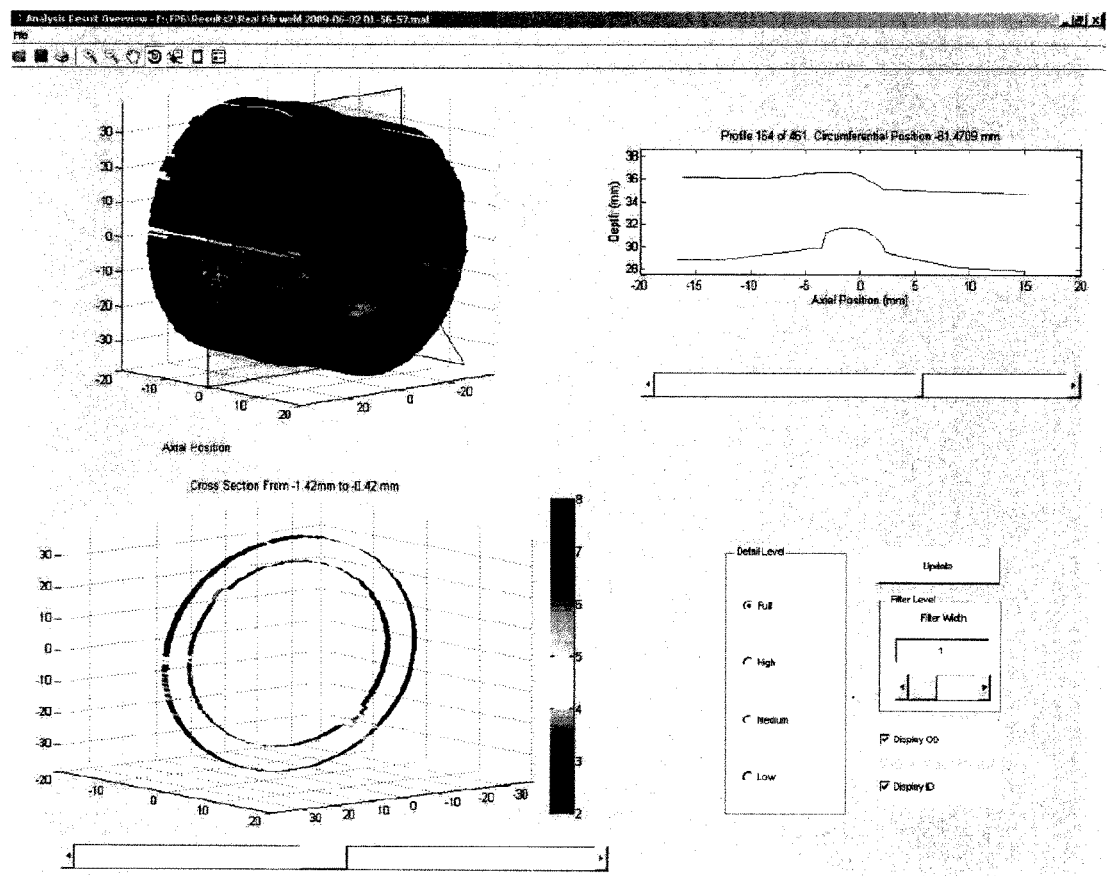
FIG. 65 is an example 3D Overview window in the NEOVISION™ application used by a data analyst in some embodiments.

The Overview window provides the Analyst with the 3D radial reconstruction of the inspection volume. In addition, this view also provides the Analyst with axial and radial profiles as plotted with respect to the inspection volume. This is useful when evaluating thinning trends on either surface. Again the plots may be panned, rotated, zoomed with different surfaces and detail levels presented. See FIG. 65 as an example of the Overview window.

Pop Up Window

Figure 66:
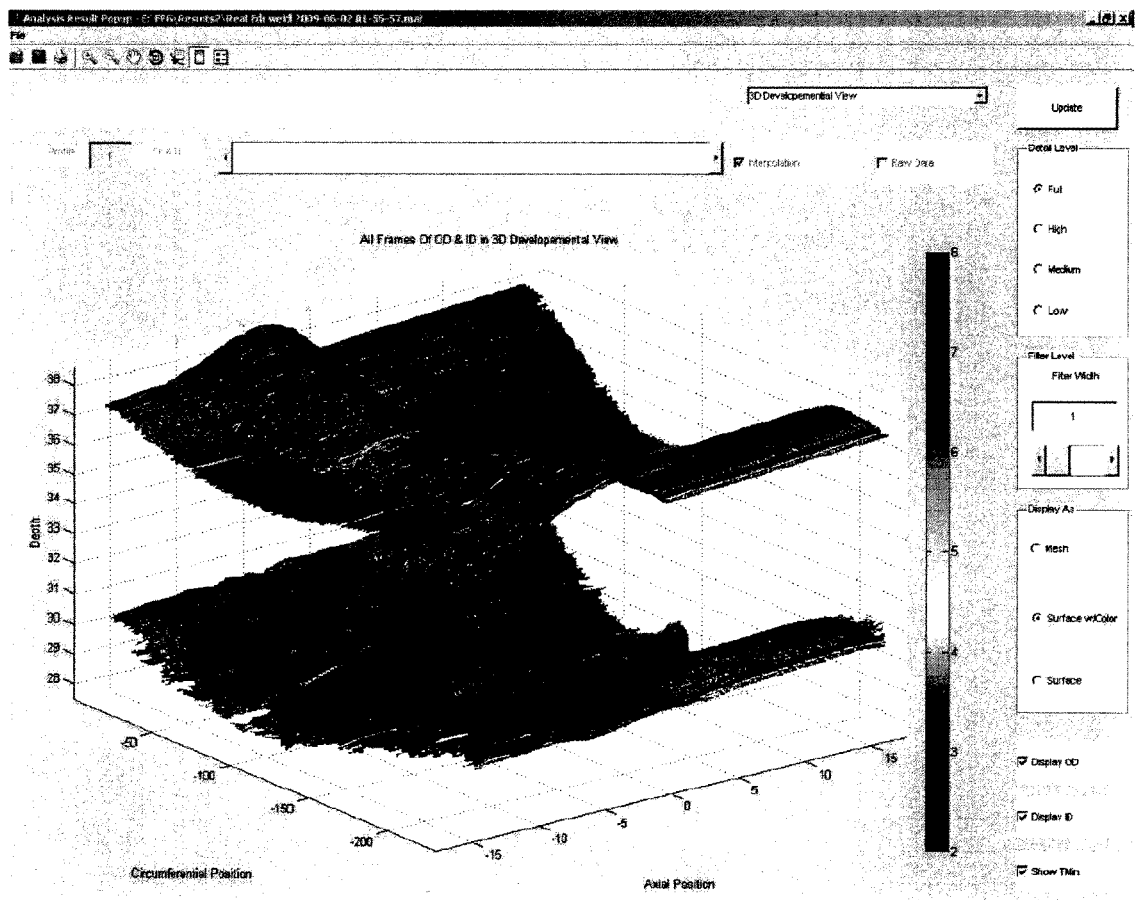
FIG. 66 is an example 3D Pop-up window in the NEOVISION™ application used by a data analyst in some embodiments.

The Pop-up window provides the Analyst with a dedicated window for any of the selected view types. The purpose of this window is to optimize the view for evaluation or reporting purposes. See FIG. 66 for an example of the Pop-up window.

Further Details of Data Analysis Using NEOVISION™ Analysis Method

The following is a brief synopsis of the Analysis method as per FIG. 62. Further detail for each step is provided in the paragraph identified for that step.

Data analysis can begin with notification that a file has status has changed from "Job Pre-processing" to "Job Ready for Processing". The Analyst may be assigned the role of primary or secondary analysis on a given file provided they do not perform the alternate role on the same file. The Analyst may initiate an Analysis Record form for the file to be analyzed.

Step 1: Calibration Verification

If the Analyst has not yet verified the calibration scan and record for the current session, the Analyst may retrieve both the calibration data file and record. Both of these records may be checked for metrics as outlined in Table 8 below. If the calibration is not valid, the Analyst may notify the Lead Analyst to resolve the issue with the Work Package Owner and Acquisition FLM.

TABLE 8

List of Calibration variables and criteria

| Factor | Value | Range | Comments |
|---|---|---|---|
| Relationship to acquisition set-up | Not applicable | Not applicable | Must be same transducer, equipment and personnel as used for data acquisition |
| Validity Interval | | Data acquired within 4 hours of Calibration activity | |
| Element Functionality | Not applicable | No more than 13 missing, no more than 3 adjacent missing | Reject transducer if outside spec |
| Probe delay | 32 DP | +/−2 DP | Note - when at 100 MHz sampling rate |
| Water column DAC | 80% FSH | 50% to 99% FSH | |
| Water column measurement | As per block, see Appendix B | +/−0.01 mm | Note - when at 100 MHz sampling rate |
| Metal path measurement | As per block, see Appendix B | +/−0.03 mm | Note - when at 100 MHz sampling rate |
| Transducer—manipulator alignment | Not applicable | +/−1 degree | Peak to occur on the zero degree flat |
| Temperature sensor function | Not applicable | 15-45° C. | Observed to be functioning and rational |
| Encoder check | 0, 195/245 | +/−0.3 mm | Value dependent upon manipulator in use |

Step 2: Inspection Data Quality and Record Verification

The Analyst may review the UT data file and corresponding Inspection Record as per the criteria provided. Any exceptions to data quality may be noted in the Inspection Record. If exceptions are not identified in the Inspection Record, the Analyst may request a rescan.

TABLE 9

Summary of scan data quality factors

| Number | Issue | Condition | Criteria |
|---|---|---|---|
| 1 | Transducer - Feeder Misalignment | Skew | No more than a cumulative total of 40% of the scan missing |
| 1 | Transducer - Feeder Misalignment | Offset | No more than a cumulative total of 40% of the scan missing |
| 2 | Air Bubbles | Pipe surface: | No appreciable reduction in interface or ID signal amplitude |
| 2 | Air Bubbles | Transducer/ Mirror surface | Not acceptable |
| 2 | Air Bubbles | Water Column | Not greater than 5 scan lines mistriggered |
| 3 | Air Pockets | Horizontal | Air pocket less than 5 consecutive scan lines |
| 3 | Air Pockets | Vertical | Less than 10 elements and no greater than 40 scan lines |
| 4 | Signal Range Limits | Near | Interface signal not closer than 200 DP |
| 4 | Signal Range Limits | Far | Sufficiently close to trigger Interface Gate, should not exceed 900 DP |
| 5 | Electrical Noise | | Not to exceed 5% FSH if uncorrelated, to 2% FSH if correlated |
| 6 | Temperature Reading | | Within range of 15 to 45 C and rational |
| 7 | Missing - Dead Elements | | No more than 13 total, and not greater than 3 adjacent |
| 8 | Interface Amplitude | | Approximately 6 dB beyond 100% FSH on straight pipe sections or sufficient to reliably trigger interface gate on weld cap |

TABLE 9-continued

Summary of scan data quality factors

| Number | Issue | Condition | Criteria |
|---|---|---|---|
| 9 | ID Signal Amplitude | Under pipe material | Observable in Linear Electronic B scan |
| 10 | Inspection Coverage | Axial | Transducer centred over weld - subject to fitting geometry and obstructions |
| 10 | Inspection Coverage | Circumferential | Full circumference scanned - subject to obstructions |
| 11 | Start/End Correspondence | Axial | Start & End UT features in same axial position +/−1.0 mm |
| 11 | Start/End Correspondence | Radial | Start & End UT features in same radial position +/−50 DP |

Step 3: Inspection Data Characteristics Measurement

The Analyst may repeat the review of the UT data measuring specific characteristics of the feeder. These characteristics are then used as a basis for modifying the analysis parameters as required. Some specific characteristics that can be measured are set out in Table 10 below.

TABLE 10

UT Data characteristics related to processing parameters.

| Condition | | Processing Parameter(s) | Comment |
|---|---|---|---|
| Water path to interface | Maximum | X Min, X Max Aperture Height | Increasing water column reduces the effective aperture of the transducer. Excessive Height can introduce ID artefacts if the $2^{nd}$ interface is recorded in the UT data. Insufficient Height and X Max can clip ID Intensity map images in areas of thick cross section |
| Water path to interface | Minimum | X Min, X Max Aperture Directivity Cutoff Height | While reducing the water column height allows signals to be observed across a wider aperture, the $2^{nd}$ water column interface will limit the maximum thickness that can be imaged. The wider aperture is only effective up to the point where Directivity Cutoff limits the number of channels used. |
| Interface signal amplitude | | Normalization OD suppression | Low interface signals amplitude may be compensated for by using Normalization - with the potential of introducing artefacts OD suppression will improve S/N ratio on ID only if minimal/correct interpolation of OD is achieved |
| ID signal amplitude in Linear Electronic B scan | Under weld cap | Normalization | Reducing the threshold levels used for normalization may enhance the ID Intensity map |
| ID signal amplitude in Linear Electronic B scan | Under parent material | Directivity Cutoff Maximum Transmitter-Receiver Difference | Changing both the Directivity Cutoff and Max Tx-Rx Difference may aid in the formation of ID Intensity map. |
| Weld cap width | | Maximum Transmitter-Receiver Difference Normalization | The aspect ratio (width to height) is an indication of what may be observed under the weld cap, the higher the ratio, the better the reconstruction of the ID |
| Weld cap height | | NA | Only relevant with respect to weld cap width, see above |
| Weld cap interface | | Normalization | Indication of ripple, high modulation may defeat ID reconstruction in one or |

Step 4: Parameter Variation and Processing

The default parameters can be applied for the first pass in the Analysis process. Specific Inspection data characteristics may warrant changing some processing parameters. The parameters used for each pass may be saved to a unique file associated with the Results file.

Step 5: Results Review and Verification

The Analyst may retrieve and review the results. Depending upon the findings of the Results review, the Analyst may choose to re-process the data one or more times for the entire file or subsets of the file. The Analyst may save each set of processing parameters under a separate file name for each round of processing.

Step 6: Reporting Results and Documentation

The Analyst may record specific results information in the Results record. The Analyst may also create a Trend file. Supplementary outputs may be included as well.

Indices Used for Determining Acquired UT Data Quality

In some embodiments, the software will provide the user with additional information to aid the analyst in determining the quality of acquired UT data. In some embodiments, this analysis may take place during Step 5: Results review and verification.

In an example embodiment, two indices are provided to the analyst to aid in the analysis. The first index is referred to as the "Theoretical Quality Index". This is based on the geometry of the detected OD surface, and indicates the theoretical best possible quality level achievable for ID UT. The second index is referred to as the "Actual Quality Index". This is based on the ID intensity map from the collected UT data.

The Actual Quality Index is generated using the collected UT data. First, the software takes the average of the whole intensity map, ignoring some small areas based on the detected surface. Specifically, the ignored areas are those that extend downwards in the Y axis from the detected surface on the intensity map. By ignoring these areas when calculating the average, the calculation removes all parts of the intensity map that contribute to the detected surfaces. The lower the average intensity of the rest of the intensity map is, the better the "Actual Quality Index" value will be. To arrive at the Actual Quality Index value, this calculated average is compared to one or both of two numbers:

1) the maximum intensity found anywhere in the intensity map (which will likely be found in one of the areas ignored by the averaging), and/or
2) the maximum possible intensity, based on theoretical UT values that could be achieved based on OD geometry.

Figure 78:
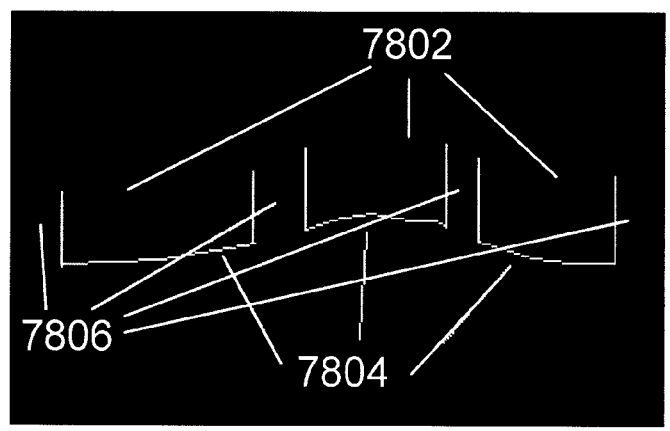
FIG. 78 is an example intensity map showing the areas of the intensity map used to generate the Actual Quality Index.

FIG. 78 shows an example implementation of generating the Actual Quality Index from an intensity map. The detected boundary 7802 is used to identify those areas 7804 extending downwardly therefrom on the Y axis. These areas 7804 are ignored, and only the remaining areas 7806 are used to generate an average intensity value. The lower this average intensity is, the better the Actual Quality Index.

Processing Software for Pipe Weld Inspection

Software used to perform the various procedures is described in detail below as part of an example embodiment. The tables A1 to A10 at the end of the Description provide example functions and parameters to be used within the context of this example embodiment. The sections below describing the software used in this example embodiment are intended to be illustrative only, as a possible implementation of the system described in more general terms above.

Software Architecture

The Feeder Weld Area Thickness Measurement Tool (WPIT) contains a software suite to acquire, analyze and display feeder weld area profiles to determine minimum feeder thicknesses caused by Flow Assisted Corrosion.

Neovision™ is the primary user interface software, responsible for acquisition of the ultrasonic data, control of the probe manipulator, setup of the analysis parameters, communication between itself and the Grid Middleware program in Gateway mode to submit analysis job and retrieve combined result, and initiation of the Results Display program to display the analyzed result. This software can only be executed under the Windows™ operating system.

The Grid Middleware program is a java program and it has 2 modes: Gateway mode and Agent mode.

In Gateway mode, it communicates with Neovision™ and receives an analysis job request from it. It breaks down the Neovision™ ultrasonic data file into individual FMC data files by invoking the Exporter program. It controls the flow of data to the Grid Middleware Agent, by sending FMC data out and receiving FMC result files back. It then merges all the FMC result files into one combined result file by invoking the Merger program. The combined result file is then sent back to Neovision™ based on user request.

In Agent mode, it receives FMC data files from the Gateway and starts up a set of Analysis programs so that the data can be analyzed. It reports back to the Gateway on its status and the statuses of the Analysis programs. When the FMC result files are created by the Analysis programs, it sends the result files back to the Gateway. It is designed so that each server needs one instance of the Agent and the Agent controls and invokes a set of Analysis programs as defined and limited by configuration settings.

The Grid Middleware program is written in Java and it can be run on Windows™ operating system or Linux™ operating system. For Gateway mode, it must be executed on Windows operating system since it needs to invoke the Exporter program, which only works on Windows™ OS. A typical deployment includes a 64-bits Windows™ server which runs the Grid Middleware in Gateway mode, and a farm of 64-bits Linux™ Servers which run the Grid Middleware in Agent mode. For a small-scale deployment, the Grid middleware will be executed on the same machine as the Neovision™ program and it will contain one instance of the Grid Middleware running in Gateway mode and one instance of the Grid Middleware running in Agent mode.

The Exporter program exports the Neovision™ data file into a set of FMC data files for the Analysis program. The FMC data file contains only one set of FMC signals and it is saved as MATLAB™ data file. These FMC data files will be used as input file for the Analysis program. This program can only be executed under Windows™ OS. This program is invoked by the Grid Middleware program in Gateway mode.

The Analysis program is a MATLAB™ stand-alone executable program which can be run on Windows™ operating system or Linux™ operating system. With a single set of FMC data, it calculates 2D intensity map for the OD and determines the OD boundary definition. When the OD boundary is defined, it then calculates the 2D intensity map for the ID and determines the ID boundary definition. Using the OD and ID boundary definitions, it calculates the minimum thickness (TMin) for this pair of OD and ID boundaries. It then converts the reportable results into a standardized format and saves them. The Analysis program outputs a single result file which contains all the reportable results. It is a highly memory intensive and CPU intensive program. This program is run by the Grid Middleware program in Agent mode.

The Merger program takes output analysis result files from the Analysis program and combines all the reportable results to create a single combined result output file. By combining the OD and ID boundaries from each profile, the Merger program can reconstruct a 3D representation of the scan and recreate the OD and ID surfaces. The Merger program is written in MATLAB™ and it is a MATLAB™ stand-alone executable program. It is run by the Middleware in Gateway mode.

The Result Display program displays the combined result output file so that the user can inspect and interrogate the result. It displays the 2D Intensity Maps, the OD and ID boundaries, the TMin for each profile and the absolute TMin for the whole data file. It also displays the 3D representation of the scan to give user a better understanding of the data. The Result Display program provides a simple user interface so that user can filter out unreasonable TMin values and profiles. Users can create the thickness trend data file and export the filtered data to other CAD (Computer-Aided Design) programs for further investigation such as stress analysis. It runs on the same machine that runs Neovision™. It is a MATLAB stand-alone executable program and it is invoked from Neovision™.

Data Pathway

Here are the data flow steps when analyzing the Neovision data file:

(1) After the Neovision™ data file is acquired, either the acquisition operator or the analyst can submit the valid data file into Neovision™ and Neovision™ will send the data file to Grid Middleware Gateway mode and create a job for this data file.
(2) The analyst selects the job and inspects the data file. The analyst enters the analysis parameters after reviewing the data file and starts the job. Neovision™ sends a request to the Grid Middleware and the Grid Middleware Gateway agent will start the analysis by calling the Exporter program
(3) After the Exporter program converts the Neovision™ data file into individual FMC data files in MATLAB™ format, it sends them back to Gateway.
(4) When the Gateway finds an available Agent machine, it will send FMC .MAT files to the Grid Middleware Agent.
(5) The Agent creates a node and invokes the Analysis program with the FMC .MAT file as one of the input parameters.
(6) After the Analysis program completes its calculation, it sends the Result FMC .MAT file back to the Agent.
(7) The Agent sends the Result FMC .MAT file to the Gateway and informs the Gateway that it has an available node for more analysis computation.
(8) When Gateway receives all Result FMC .MAT files for the Neovision™ data file, it will invoke the Merger program and send it all the Result FMC .MAT files.
(9) The Merger program will extract reportable data and merge individual results into a meaningful order and output a Combined Result file back to the Gateway.
(10) The Gateway informs Neovision™ that the result is ready. The user then retrieves the Combined Result file from the Gateway via Neovision™ and saves a local copy of the Combined Result file.
(11) After Neovision™ receives the Combined Result file, it invokes the Results Display program to display the data. The user can review, inspect, modify and export the data in the Result Display program.

Grid Middleware Component

The grid middleware component can be run in two modes which behave very differently. One is the gateway and the other is the agent. A functioning analysis system will have one instance of Neovision™, one gateway, and one or more agents. The gateway receives messages from both Neovision™ and the agent(s) during analysis. Generally, the gateway does not initiate communications, though there are exceptions to this.

FMC Data Set Analysis

Analysis of the FMC data is implemented as described above.

Where the acquisition software delivers multiple FMC data-sets to the analysis software, the analysis software analyzes each FMC data-set received independently and prescriptively. Thus, a description of the analysis of a single FMC data-set is sufficient to describe the analysis of all FMC data-sets, in that the analysis process for all datasets is identical. Upon completion of the analysis of the FMC data-sets, the output (OD and ID boundary coordinates) are input into the Graphical Output Process.

Graphical Output Process

Create Profile-Based Result

The Profile-Based Result is based on the analysis result. Data is remapped and axes values are changed as needed. Thickness values for each profile are created. The scan position and other profile based information are created in this section.

It takes a small amount of time (about 3 seconds at maximum resolution) for each profile to create the Profile-Based Result. However, to create 460 profiles together, even using MATLAB™ Vectorization technique, it will still take a significant amount of time in the whole process. In order to shorten the total execution time, the Profile-Based Result is created at the end of the analysis program. So the Profile-Based Result is created in parallel without any significant delay on the execution time.

Merge Result

Merge Result is a stand-alone MATLAB™ executable. It merges individual Profile-Based Results in a scan and creates a result file. If the result file already exists, it will merge the specified profiles of Profile-Based Results into the result file.

One of the main tasks of Merge Result is to reconstruct the 3D representation of the OD and ID. Since MATLAB™ uses a 2D matrix to represent any surface and uses the matrix row and column indices to maintain the logical relative positions between data points, Merge Result will merge the OD and ID based on their relative position by first determining the global spacing resolution and the limits. The result from each profile is then remapped, and valid set of data points is inserted into the final OD and ID matrices.

The final profiles for the OD and ID are saved into matrices based on their profile ordering. A sorting vector is calculated based on profile's position and their relative positions so that it can be used when displaying the OD and ID in 3D views.

All Profile-Based Results are saved into the result file as different structures. All the useful information is stored in the merged result file, so there is no need to keep the output file from the analysis command line program. Invalid, partial (OD only), and empty profiles are merged into the result as null value when the required data does not exist.

Merge Result gathers each profile's minimum thickness and saves them into a matrix so that it is easier for the Display Program to access the information.

One of the limitations of the Merge Result is that the Profile-Based Result from different profiles must have the same spacing resolution. Merge Result will skip the profile if the spacing settings are not the same.

Also, the global spacing resolution and the limits are determined when the result file is being created by iterating the profiles until the first valid profile that has the information is found. Even if newer Profile-Based Results are merged in which have larger ranges, the Merge Result will only merge based on the limits defined previously. If the user wants to re-create a different spacing resolution and different range limit of data, the result file must be removed first so that the global spacing resolutions and limits can be re-determined. Within the FP6 analysis steps, this requires the user to create a new job so that there will not have any existing result file and resubmit the scan for analysis again.

Display Result Main Window

This is the main GUI for the Display Result program. All other display windows are created based on this window. The user can invoke the rest of the display windows from this window and the user can also modify TMin and export data from this window.

It has an initialize function (Initialize) to setup data by reading the result file and cache the data into memory. It loads global setting from a settings file, which defines most of the display properties and the trend output properties. It loads an analysis parameter mapping file so that when the program displays the internal analysis parameters, the parameter names can be the same or similar to the one used in the analysis parameter window in NeoVision™.

This window displays Profile-Based Results by accessing the individual structure for each profile saved in the result file. They are the OD intensity map, ID intensity map, and the OD & ID profiles. It also displays the TMin information and the parameter values for the scan settings, the analysis settings and the profile information.

When the user launches the sub-display windows such as popup, overview or 3D, the program stores the handles from those figures (handlePopup, handleOverview, and handle3D) so that it could close all sub-windows when it is terminated. It also uses this list of handles to transmit the Modified TMin information to the sub-windows.

A custom data cursor is added into the program. All windows use the same custom function, CursorUpdateText, to display the data cursor.

There is no sortable 'uitable' control in MATLAB™ so the software has to re-create the feature manually for the TMin lists. Based on the button the user clicks, different sorting parameter values are set and the sortUpdateListGUI amd Display™ in are called to perform the sorting and display.

Display Popup Window

The Popup window is based on the main window and this is the only window that can have more than 1 instance within the Analysis Display program.

The main usage of this window is to allow the maximum screen resolution by displaying a single figure only. The user can view a larger version of any of the figures shown in other display windows.

Similar to other sub-windows, the Popup window can be invoked directly and a stand-alone executable program can be created.

Display Overview Window

The Overview window is based on the main window and it is a singleton window.

The main usage of this window is to provide a high level overview of the scan. Along with the 3D view of the scan, it provides the cross section view and the axial view of the scan so that user can inspect the result. Refer to the 3D window for more details and description of the 3D View.

Similar to the popup window and the 3D window, a median filter can be applied to the display data in the circumferential direction. This should reduce noise and data error so that user can review the data effectively.

Similar to the popup window and the 3D window, four levels of data sampling are defined. The default level is medium and it should have the best detail and performance combination.

The viewing plane of the cross section view and the axial view are also drawn on the 3D view to enhance the visual representation of the data.

Similar to other sub-windows, the Overview window can be invoked directly and a stand-alone executable program can be created.

Display 3D Window

The 3D window is based on the main window and it is a singleton window. The main usage of this window is to provide the 3D representation of the scan. It contains the developmental view and 3D view. The developmental view displays all the profiles of data based on their profile ordering and displays them side by side. The 3D view is the 3D reconstruction of the scan.

Both views can be displayed as 'surf' or 'mesh' objects in MATLAB™ drawing. For 'surf', color can be used to represent the thickness of the feeder, or the surface can be drawn monotonically to review the detail of the surface.

Similar to the popup window and the Overview window, a median filter can be applied to the display data in the circumferential direction. This should reduce noise and data error so that the user can review the data effectively.

Similar to the popup window and the Overview window, four levels of data sampling are defined. The default level is medium and it should have the best detail and performance combination.

Similar to other sub-windows, the Overview window can be invoked directly and a stand-alone executable program can be created.

Modify TMin

The functionality of Modify TMin is handled by the LoadModifiedTMin, SaveModifiedTMin, DisplayTMin, TMinUitableCellEditCallback and menuui_ExportToFigures_Callback functions.

LoadModifiedTMin reads the MATLAB™ data file and loads modified TMin information into the program.

SaveModifiedTMin writes modified TMin information into data file.

DisplayTMin will recreate the TMin lists based on sorting mode and ignore list, and display the TMin lists on the main window.

TMinUitableCellEditCallback is invoked when the user modifies the local TMin list by selecting the ignore checkbox to remove or re-add TMins from the list. This function will update the internal definition of the TMin list. Note that when the user removes a TMin from the list, it removes that profile of the scan from the display, not just the TMin definition. The profile removal will affect the display and the export result as those profiles will be omitted.

menuui_ExportToFigures_Callback is invoked when the user selects the 'Export Modified TMins To Other Window (s)' option from the menu. The modified TMin list will be sent to all sub-windows and the data on those windows will be updated. It is a two part process where the user will need to refresh individual sub-windows to display the updated TMin information.

Export 3D Point Cloud

The Export 3D Point Cloud exports the OD and ID surface as point cloud values.

The output filenames will be selected by the user and the OD and ID surfaces will be saved into separate output file with file extension .xyz, which is a defined point cloud file extension for SolidWorks™.

The output file format contain a simple point definition per line and the point is defined as 'x y z', where x, y, z are the coordination of the point.

Export Trend Result

Export Trend Result exports the trend information of the scan to an Excel™ file.

Any existing export file will be deleted.

The trend information contains the channel name, the global TMin list, and the TMin Trend.

The global TMin list contains the following fields:
1. Profile Number
2. TMin
3. Cric Position (mm)
4. OD Axial Position (X in mm)
5. OD Depth (Z in mm)
6. ID Axial Position (X in mm)
7. ID Depth (z in mm)

The TMin Trend contains equally spaced thickness values from the scan. Each line represents a scan profile with the following fields:
1. Profile Number
2. Cric Position (mm)
3. Axial Positions (mm)

Axial Positions are equally spaced throughout the profile. When the thickness is not available for the particular sampling point, it will be marked as 'NaN'. When the thickness for a particular sampling point is only available using interpolated values, it will be marked as 'IV'. If a particular sampling point is ignored based on the modified TMin selection, it will be marked as 'Ign'. Currently the ignored selection only applies to the profile so the whole row will be marked as 'Ign'. All trend information will be saved into a new tab in the Excel™ file and the tab name is the channel name.

TABLE A1

Preprocessing Functions

| Function Name | Input Data | Input Data Class | Input Data Description | Output Data | Output Data Class | Output Description |
|---|---|---|---|---|---|---|
| filtfilthd | 1. Three dimensional Matrix (real). 2. Digital software filter. | 1. Single 2. Filter object | 1. Full matrix RF data-set. 2. Filter object which defines frequency attenuating properties of the digital filter. | Three dimensional matrix. | Single | Filtered full matrix RF data-set. |
| ndimhilbert | Three dimensional Matrix. | Single | Full matrix RF data-set. | Three dimensional matrix | Single (complex) | Full matrix analytic time-domain data-set. |

TABLE A2

OD Imaging Parameters

| Variable | Class | Description |
|---|---|---|
| blockSize | Single | A Scalar defining the size of the physical aperture used in SFM imaging. This scalar can range from 1 to the size of the array. |
| directivityCutoff | Single | A real number between 0 and 1 (inclusive) used to determine intensity map coordinates considered (with respect to the SFM algorithm) to reflect ultrasonic Waves to/from individual array elements. if the calculated directivity from an element to a coordinate in the intensity map is lower than directivityCutoff, then that element is programmatically not considered to reflect sound to/from the coordinate in question. To calculate the directivity of an element to a specified location, a formula which approximates directivity is used (see Theory Manual [R-2]). |
| xMin | Single | A real number defining the lower limit of x-components of intensity map coordinates (in metres). xMin is less than xMax. X-components of intensity map coordinates will range from xMin to xMax. |
| xMax | Single | A real number defining the upper limit of x-components of intensity map coordinates (in metres). xMax is greater than xMin. xMin is less than xMax. X-components of intensity map coordinates will range from xMin to xMax. |
| xSpacing | Single | A vector of length n specifying x-spacings at which to iteratively perform computation of intensities at intensity map coordinates. A total of n iterations of intensity computations are performed (assuming intensity computations do not need to be further broken up to satisfy memory requirements). Coarser spacings are specified toward the lesser indices of the |

TABLE A2-continued

OD Imaging Parameters

| Variable | Class | Description |
| --- | --- | --- |
| | | vector while finer spacings are specified toward the finer indices of the vector. Additionally for every i between 1 and n-1, dx(i + 1)/dx(i) is a positive integer. |
| zMin | Single | A real number defining the lower limit of z-camponents of intensity map coordinates in metres). zMin is greater or equal than zero.<br>z-components of intensity map coordinates will range from x to x + height, where x is the maximum of zMin and the distance corresponding to the minimum delay in lookupTable.Offset minus MinDistanceBuffer. |
| zSpacing | Single | A vector of length n specifying z-spacings at which to iteratively perform computation of intensities at intensity map coordinates. A total of n iterations of intensity computations are performed (assuming intensity computations do not need to be further broken up to satisfy memory requirements).<br>Coarser spacings are specified toward the lesser indices of the vector while finer spacings are specified toward the finer indices of the vector. Additionally for every i between 1 and n-1, dz(i + 1)/dz(i) is a positive integer. |
| height | Single | A real number representing a distance (in metres). |
| minDistanceBuffer | Single | A real number representing a distance (in metres).<br>z-components of intensity map coordinates will range from x to x + height, where x is the maximum of zMin and the distance corresponding to the minimum delay in lookupTable.Offset minus minDistanceBuffer. |
| zoomPercentage | Single | A vector of length n − 1 implicitly specifying coordinates in the intensity map to focus around upon iterative computation of coordinate intensities,<br>For i between 1 and n − 1, zoomPercentage(i) contains a real number between 0 and 1 inclusive. On iteration i + 1 of coordinate intensity computation, where lmax is the maximum intensity calculated in the intensity map, the coordinates in which to focus around are those of intensity greater than zoomPercentage(i) * lmax. |
| runNorm | Boolean | This determines whether or not normalization will be run on the input data. If this value is false, then the values of normThresh, normWidth and normRunUp are unimportant as they will not be used. |
| normThresh | Single | A real number greater than 0 and less than or equal to 100. This number specifies the cutoff envelope height of wave packets to be normalized in A-Scan data. Where we let 'y' be the maximum envelope value of all FMC data, wavepacket information with peak height greater or equal to threshold * y/100 will be normalized. All other information in the A-Scans will be set to 0.<br>Recall the envelope of hilbertized data is simply its magnitude. |
| normWidth | Single | A positive scalar greater than 1 and less than or equal to any nonzero length of AScan contained in the FMC data.<br>This number specifies the distance (in digitization points) between distinct wave packets in an A-Scan. If the distance between envelope peaks greater than the threshold variable exceeds the variable width, then envelope peaks are considered to belong to distinct wave packets. Otherwise, the envelope peaks are considered to belong to the same wave packets. |
| normRunUp | Single | A positive scalar greater than 1 and less than or equal to any nonzero length of AScan contained in the FMC data.<br>This number specifies the number (in digitization points) of A-Scan values ahead of envelope peaks with values greater than the threshold variable to normalize along with the envelope peaks themselves. |
| gratingThreshold | Single | A real number greater than or equal 0 and less than or equal to 100.<br>This value is used to help reduce the grating present in the final intensity map. It works by removing low intensity contributions from each aperture. In each aperture, this threshold is applied as follows. The highest intensity location in that threshold is the standard to which 100% is measured. Every other location in the intensity map must be at least gratingThreshold percentage of this value in order to be included in the final summation, otherwise it is zeroed out. |
| totalMemory | Single | This value is the amount of memory available to this node, in bytes. It is used to fragment the computation of certain values, if necessary. This allows the program to fit within memory constraints. If space allows computation to occur without fragmenting, no fragmenting of computation occurs. |

TABLE A2-continued

OD Imaging Parameters

| Variable | Class | Description |
|---|---|---|
| tempOverride | Boolean | This value determines whether or not the user input temperature value will override the value stored in the slice data file. If this value is false, the value for tempValue is unimportant as it will not he used. |
| tempValue | Single | This is the user input value for the temperature. This value will be used for the temperature in calculations if the tempOverride value is true. Otherwise, this value will be ignored. |

TABLE A3

SFM Functions

| Function Name | Input Data/ Input Data Class | Input Data Description | Output Data/ Output Data Class | Output Description |
|---|---|---|---|---|
| normalize FMClocal3 | 1. 2D matrix/single (complex). 2. scalar/single 3. positive integer/single 4. positive integer/single | 1. Filtered and hilbertized FMC data set 2. cutoff threshold used for normalization. 3. minimum distance (in samples) between wave packet peaks exceeding cutoff threshold such that the wave packets are considered distinct. 4. distance (in samples) to normalize wavepacket information before detected peaks exceeding cutoff thresholds. | 1. 2D matrix/single (complex). | 1. FMC data set with normalized peaks. All unnormalized data is set to zero. |
| prepareraw dataforod | 1. 2D matrix/ single (complex). 2. positive integer/single 3. positive integer/single. 4. 2D matrix/single. | 1. Filtered and possibly normalized (if user has set the analysis to run normalization) FMC data set. 2. number of probe array elements 3. size of the aperture 4. 2D matrix whose entries indicate the column in the FMC data set for which the A-Scan is stored, for each transmitter/receiver pair. The transmitter and receivers correspond to the rows and columns of the matrix, respectively. | 1. 2D matrix/ single (complex). | 1. FMC data set ordered for correct interpretation in sfmzoom2 algorithm. A-Scans belonging to specific transmitter/receiver pairs are expected at specific columns in the FMC data set. |
| pre_compute arraycoords | N/A | N/A | 1. column matrix/single. | 1. Entry x in the column matrix is the x-component position or probe array element x. |
| o_compute initcoords3 | 2D matrix/double | 2D matrix whose entries correspond to delay (in samples) between transmission and recording of ultrasonic data for transmitter/receiver pairs. The row and column of each entry | 1. column matrix/single 2. column matrix/single 3. column matrix/single | 1. x-coordinate for first pass of intensity map calculation. 2. z-coordinate for pass of intensity map |

TABLE A3-continued

SFM Functions

| Function Name | Input Data/ Input Data Class | Input Data Description | Output Data/ Output Data Class | Output Description |
|---|---|---|---|---|
| | | corresponds to its transmitter and receiver pair respectively. | | calculation. 3. profile number for first pass of intensity map calculation. For each (x, z) pair, the profile number indicates which FMC data set this pair belongs to. Note: this variable array is used for parallel processing of OD intensity maps belonging to different data sets. If only one data set is being processed at a time, every entry in the profile array is set to 1. |
| o_compute currfinecoords4 | 1. column matrix/single 2. column matrix/single 3. column matrix/single 4. scalar/double | 1. x-coordinates of calculated intensity map coordinates. 2. z-coordinates of calculated intensity map coordinates. 3. profile numbers for calculated intensity map coordinates. 4. loop iteration | 1. column matrix/single. 2. column matrix/single. 3. column matrix single. | 1. x-coordinate of neighbourhood of intensity map coordinates exceeding specified intensity cutoff. 2. z-coordinate of neighbourhood of intensity map coordinates exceeding specified intensity cutoff. 3. profile number of neighbourhood of intensity map coordinates exceeding specified intensity cutoff. |
| o_currcompute indices andvisibility | 1. column matrix/single 2. column matrix/single 3. column matrix/single 4. column matrix/single | 1. probe array x-coordinates 2. x-coordinates used for imminent intensity map computation 3. z-coordinates used for imminent intensity map computation. 4. coordinate profiles used for imminent | 1. 2D matrix/single 2. 2D matrix/logical | 1. Entries of matrix yield travel times (in samples) for a given probe array element and intensity map coordinate. The row of the matrix corresponds |

TABLE A3-continued

SFM Functions

| Function Name | Input Data/ Input Data Class | Input Data Description | Output Data/ Output Data Class | Output Description |
|---|---|---|---|---|
| | | intensity map computation. | | to the (x, z) coordinate index and the column of the matrix corresponds to the probe array element index.<br>2. Entries of matrix yield 'true' if an intensity map coordinate falls within the the specified user defined element directivity, and 'false' otherwise. The row of the matrix corresponds to the (x, z) coordinate index and the column of the matrix corresponds to the probe array element index. |
| sfmzoom2 | 1. 3D Matrix/single (complex).<br>2. 1D column matrix/single<br>3. 2D matrix/single<br>4. 2D matrix/logical<br>5. 3D matrix/single<br>6. scalar/single | 1. Filtered and hilbertized FMC data.<br>2. Column matrix indicating profile number for each row index in input items 2 and 3.<br>3. Entries of matrix yield travel times (in samples) for a given probe array element and intensity map coordinate. The row of the matrix corresponds to the (x, z) coordinate index and the column of the matrix corresponds to the probe array element index.<br>4. Entries of matrix yield 'true' if an intensity map coordinate falls within the the specified user defined element directivity, and 'false' otherwise. The row of the matrix corresponds to the (x, z) coordinate index and the column of the matrix corresponds to the probe array element index.<br>5. Entry [i, j, k] of the matrix gives the | 1. 1D Matrix/single | 1. Computed intensities for coordinates stored in indices identical to those of input item 2. |

TABLE A3-continued

| | | SFM Functions | | |
|---|---|---|---|---|
| Function Name | Input Data/ Input Data Class | Input Data Description | Output Data/ Output Data Class | Output Description |
| o_compute coordinates above cutoff | 1. 1D column matrix/single. 2. 1D column matrix/single. 3. 1D column matrix/single. 4. 1D column matrix/single. 5. 1D column matrix | samples between pulse transmission from element j and receiver reception by element k 6. Grating threshold that values from each aperture should pass before being added to the main intensity map 1. x-coordinates used in intensity map computation 2. z-coordinates used in intensity map computation. 3. coordinate profiles used in imminent intensity map computation. 4. calculated intensities for each coordinate/profile combination. 5. Entry i in column matrix gives the intensity cutoff for profile i such that new coordinates around coordinates with intensities exceeding the intensity in entry i will have corresponding intensities calculated. | 1. 1D column matrix/single. 2. 1D column matrix/single. 3. 1D column matrix/single. | 1. newly defined x-coordinates. 2. newly defined z-coordinates. 3. profiles for given newly deifned coordinates. |

TABLE A4

| | Boundary Recognition Parameters | |
|---|---|---|
| Variable | Class | Description |
| sigmaMetres | Double | A scalar which defines the size of the convolution window to implement in Canny edge detection. |
| thresholdParams | Double | A two element vector where thresholdParams(1) defines the low cutoff threshold and thresholdParams(2) defines the high cutoff threshold in Canny edge detection. |
| SEDimsZX | Double | A two element vector (containing only positive integers) defining rectangular structuring element parameters used to dilate the edge detected boundary. SEDimsZX(1) contains the rectangular structuring element height (z-direction) while DEDimsZX(2) contains the rectangular structuring element width(x-direction). |
| maxSEDims | Double | A two element vector (containing only positive integers) defining rectangular structuring element parameters used to dilate the pixels of maximum intensity found in vertical slices of the input intensity map. maxSEDims (1) contains the rectangular structuring element height (z-direction) while maxSEDims (2) contains the rectangular structuring element Width(x-direction). |
| edgeMaxDistance | Double | A scalar defining the maximum allowable distance (in the z-direction) between Canny edge detected points and points of points of maximum intensity (in the z-direction in the intensity map. |
| lengthTrim | Double | A scalar defining the length (in the x-direction) of edge detected connected components ends to trim and replace with translated maximum intensity coordinates found in the same vertical slices as the trimmed edges. |

TABLE A4-continued

Boundary Recognition Parameters

| Variable | Class | Description |
| --- | --- | --- |
| minAcceptableLength | Double | A scalar defining the minimum acceptable length in the x-direction) of the calculated boundary. If the length of the calculated boundary is less than the minimum acceptable length, no boundary is returned. |
| maxDisjointPieces | Double | A scalar defining the maximum acceptable number of horizontally connected components in the calculated boundary. It the number of horizontally connected components exceeds maxDisjointPieces, no boundary is returned. |

TABLE A5

Boundary Recognition Functions

| Function Name | Input Data/ Input Data Class | Input Data Description | Output Data/ Output Data Class | Output Description |
| --- | --- | --- | --- | --- |
| makematrix outofsparse | 1. column matrix/ single 2. column matrix/ single 3. column matrix/ single 4. Scalar variable/ single 5. Scalar variable/ single | Items 1-2 are (x-z) coordinates of the intensity map. Item 3 is the stored intensity for each (x, z) coordinate. Thus, items 1-3 have equal length. Items 4-5 are the minimum spacings between x and z coordinates respectively. | Two dimensional matrix/double | Matrix containing intensity values. Intensity values and their locations are stored in items 1-3. If no intensity can be mapped to a matrix entry, NaN is stored in that entry. |
| fillnan | Two dimensional matrix/double | Matrix containing intensity values of mapped sparse coordinate triples, (x, z, i). | Two dimensional matrix/double | Output matrix is identical to input matrix with sparse NaN entries filled with intensity values of neighbouring, entry intensities. Large blocks of NaN entries are filled with the value 0. |
| leading_edge | 1. Two dimensional matrix/ double 2. scalar variable/ double 3. scalar variable/ double 4. scalar variable/ double 5. scalar variable/ double | Item 1 contains intensity map in 2D matrix format. Items 2 and 3 contain Canny edge detection low and high threshold values respectively. Items 4 and 5 contain Canny edge detection horizontal and vertical sigma values respectively. | 1. Two dimensional matrix/logical 2. Two dimensional matrix/double | 1. Binary image containing detected edges of input item 1. 2. smoothed version of input item 1. |
| computepoints below edgewith indistance | 1. row matrix/single 2. row matrix/single 3. row matrix/single 4. row matrix/single 5. scalar variable/ double | Items 1 and 2 contain x and z coordinates (respectively) of maximum intensity pixels of vertical slices of smoothed map output from leading_edge function. Items 3 and 4 contain x and z coordinates (respectively) of | 1. row matrix/single 2. row matrixidouble | Items 1 and 2 contain respectively the x and z coordinates of maximum intensity pixels lying directly below (having identical x values but greater z values) the edges outputted from function leading_edge. |

TABLE A5-continued

Boundary Recognition Functions

| Function Name | Input Data/ Input Data Class | Input Data Description | Output Data/ Output Data Class | Output Description |
|---|---|---|---|---|
| | | edges output from leading_edge function. | | |
| computepoints above maxline | 1. row matrix/single 2. row matrix/single 3. row matrix/single 4. row matrix/double | Items 1 and 2 contain respectively the x and z coordinates of edges output from the leading_edge function. Items 3 and 4 contain respectively x and z coordinates of maximum intensity pixels outputted from function computepointsbelow edgewithindistance. | 1. row matrix/single 2. row matrix/double | Items 1 and 2 are respectively the x and z coordinates of edges outputted from function leading edge above (having identical x values but smaller z values) input items 3 and 4. |
| computepoints within distance | 1. row matrix/single 2. row matrix/single 3. row matrix/single 4. row matrix/double 5. scalar variable/ double | Items 1 and 2 contain respectively the x and z edge coordinates output from function computepointsabove maxline Items 3 and 4 contain respectively the x and z coordinates the maximum intensity pixels output from function computepointsbelow edgewithindistance Item 5 is the distance (in metres) specifying the maximum distance between input coordinates (1 and 2) and input coordinates (3 and 4) | 1. row matrix/single 2. row matrix/double | Items 1 and 2 are respectively the x and z coordinates of edges within the vertical distance of maximum intensity coordinates output from function computepointsbelowed gewithindistance |
| coords2matrix | 1. Two element vector/ double 2. Two element vector/single 3. Two element vector/single 4. row vector/single 5. row vector/ double | Item 1 contains the height (first element) and width (second element) of the intensity map matrix output from function makematrixoutofsparse Item 2 (resp. 3) contains the lower and higher x-axis (resp. z-axis) limits of the intensity map in its first and second elements. Item 4 (resp. 5) contains the x-axis (resp. z-axis) values of the edge coordinates output from function. | Two dimensional matrix/logical | A binary image containing true in entries mapped from edge locations in input items 4 and 5. False is contained in all other entries. |
| imdilate | 1. Two dimensional matrix/logical 2. rectangular structuring element/ structuring element. | 1. binary image output from function coords2matrix 2. rectangular structuring element used in morphological dilation operation of input item 1. | Two dimensional matrix/logical | Input two dimensional binary matrix post dilation operation. |

TABLE A5-continued

Boundary Recognition Functions

| Function Name | Input Data/ Input Data Class | Input Data Description | Output Data/ Output Data Class | Output Description |
|---|---|---|---|---|
| bwlabeln | Two dimensional matrix/logical | Binary image output from function imdilate | Two dimensional matrix/double | Input matrix with false entries set to 0 and individual connected components enumerated by the positive integers 1, 2, 3, . . . |
| bwmorph | 1. Two dimensional matrix/logical 2. row vector/string 3. scalar variable/ double | 1. Binary image output from function imdilate. 2. string defining morphology operation. String is input as constant, 'thin'. 3. scalar defining the number of thinning operations to perform on input binary image (input item 1). This scalar is set to Inf such that thinning operations will continue to be successively applied until they are no longer effective. | Two dimensional matrix/logical | Input binary image thinned. |
| trimcompon sameline | Two dimensional matrix/logical | Binary image output from bwmorph | Two dimensional matrix/logical | Connected components of input binary image trimmed such that smaller connected components with pixels on the same vertical slices as larger connected components have these pixels set to false. |
| removeall connections between lines | Two dimensional matrix/logical | Binary image output from trimcomponsameline | Two dimensional matrix/logical | Input binary image with all junctions between lines removed. |
| removebottom component | Two dimensional matrix/logical | Binary image output from removeallconnections betweenlines | Two dimensional matrix/logical | Connected components of input binary image trimmed such that only their top (lowest corresponding z value) pixels with respect to any column in the matrix are preserved. |
| removecompon same vertline | Two dimensional matrix/logical | Binary image output from removebottomcomponent | Two dimensional matrix/logical | Connected components of input binary image totally removed such that smaller connected components with pixels on the same vertical slices as larger connected components are set to false. |
| replacecigar tips | 1. Two dimensional matrix/logical 2. Two dimensional matrix/logical 3. scalar/ double 4. rectangular structuring | 1. Binary image output from function removecomponsame vertline containing edges output from function bwlabeln belonging to a particular label 2. Binary image with maximum intensity | Two dimensional matrix/logical | Binary image containing input item 1 with ends of horizontally connected components replaced by vertically translated points in input item 2. |

TABLE A5-continued

Boundary Recognition Functions

| Function Name | Input Data/ Input Data Class | Input Data Description | Output Data/ Output Data Class | Output Description |
|---|---|---|---|---|
| | element/structuring element. | coordinates output from function computepointsbelowedgewithindistance 3. Calculated number of pixels to trim off the horizontal ends of input item 1. 4. rectangular structuring element used in morphological dilation operation of input item 2. | | |
| matrix2coords withnan | 1. Two dimensional matrix/logical 2. Two element vector/single 3. Two element vector/single | Item 1 contains a binary image outputted from function replacecigartips Item 2 (resp. 3) contains the lower and higher x-axis (resp. z-axis) limits of the intensity map in its first and second elements. | 1. column matrix/single 2. column matrix/single | Items 1 and 2 contain respectively the x-axis values and z-axis values of the calculated edge binary image output from function replacecigartips |
| Matrix2coords interp only | 1. Two dimensional matrix/logical 2. Two element vector/single 3. Two element vector/single | Item 1 contains a binary image outputted from function replacecigartips Item 2 (resp. 3) contains the lower and higher x-axis (resp. z-axis) limits of the intensity map in its first and second elements. | 1. column matrix/single 2. column matrix/single | Items 1 and 2 contain respectively the x-axis values and z-axis values of linearly interpolated coordinates of empty regions of the calculated edge binary image output from function replacecigartips |

TABLE A6

Boundary Definition Parameters

| Variable | Class | Description |
|---|---|---|
| width | Single | This determines the width of the median filter used in the MedianFilter function. Width determines the number of data points used when choosing a median to replace a given data point with. |
| smoothWidth | Single | This determines the width of the Savitzky-Golay filter applied in the PerformSmoothing function. |
| smoothOrder | Single | This determines the order of the polynomial used to approximate the surface in the Savitzky-Golay filter applied in the PerformSmoothing function. |

TABLE A7

Boundary Definition Functions

| Function Name | Input Data/ Input Data Class | Input Data Description | Output Data/ Output Data Class | Output Description |
|---|---|---|---|---|
| MedianFilter | 1. 1D column matrix/single 2. 1D column matrix/single 3. positive integer/single | 1. x-components of surface to be filtered 2. y/z-components of surface to be filtered 3. Width of median filter to be used | 1. 1D column matrix/single 2. 1D column matrix/single | 1. x-components of filtered surface 2. y/z-components of filtered surface |

TABLE A7-continued

Boundary Definition Functions

| Function Name | Input Data/ Input Data Class | Input Data Description | Output Data/ Output Data Class | Output Description |
|---|---|---|---|---|
| Perform Smoothing | 1. 1D column matrix/single 2. 1D column matrix/single 3. positive integer/single 4. positive integer/single | 1. x-components of surface to be filtered 2. y/z-components of surface to be filtered 3. Width of smoothing window to be used 4. Order of polynomial used in smoothing approximation | 1. 1D column matrix/single 2. 1D column matrix/single | 1. x-components of smoothed surface 2. y/z-components of smoothed surface |

TABLE A8

IFM OD boundary Preparation Parameters

| Variable | Class | Description |
|---|---|---|
| width | Single | This determines the width of the median filter used in the MedianFilter function. Width determines the number of data points used when choosing a median to replace a given data point with. |
| smoothWidth | Single | This determines the width of the Savitzky-Golay filter applied in the PerformSmoothing function. |
| smoothOrder | Single | This determines the order of the polynomial used to approximate the surface in the Savitzky-Golay filter applied in the PerformSmoothing function. |
| surfaceSamplingInterval | Single | This number is a positive integer. The number 1 would indicate that every point on the given OD surface should be used. The number 2 would indicate to use every other point, the number 3 every third, et cetera. |

TABLE A9

IFM OD boundary Preparation Functions

| Function Name | Input Data/ Input Data Class | Input Data Description | Output Data/ Output Data Class | Output Description |
|---|---|---|---|---|
| MedianFilter | 1. 1D column matrix/single 2. 1D column matrix/single 3. positive integer/single | 1. x-components of surface to be filtered 2. y/z-components of surface to be filtered 3. Width of median filter to be used | 1. 1D column matrix/single 2. 1D column matrix/single | 1. x-components of filtered surface 2. y/z-components of filtered surface |
| Perform Smoothing | 1. 1D column matrix/single 2. 1D column matrix/single 3. positive integer/single 4. positive integer/single | 1. x-components of surface to be filtered 2. y/z-components of surface to be filtered 3. Width of smoothing window to be used 4. Order of polynomial used in smoothing approximation | 1. 1D column matrix/single 2. 1D column matrix/single | 1. x-components of smoothed surface 2. y/z-components of smoothed surface |

TABLE A10

ID Imaging Parameters

| Variable | Class | Description |
| --- | --- | --- |
| directivityCutoff | Single | A real number between 0 and 1 (inclusive) used to determine OD boundary coordinates considered (with respect to the SFM algorithm) to refract ultrasonic waves from individual array elements.<br>If the calculated directivity from an element to an OD boundary coordinate is lower than directivityCutoff, then that OD boundary coordinate is programmatically not considered to refract sound from the element. To calculate the directivity of an element to a specified location, a formula which approximates directivity is used (see Theory Manual [R – 1]). |
| speedOfMedium2 | Single | A real number defining the speed at which sound travels in the second inspection material found between the OD and ID surfaces. |
| xMin | Single | A real number defining the absolute lower limit of x-components of intensity map coordinates (in millimetres). xMin is less than xMax.<br>Where y is the minimum x-component of the OD boundary, the actual lower limit of the x-components of intensity map coordinates is the maximum of the following two scalars, xMin and y-horzBuffer. |
| xMax | Single | A real number defining the absolute upper limit of x-components of intensity map coordinates (in millimetres). xMin is less than xMax.<br>Where y' is the maximum x-component of the OD boundary, the actual upper limit of the x-components of intensity map coordinates is the minimum of the following two scalars, xMax and y'+horzBuffer. |
| horzBuffer | Single | A real number bounding x-component coordinates of the IFM intensity map.<br>Where y is the minimum x-component of the OD boundary, the actual lower limit of the x-components of intensity map coordinates is the maximum of the following two scalars, xMin and y–horzBuffer.<br>Where y' is the maximum x-component of the OD boundary, the actual upper limit of the x-components of intensity map coordinates is the minimum of the following two scalars, xMax and y'+horzBuffer. |
| xSpacing | Single | A vector of length n specifying x-spacings at which to iteratively perform computation of intensities at intensity map coordinates. A total of n iterations of intensity computations are performed (assuming intensity computations do not need to be further broken up to satisfy memory requirements).<br>Coarser spacings are specified toward the lesser indices of the vector while finer spacings are specified toward the finer indices of the vector. Additionally for every i between 1 and n – 1, $dx(i + 1)/dx(i)$ is a positive integer. |
| zSpacing | Single | A vector of length n specifying z-spacings at which to iteratively perform computation of intensities at intensity map coordinates. A total of n iterations of intensity computations are performed (assuming intensity computations do not need to be further broken up to satisfy memory requirements).<br>Coarser spacings are specified toward the lesser indices of the vector while finer spacings are specified toward the finer indices of the vector. Additionally for every i between 1 and n – 1 $dz(i + 1)/dz(i)$ is a positive integer. |
| firstDiagIndex | Single | A positive scalar greater than 0 and less than lastdiagindex. This number indicates the first element in the probe array that should be used for the IFM intensity-map computation. |
| lastDiagIndex | single | A positive scalar greater than firstdiagindex and less than the number of elements in the probe array. This number indicates the last element in the probe array that should be used for the IFM intensity-map computation. |
| zoomPercentages | Single | A vector of length n – 1 implicitly specifying coordinates in the intensity map to focus around upon iterative computation of coordinate intensities.<br>For i between 1 and n – 1, zoomPercentage(i) contains a real number between 0 and 1 inclusive. On iteration i + 1 of coordinate intensity computation, where Imax is the maximum tensity calculated in the intensity map, the coordinates in which to focus around are those of intensity greater than zoomPercentage(i) * Imax. |
| maxTransmitterReceiverDifference | single | A positive scalar defining the maximum absolute difference between a transmitter and receiver used in combination for IFM intensity map computation. |
| criticalPoints | Char | One of the following three strings: 'mins', 'maxes', or 'minsandmaxes.' If criticalPoints is equal to 'mins' (resp. |

TABLE A10-continued

ID Imaging Parameters

| Variable | Class | Description |
|---|---|---|
| | | 'maxes'), then only local minimums (resp. maximums) of travel path times are considered to be true travel paths of refracted ultrasonic waves. If criticalPoints is equal to 'minsandmaxes', then both local minimums and local maximums of travel path times are considered to be true travel paths of refracted ultrasonics waves. |
| doNormalization | logical | If doNormalization is set to true, then normalization of all A-Scans for IFM computation is executed. Otherwise, if doNormalization is set to false, no normalization is calculated. |
| theshold | Single | A real number greater than 0 and less than or equal to 100. This number specifies the cutoff envelope height of wave packets to be normalized in A-Scan data Where we let 'y' be the maximum envelope value of all FMC data, wavepacket information with peak height greater or equal to threshold * y/100 will be normalized. All other information in the A-Scans will be set to 0. Recall the envelope of hilbertized data is simply its magnitude. |
| width | Single | A positive scalar greater than 1 and less than or equal to any nonzero length of AScan contained in the FMC data. This number specifies the distance (in digitization points) between distinct wave packets in an A-Scan. If the distance between envelope peaks greater than the threshold variable exceeds the variable width, then envelope peaks are considered to belong to distinct wave packets. Othemise, the envelope peaks are considered to belong to the same wave packets. |
| Runup | single | A positive scalar greater than 1 and less than or equal to any nonzero length of AScan contained in the FMC data. This number specifies the number (in digitization points) of A-Scan values ahead of envelope peaks with values greater than the threshold variable to normalize along with the envelope peaks themselves. |

TABLE A11

ID Imaging Functions

| Function Name | Input Data/ Input Data Class | Input Data Description | Output Data/ Output Data Class | Output Description |
|---|---|---|---|---|
| O_compute surface directivityfactor | 1. 1D column matrix/single 2. 1D column matrix/single 3. 1D column matrix/single 4. scalar/single. | 1. x-coordinates of probe array elements. 2. x-coordinates of surface. 3. z-coordinates of surface. 4. wavelength of excitation pulse in water. | 1. 2D matrix/logical | Entry (j,k) contains 'true' if the directivity from element j to surface coordinate with index k is greater than or equal to the 'surfaceDirectivityCutoff', defined globally. It contains 'false' otherwise. |
| O_compute surface probearray times | 1. 1D column matrix/single 2. 1D column matrix/single 3. 1D column matrix/single 4. scalar/single. | 1. x-coordinates of surface. 2. z-coordinates of surface. 3. x-coordinates of probe array elements. 4. speed of sound in water. | 2D matrix/single | Entry (j,k) contains the time needed for a sound pulse to travel from element k in the probe array to surface coordinate with index j. |
| o_compute idcoordinates | 1. 1D column matrix/single 2. 1D column matrix/single | 1. x-component of surface coordinates, 2. z-component of surface coordinates | 1. 1D column matrix/ single 2. 1D column matrix/ single. | 1. x-component of coordinates of initial intensity computation. 2. z-component of coordinates of initial intensity computation. |
| o_compute currfinecoords 4_id | 1. 1D column matrix/single 2. 1D column matrix/single 3. 1D column matrix/single | 1. x-component of coordinates of previous loop iteration's intensity computation. | 1. 1D column matrix/ single. 2. 1D column | 1. x-coordinate of neighbourhood of intensity map coordinates exceeding specified intensity cutoff. |

TABLE A11-continued

ID Imaging Functions

| Function Name | Input Data/ Input Data Class | Input Data Description | Output Data/ Output Data Class | Output Description |
|---|---|---|---|---|
| | 4. 1D column matrix/single 5. positive integer/ double. | 2. z-component of coordinates of previous loop iteration's intensity computation. 3. x-component of surface coordinates. 4. z-component of surface coordinates. 5. iteration of intensity computation loop. | matrix/ single. | 2. z-coordinate of neighbourhood of intensity map coordinates exceeding specified intensity cutoff. |
| O_remove idcoords outsidebounds3 | 1. 1D column matrix/single 2. 1D column matrix/single 3. 1D column matrix/single 4. 1D column matrix/single | 1. x-component of candidate coordinates of current loop iteration's intensity computation. 2. z-component of candidate coordinates of current loop iteration's intensity computation. 3. x-component of surface coordinates. 4. z-component of surface coordinates. | 1. 1D column matrix/ single 2. 1D column matrix/ single. | 1. x-component of coordinates of current loop iteration's intensity computation within defined intensity map boundaries. 2. z-component of coordinates of current loop iteration's intensity computation within defined inteiisity map boundaries, |
| O_compute coordvisibility from surface 10 | 1. 1D column matrix/single 2. 1D column matrix/single 3. 1D column matrix/single 4.1D column matrix/single | 1. x-component of coordinates of current loop iteration's intensity computation. 2. z-component of coordinates of current loop iteration's intensity computation. 3. x-component of surface coordinates. 4. z-component of surface coordinates. | 1. 1D column matrix/ single 2. 1D column matrix/ single. 3. 2D matrix/ logical | 1. sorted x-component of coordinates of current loop iteraton's intensity. computation. 2. sorted z-component of coordinates of current loop iteration's intensity computation. 3. Entry (j, k) is 'true' if there is a straight line from surface coordinate k to intensity map coordinate j which does not intersect the input surface (except at coordinate j). Entry (j, k) is 'false' otherwise. |
| O_compute surface coordtimes | 1. 1D column matrix/single 2. 1D column matrix/single 3. 1D column matrix/single 4. 1D column matrix/single | 1. x-component of coordinates of current loop iteration's intensity computation. 2. z-component of coordinates of current loop iteration's intensity computation. 3. x-component of surface coordinates. 4. z-component of surface coordinates. | 1. 2D matrix/ single. | 1. Entry (j, k) is the travel time of sound in water from element k to surface coordinate with index j. |

TABLE A11-continued

ID Imaging Functions

| Function Name | Input Data/ Input Data Class | Input Data Description | Output Data/ Output Data Class | Output Description |
|---|---|---|---|---|
| O_compute travel times4 | 1. 2D matrix/single 2. 2D matrix/single 3. 2D matrix/logical 4. 2D matrix/logical | 1. Entry (j, k) is the travel time of sound in water from element k to surface coordinate with index j. 2. Entry (j, k) contains the time needed for a sound pulse to travel from element k in the probe array to surface coordinate with index j. 3. Entry (j, k) contains 'true' if the directivity from element j to surface coordinate with index k is greater than or equal to the 'surfaceDirectivity Cutoff', defined globally. It contains 'false' 4. Entry (j, k) is 'true' if there is a straight line from surface coordinate k to intensity map coordinate j which does not intersect the input surface (except at coordinate j). Entry (j, k) is 'false' otherwise. | 1. Structure with fields: a) column matrix/unsigned int (16-bit). b) column matrix single c) column matrix/unsigned integer (8 bit) d) column matrix/unsigned integer (8-bit) e) scalar/ unsigned integer (8-bit) | With respect to index i of the structure (corresponding to element i of the linear probe array). a) entry j contains the index of a coordinate b) entry j contains the travel time (in samples) from element i to the coordinate with index j in field a). c) entry j contains the number travel-time solutions from element I to the coordinate with index j in field a). d) contains the set of number of solutions from element i to all inspection coordinates. e) contains the length of field d). |
| O_ifmzoom8 | 1. 2 × 1 element matrix/double 2. 2D matrix/ complex single 3. 2D matrix/single 4. 2D matrix/single 5. Structure with fields: a) column matrix/unsigned int (16-bit). b) column matrix/single c) column matrix/unsigned integer (8 bit) d) column matrix/unsigned integer (8-bit) e) scalar/ unsigned integer (8-bit) | 1. Size of coordinate matrices 2. FMC data-set where A-Scans are contained in the vertical dimension. 3. Entry (i, j) contains the column index of the A-Scan belonging to transmitter i and receiver j. 4. Entry (i, j) contains the offset (in samples) between transmission of ultrasonic wave from element i and recording of A-Scan data from receiver j. 5. With respect to index i of the structure (corresponding to element i of the | 1. column matrix/single | 1. computed intensities for coordinates with matching indices as computed intensities. |

TABLE A11-continued

ID Imaging Functions

| Function Name | Input Data/ Input Data Class | Input Data Description | Output Data/ Output Data Class | Output Description |
|---|---|---|---|---|
| | | linear probe array). a) entry j contains the index of a coordinate b) entry j contains the travel time (in samples) from element i to the coordinate with index j in field a). c) entry j contains the number travel-time solutions from element I to the coordinate with index j in field a). d) contains the set of number of solutions from element i to all inspection coordinates. e) contains the length of field d). | | |
| O_compute coordinates above cutoff_id | 1. column matrix/single 2. column matrix/single 3. column matrix/single 4. scalar/single. | 1. coordinate x-components 2. coordinate z-components. 3. coordinate intensities 4. cutoff intensity value. | 1. column matrix/ single. 2. column matrix/ single. | 1. coordinate x-components With intensity values exceeding cutoff intensity value (input item 4). 2. coordinate z-components with intensity values exceeding cutoff intensity value (input item 4). |

TABLE A12

2" Reference Block (Serial Number 001) Dimensions

| Location Scan | Block | Measurement converted from Imperial | Rounded Measurement | Step Delta |
|---|---|---|---|---|
| | 1 | 2.032 | 2.03 | |
| | 2 | 5.0038 | 5.00 | |
| | 3 | 8.00608 | 8.01 | |
| | 4 | 10.9982 | 11.00 | |
| | 5 | 13.9827 | 13.98 | |
| | 6 | 16.99006 | 16.99 | |
| | 7 | 23.89632 | 23.90 | 3.00 |
| | 8 | 20.89912 | 20.90 | 3.00 |
| | 9 | 17.89684 | 17.90 | 3.00 |
| | 10 | 14.89964 | 14.90 | 3.00 |
| | 11 | 11.89736 | 11.90 | 2.97 |
| | 12 | 8.9281 | 8.93 | |

TABLE A13

2" Reference Block (Serial Number 002) Dimensions

| Location Scan | Block | Measurement converted from Imperial | Rounded Measurement | Step Delta |
|---|---|---|---|---|
| | 1 | 2.032 | 2.03 | |
| | 2 | 5.00888 | 5.01 | |
| | 3 | 8.0264 | 8.03 | |
| | 4 | 11.0109 | 11.01 | |
| | 5 | 13.99286 | 13.99 | |
| | 6 | 17.00022 | 17.00 | |
| | 7 | 23.89378 | 23.89 | 2.99 |
| | 8 | 20.9042 | 20.90 | 3.01 |
| | 9 | 17.8943 | 17.69 | 3.00 |
| | 10 | 14.8971 | 14.90 | 3.00 |
| | 11 | 11.8999 | 11.90 | 2.98 |
| | 12 | 8.9154 | 8.92 | |

TABLE A14

2.5" Reference Block (Serial Number 001) Dimensions

| Location Scan | Block | Measurement converted from Imperial | Rounded Measurement | Step Delta |
|---|---|---|---|---|
| | 1 | 1.99898 | 2.00 | |
| | 2 | 4.99872 | 5.00 | |
| | 3 | 8.001 | 8.00 | |
| | 4 | 10.9982 | 11.00 | |
| | 5 | 13.9954 | 14.00 | |
| | 6 | 16.99768 | 17.00 | |

TABLE A14-continued 2.5" Reference Block (Serial Number 001) Dimensions

| Location Scan | Block | Measurement converted from Imperial | Rounded Measurement | Step Delta |
|---|---|---|---|---|
| | 7 | 24.0919 | 24.09 | 3.00 |
| | 8 | 21.0947 | 21.10 | 3.01 |
| | 9 | 18.0848 | 18.09 | 2.99 |
| | 10 | 15.09522 | 15.10 | 3.00 |
| | 11 | 12.09802 | 12.10 | 3.01 |
| | 12 | 9.0932 | 9.09 | |

TABLE A15

2.5" Reference Block (Serial Number 002) Dimensions

| Location Scan | Block | Measurement converted from Imperial | Rounded Measurement | Step Delta |
|---|---|---|---|---|
| | 1 | 2.00406 | 2.00 | |
| | 2 | 4.99364 | 4.99 | |
| | 3 | 7.99592 | 8.00 | |
| | 4 | 10.9982 | 11.00 | |
| | 5 | 13.9954 | 14.00 | |
| | 6 | 16.9926 | 16.99 | |
| | 7 | 24.09698 | 24.10 | 3.00 |
| | 8 | 21.10232 | 21.10 | 3.01 |
| | 9 | 18.0975 | 18.10 | 2.99 |
| | 10 | 15.10538 | 15.11 | 3.01 |
| | 11 | 12.09294 | 12.09 | 3.00 |
| | 12 | 9.0932 | 9.09 | |

The present disclosure may be embodied in other specific forms without departing from its spirit or essential characteristics. The described embodiments are to be considered in all respects as being only illustrative and not restrictive. The present disclosure intends to cover and embrace all suitable changes in technology.

We claim:

1. A device for performing ultrasound scanning of an outside and an inside of a conduit, comprising:
    a cuff adapted to fit around an outer circumference of the conduit;
    a carrier mounted slidably on the cuff and adapted to traverse the outer circumference of the conduit;
    an ultrasound probe mounted on the carrier, the ultrasound probe comprising an array of ultrasound transceivers arrayed to be substantially parallel to a longitudinal axis of the conduit when the cuff is fitted around the conduit, and positioned to project ultrasound waves tangential to the outer circumference of the conduit as the carrier traverses the outer circumference of the conduit;
    a carrier motor mounted on the cuff or the carrier and used to drive the movement of the carrier about the outer circumference of the conduit;
    an adjustable reflector mounted to the carrier;
    a reflector motor for controlling an angle of the adjustable reflector in a plane substantially normal to the longitudinal axis of the conduit; and
    one or more data connections providing control information for the carrier motor, the reflector motor and the ultrasound probe and receiving scanning data from the ultrasound probe;
    wherein:
        the cuff forms liquid-resistant seals between the outer circumference of the conduit and the cuff;
        the ultrasound probe and the adjustable reflector are positioned to scan the conduit via reflection of the ultrasound signals off of the adjustable reflector; and
    the device further comprising a liquid feed for receiving a liquid scanning medium and filling a volume defined between an interior of the cuff and an exterior of the conduit with the liquid scanning medium.

2. The device of claim 1, further comprising a power connection for receiving electrical power for the carrier motor.

3. The device of claim 1, wherein the cuff is configurable between an open configuration allowing it to be fitted around the conduit and a closed configuration encircling the conduit.

4. The device of claim 1, further comprising a power connection for receiving electrical power for the reflector motor.

5. The device of claim 1, wherein the conduit is a cylinder.

6. The device of claim 3, wherein the cuff comprises a knuckle which releasably secures a first half of said cuff to a second half of said cuff.

7. The device of claim 3, wherein the cuff comprises a first half of said cuff detachable from a second half of said cuff.

8. The device of claim 1, further comprising a controller configured to output the control information via the one or more data connections, wherein the control information controls the ultrasound probe to perform a full-matrix-capture scan of a first point about the circumference of the conduit by:
    transmitting an ultrasound signal from a first ultrasound element in the array of ultrasound transceivers;
    sensing and recording ultrasound signals received by each other ultrasound element in the array of ultrasound transceivers; and
    repeating the steps of transmitting, sensing and recording, wherein the step of transmitting is performed in turn by each ultrasound element in the array of ultrasound transceivers other than the first ultrasound element.

9. The device of claim 8, wherein the control information further controls the ultrasound probe and the reflector motor to adjust the angle of the adjustable reflector by:
    prior to performing the full-matrix-capture scan, transmitting ultrasound signal from one or more elements in the array of ultrasound transceivers at different angles of the adjustable reflector;
    sensing ultrasound signals received by one or more elements in the array of ultrasound transceivers at each different angle; and
    selecting the angle of the adjustable reflector for performing the full-matrix-capture scan based on an amplitude of the sensed ultrasound signals.

10. The device of claim 8, wherein the control information further controls the ultrasound probe and the carrier motor to:
    reposition the ultrasound array at a second point about the circumference of the conduit; and
    perform a full-matrix-capture scan of the second point about the circumference of the conduit.

11. A method for performing ultrasound scanning of a conduit, comprising:
    providing an ultrasound device for scanning an outside and an inside of the conduit, the device comprising:
        a cuff adapted to fit around an outer circumference of the conduit, the cuff forming liquid-resistant seals between the outer circumference of the conduit and the cuff;

a carrier mounted slidably on the cuff and adapted to traverse the outer circumference of the conduit;

an ultrasound probe mounted on the carrier and positioned to project ultrasound waves tangential to the outer circumference of the conduit as the carrier traverses the outer circumference of the conduit, the ultrasound probe comprising an ultrasound array having a plurality of ultrasound elements arrayed substantially parallel to a longitudinal axis of the conduit;

a carrier motor mounted on the cuff or the carrier and used to drive the movement of the carrier about the outer circumference of the conduit;

a liquid feed for receiving a liquid scanning medium and filling a volume defined between an interior of the cuff and an exterior of the conduit with the liquid scanning medium;

an adjustable reflector mounted to the carrier;

a reflector motor for controlling an angle of the adjustable reflector in a plane substantially normal to a longitudinal axis of the conduit; and one or more data connections providing control information for the carrier motor, the ultrasound probe and the reflector motor, and receiving scanning data from the ultrasound probe;

positioning the ultrasound array and the adjustable reflector to project the ultrasound signals toward an external surface of the conduit at a first point about the circumference of the conduit via reflection of the ultrasound signals off of the adjustable reflector;

performing a full-matrix-capture scan of the first point about the circumference of the conduit, comprising:

transmitting an ultrasound signal from a first ultrasound element in the ultrasound array;

sensing and recording ultrasound signals received by each other ultrasound element in the ultrasound array; and repeating the steps of transmitting, sensing and recording, wherein the step of transmitting is performed in turn by each ultrasound element in the ultrasound array other than the first ultrasound element;

repositioning the ultrasound array at a second point about the circumference of the conduit;

performing a full-matrix-capture scan of the second point about the circumference of the conduit; and repeating the steps of repositioning and performing a full-matrix-capture scan.

* * * * *